US009950999B2

(12) United States Patent
Ishimaru et al.

(10) Patent No.: US 9,950,999 B2
(45) Date of Patent: Apr. 24, 2018

(54) NON-IONIC LOW DIFFUSING PHOTO-ACID GENERATORS

(71) Applicants: International Business Machines Corporation, Armonk, NY (US); Central Glass Co., Ltd., Yamaguchi (JP)

(72) Inventors: Takehisa Ishimaru, Tokyo (JP); Satoru Narizuka, Kawagoe (JP); Daniel P. Sanders, San Jose, CA (US); Ratnam Sooriyakumaran, San Jose, CA (US); Hoa D. Truong, San Jose, CA (US); Rudy J. Wojtecki, San Jose, CA (US)

(73) Assignees: International Business Machines Corporation, Armonk, NY (US); Central Glass Co., Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 15/235,342

(22) Filed: Aug. 12, 2016

(65) Prior Publication Data

US 2018/0044284 A1    Feb. 15, 2018

(51) Int. Cl.
| | | |
|---|---|---|
| *G03F 7/004* | (2006.01) | |
| *G03F 7/38* | (2006.01) | |
| *C07C 317/04* | (2006.01) | |
| *C07C 317/06* | (2006.01) | |
| *C07C 317/08* | (2006.01) | |
| *C07C 317/10* | (2006.01) | |
| *C07C 317/14* | (2006.01) | |
| *C07C 317/24* | (2006.01) | |
| *C07C 317/26* | (2006.01) | |
| *C07C 317/32* | (2006.01) | |
| *C07C 309/69* | (2006.01) | |
| *G03F 7/039* | (2006.01) | |
| *G03F 7/038* | (2006.01) | |
| *G03F 7/16* | (2006.01) | |
| *G03F 7/20* | (2006.01) | |
| *G03F 7/32* | (2006.01) | |

(52) U.S. Cl.
CPC .......... *C07C 309/69* (2013.01); *G03F 7/0045* (2013.01); *G03F 7/0046* (2013.01); *G03F 7/0382* (2013.01); *G03F 7/0392* (2013.01); *G03F 7/168* (2013.01); *G03F 7/2004* (2013.01); *G03F 7/322* (2013.01); *G03F 7/38* (2013.01)

(58) Field of Classification Search
CPC .... G03F 7/0045; G03F 7/0397; G03F 7/0046; C07C 317/04; C07C 317/06; C07C 317/08; C07C 317/10; C07C 317/14; C07C 317/24; C07C 317/26; C07C 317/32; C07C 309/69

USPC ........... 430/270.1, 919, 921, 325, 326, 330; 568/28, 30, 31, 32, 33, 34, 35
See application file for complete search history.

(56) References Cited

U.S. PATENT DOCUMENTS

| | | | |
|---|---|---|---|
| 2,322,760 A | 6/1943 | Lantz | |
| 5,135,838 A | 8/1992 | Houlihan et al. | |
| 5,304,456 A | 4/1994 | Ueda et al. | |
| 5,830,619 A | 11/1998 | Chin et al. | |
| 6,855,476 B2 * | 2/2005 | Ferreira | C07C 309/10 430/270.1 |
| 7,326,511 B2 | 2/2008 | Matsumoto et al. | |
| 7,456,133 B2 | 11/2008 | Herrmann et al. | |
| 8,268,531 B2 | 9/2012 | Ober et al. | |
| 8,329,377 B2 | 12/2012 | Takemoto et al. | |
| 9,223,208 B2 * | 12/2015 | Tsuchimura | C07C 317/44 |
| 9,244,345 B1 | 1/2016 | Ishimaru et al. | |
| 9,274,420 B2 * | 3/2016 | Akiba | G03F 7/0045 |
| 2002/0197558 A1 | 12/2002 | Ferreira et al. | |
| 2013/0122427 A1 | 5/2013 | Kataoka et al. | |
| 2014/0065541 A1 * | 3/2014 | Akiba | G03F 7/0045 430/283.1 |
| 2014/0093823 A1 * | 4/2014 | Brainard | G03F 7/0045 430/283.1 |
| 2014/0193752 A1 * | 7/2014 | Brainard | C07C 309/65 430/283.1 |

FOREIGN PATENT DOCUMENTS

| | | | |
|---|---|---|---|
| EP | 0717319 B1 | 11/2001 | |
| JP | 2002236358 A | 8/2002 | |
| JP | 2004519520 A | 7/2004 | |
| JP | 4145017 B2 | 9/2008 | |
| WO | 02082185 A1 | 10/2002 | |

OTHER PUBLICATIONS

Hinsberg, et al., "Effect of Resist Components on Image Spreading During Postexposure Bake of Chemically Amplified Resists", Proceedings of SPIE vol. 3999 (2000), pp. 148-160.
Storer, et al., "Aracyl triflates for preparing fluorescent and UV absorbing derivatives of unreactive carboxylates, amines and other metabolites", Analytica Chimica Acta, vol. 558, Issues 1-2, Feb. 3, 2006, pp. 319-325.
U.S. Appl. No. 15/235,410, filed Aug. 12, 2016.
U.S. Appl. No. 15/235,673, filed Aug. 12, 2016.

* cited by examiner

*Primary Examiner* — John S Chu
(74) *Attorney, Agent, or Firm* — Michael R. Roberts

(57) ABSTRACT

Non-ionic photo-acid generating (PAG) compounds were prepared that contain an aryl ketone group. The disclosed non-polymeric PAGs release a strong sulfonic acid when exposed to high energy radiation such as deep UV or extreme UV light. The photo-generated sulfonic acid has a low diffusion rate in an exposed resist layer subjected to a post-exposure bake (PEB) at 100° C. to 150° C., resulting in formation of good line patterns after development. At higher temperatures, the PAGs undergo a thermal reaction to form a sulfonic acid.

22 Claims, 26 Drawing Sheets

1. Optional PAB
2. Expose

1. Optional PEB
2. Develop

1. Transfer
2. Etch

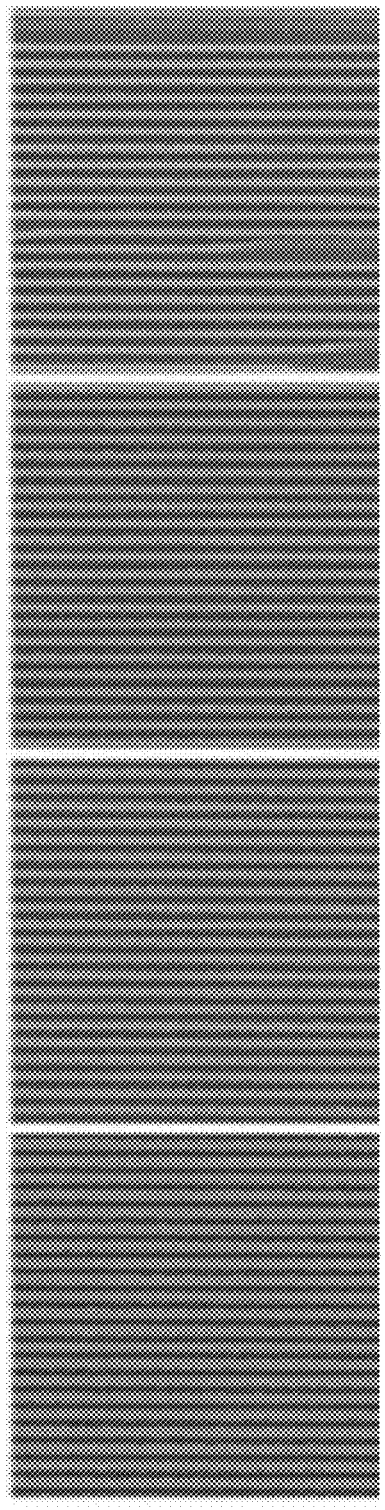
FIG. 13A (7.5 mJ)  FIG. 13B (8.4 mJ)  FIG. 13C (9.5 mJ)  FIG. 13D (10.4 mJ)

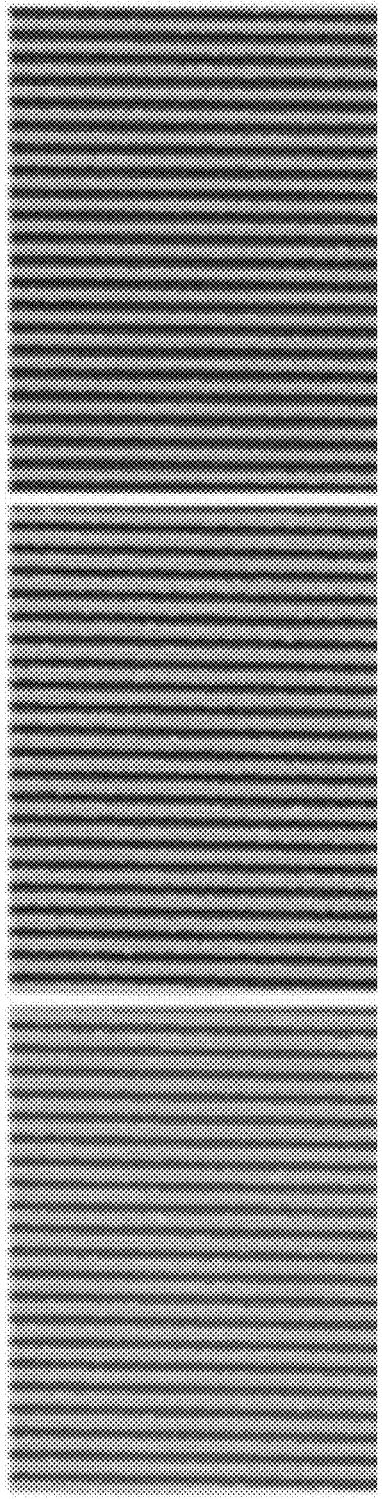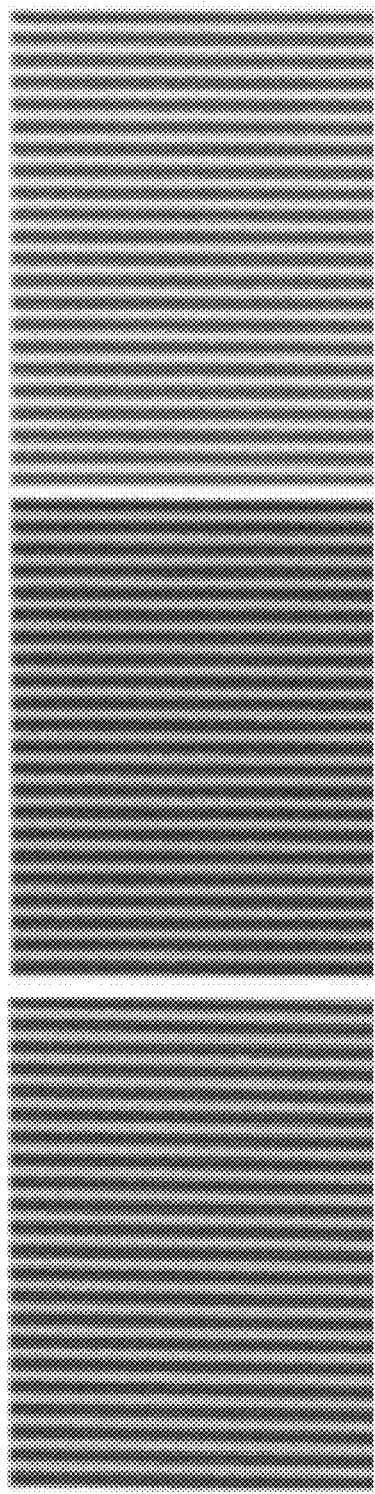
FIG. 16A (9.5 mJ)
FIG. 16B (10.4 mJ)
FIG. 16C (11.5 mJ)
FIG. 16D (12.4 mJ)
FIG. 16E (14.4 mJ)
FIG. 16F (13.5 mJ)

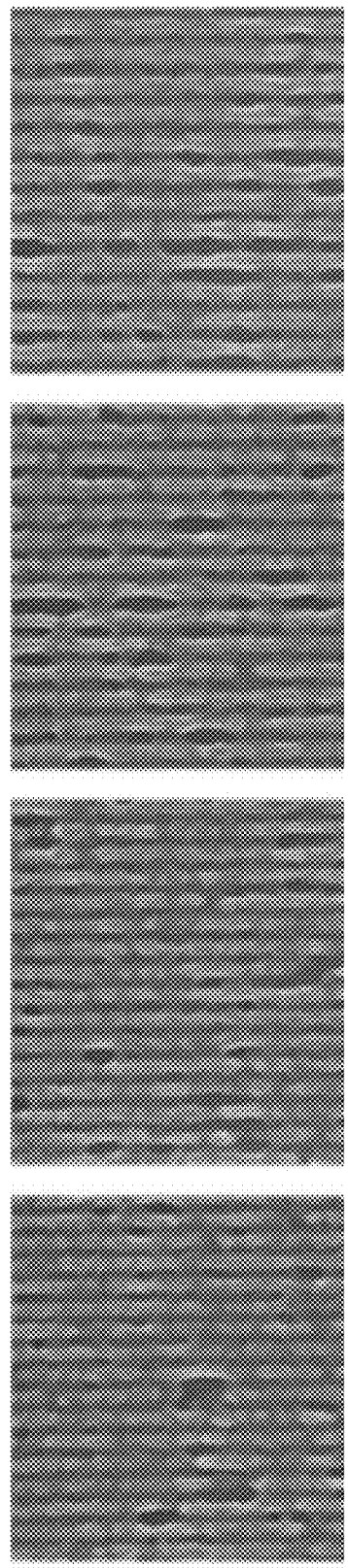

NON-IONIC LOW DIFFUSING PHOTO-ACID GENERATORS

BACKGROUND

The present invention relates to non-ionic low diffusing photo-acid generators (PAGs), and more specifically to PAGS based on fluorinated sulfonic acids protected with aryl ketone protecting groups for lithographic applications.

Extreme Ultraviolet (EUV) lithography is expected to succeed current 193 nm immersion lithography combined with multiple patterning enhancements as the next generation printing technique. EUV radiation, with a shorter wavelength of 13.5 nm, is expected to achieve sub-20 nm features in a single exposure process. However, more advances in efficient light sources, EUV masks, and resists are needed for EUV lithography to become a manufacturing process.

During the last few years, considerable effort has gone into the development of resists for EUV applications. However, the majority of the EUV resists have been modified from the resists developed for 193 nm and 248 nm applications.

The highest performing photoresists for 193 nm and 248 nm applications are all based on a chemical amplification mechanism. Chemically amplified photoresists utilize a catalytic mechanism to generate a relatively large number of chemical events (e.g., deprotection reactions in the case of positive tone photoresists, or crosslinking reactions in the case of negative tone photoresists). Application of a relatively low dose of radiation induces formation of the catalyst, often a strong acid, which then catalyzes the chemical events. The current positive resist compositions comprise aqueous base soluble functional groups that are sufficiently protected with acid-labile groups so that the resist initially will not dissolve in an aqueous base developer. During exposure to radiation, the photoacid generator (PAG) present in the resist composition produces a strong acid, which then catalyzes the removal of the acid-labile groups upon heating exposed resist layer in a post-exposure bake (PEB). This process produces aqueous base soluble material in the exposed area, which then is selectively removed with a basic aqueous developer to produce the images.

One phenomenon that limits the resolution potential of the resists developed for 248 nm, 193 nm and E-beam applications is referred to as "image blur" (see, e.g., Hinsberg et al., Proc. SPIE, (2000), 3999, 148). Image blur is generally thought to result from two contributing factors: gradient-driven acid diffusion and reaction propagation, the result being a distortion in the developable image compared to the projected aerial image transferred onto the film. This becomes critical in EUV applications because of the need for small features with low line edge roughness (LER). Therefore, a need exists to control the gradient driven acid-diffusion in the resist films.

Most widely reported PAGs in the resist formulations are ionic in nature (triphenylsulfonium or iodonium sulfonates). Non-ionic PAGs have some advantages such as higher solubility in casting solvents and homogeneous distribution in the resist film. Previously, a few non-ionic PAGs having imide photo-labile groups have been reported (U.S. Pat. No. 8,329,377 B2 to Takemoto, et al.).

In the area of photo acid generators (PAGs), a limited number of PAGs having aryl ketone protecting groups have been reported. U.S. Pat. No. 5,304,456 to Ueda, et al. discloses PAGs with perfluoro alkyl sulfonic acids. WO 02/082185/A1 (JP2004519520A) to Ferreira, et al. and JP2002236358A (JP4145017B2) to Kunihiko disclose PAGs with perfluoroalkyl and perfluoro ether substituted sulfonic acids. Similarly, aryl ketone triflate PAGs have been described by Storer, et al., Analytica Chimica Acta (2006), volume 558(1-2), pages 319-325. These previously reported aryl ketone PAGs produce volatile and highly diffusing sulfonic acids that can be unstable in resist formulations.

Therefore, a need exists for aryl ketone protected PAGs that have higher thermal and hydrolytic stability in resist formulations and produce less volatile, low diffusing sulfonic acids.

SUMMARY

Accordingly, a compound is disclosed of formula (3):

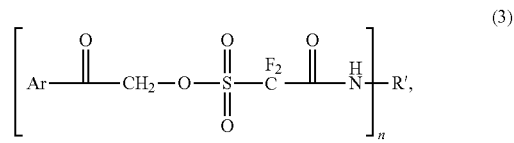

wherein
n is a positive integer having a value of 1-4,
Ar is a monovalent aryl radical comprising one or more aromatic rings, and
R' is a hydrocarbon radical having a valency of n and comprising 2-20 carbons.

Further disclosed is a resist formulation, comprising:
a solvent;
a resin capable of chemical amplification;
a base quencher; and
an above-described PAG compound;
wherein
the resin, the base quencher, and the PAG compound are in contact with the solvent, and
the resist formulation is suitable for use in a lithographic process.

Also disclosed is a method, comprising:
casting a resist formulation comprising a solvent, a resin capable of chemical amplification, a base, and an above-described PAG compound on a surface of a substrate and removing the solvent, thereby forming a layered structure, the layered structure comprising a resist layer disposed on the surface of the substrate, the resist layer comprising the resin, the base quencher, and the PAG compound;
optionally baking the resist layer;
exposing the resist layer pattern-wise to radiation, thereby forming an exposed resist layer comprising exposed regions of the resist layer and non-exposed regions of the resist layer, the exposed regions of resist layer comprising an acid formed by exposing the PAG compound to the radiation;
heating the exposed resist layer, thereby forming a heated exposed resist layer comprising heated exposed regions of the exposed resist layer and heated non-exposed regions of the exposed resist layer, wherein the heated exposed regions have greater solubility in a given alkaline developer compared to the heated non-exposed regions; and
selectively removing the heated exposed regions using the given alkaline developer, thereby forming a patterned resist layer disposed on the surface of the substrate, the patterned resist layer comprising the heated non-exposed regions of the heated exposed resist layer.

Another method is disclosed, comprising:
casting a resist formulation comprising a solvent, a resin capable of chemical amplification, a base, and an above-described PAG compound on a surface of a substrate and removing the solvent, thereby forming a layered structure comprising a resist layer disposed on the surface of the substrate, the resist layer comprising the resin, the base quencher, and the PAG compound;

optionally baking the resist layer;

exposing the resist layer pattern-wise to radiation, thereby forming an exposed resist layer comprising exposed regions and non-exposed regions of the exposed resist layer, the exposed regions of exposed resist layer comprising an acid formed by exposing the PAG compound to the radiation;

heating the exposed resist layer, thereby forming a heated exposed resist layer comprising heated exposed regions and heated non-exposed regions of the heated exposed resist layer, wherein the heated exposed regions have lower solubility in a given developer compared to the heated non-exposed regions; and selectively removing the heated non-exposed regions using the given developer, thereby forming a patterned resist layer disposed on the surface of the substrate, the patterned resist layer comprising the heated exposed regions of the heated exposed resist layer.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIGS. 13A-13D are SEMs of 80 nm HP line patterns obtained using doses of 5.1 mJ, 5.9 mJ, and 6.4 mJ, respectively, with resist layers formed with PAG-9.

FIGS. 16A-16F are SEMs of 80 nm HP line patterns obtained with doses of 9.5 mJ, 10.4 mJ, 11.5 mJ, 12.4 mJ, 14.4 mJ, and 13.5 mJ, respectively, of resist layers containing PAG-9, imaged at 193 nm.

FIGS. 20A-20D are SEMs of line patterns having half pitch 30 nm, 32 nm, 36 nm, and 40 nm, respectively, obtained with resist layers containing DPAG-2, exposed at 13.5 nm (EUV-MET). The dose was 45.8 mJ. The resist layers (film thickness ~40 nm) contained 0.99 parts quencher 1. Each line pattern showed scum and lifting.

DETAILED DESCRIPTION

Figure 1A:
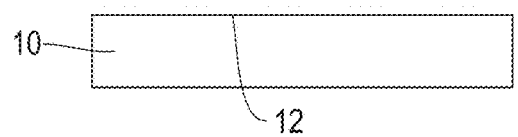
FIGS. 1A to 1E are schematic layer diagrams showing a method of forming a multi-layered structure that includes a topographical patterned layer comprising exposed resist composition.

Disclosed are non-ionic photo-acid generating (PAG) compounds for lithography. The non-polymeric PAGs, which contain an aryl ketone group, release a strong sulfonic acid upon a lithographic exposure. The strong acid has a low diffusion rate when the exposed resist layer is heated in a post-exposure bake (PEB) at a temperature in the range of about 100° C. to 150° C. Also disclosed are resist compositions comprising the non-ionic PAG compounds and lithographic methods of forming resist patterns therefrom. Hereinafter, it should be understood that the PAGs are non-ionic prior to a lithographic exposure unless otherwise stated.

The PAGs are capable of forming an acid when exposed to radiation having a wavelength between 0 nm and 300 nm, including electron beam (E-beam) radiation, extreme ultraviolet radiation (EUV) having a wavelength of about 4-124 nm), soft x-ray, x-ray, γ-ray, and/or deep ultraviolet radiation (DUV) having a wavelength of about 125-250 nm (e.g., ArF excimer laser at 193 nm and KrF excimer laser at 248 nm). The PAGs can be relatively insensitive to DUV compared to EUV. As a result, EUV exposures of resists layers comprising the PAGs can produce lithographic patterns having fewer defects associated with out of band (OOB) radiation. In an embodiment, the lithographic process utilizes an ultraviolet wavelength of 13.5 nm (EUV) to expose a resist film comprising a disclosed PAG compound.

The PAG compounds are generally thermally stable up to at least 130° C. by thermogravimetric analysis (TGA). In an embodiment, the PAG compounds are thermally stable up to at least 140° C. by TGA.

The PAG compounds can be used singularly or in combination to form a resist composition. A resist composition can comprise a PAG compound as the sole photo-acid generating material.

The term "positive-tone development" means the exposed areas of the resist layer are selectively removed during development by a given developer. The exposed areas can become more soluble in a given developer (e.g., aqueous alkaline developer) by, for example, a non-crosslinking chemical reaction induced by the exposure that increases the polarity of the exposed areas, thereby increasing solubility of the exposed areas relative to non-exposed areas in a given polar developer.

The term "negative-tone development" means the non-exposed areas of the resist layer are selectively removed during development. In this instance, the exposed areas of the resist layer can become less soluble in a given developer compared to the non-exposed areas. For example, a cross-linking reaction or some other chemical change induced by the exposure can lower the solubility of the exposed areas relative to non-exposed areas in a given developer.

The term "positive-tone resist pattern" refers to the resist layer containing non-exposed resist that remains after positive-tone development. The examples further below illustrate formation of positive-tone resist patterns using the PAG compounds.

The term "negative-tone resist pattern" refers to the resist layer containing exposed resist that remains after negative tone development.

The PAG compounds can be used to form a positive-tone resist pattern or a negative tone resist pattern.

PAG Compounds

The PAG compounds comprise an aryl ketone group having a structure according to formula (1):

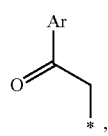

wherein

Ar is a monovalent radical comprising one or more aromatic rings.

Herein, a bond to an asterisk indicates the atomic center linked to the asterisk is covalently linked to another unspecified atomic center of the chemical structure. The asterisk represents the unspecified atomic center. In this instance, a methylene carbon is shown linked to an asterisk. The asterisk represents an oxygen of a sulfonate ester, as shown further below.

More specific aryl ketone groups have a structure according to formula (2):

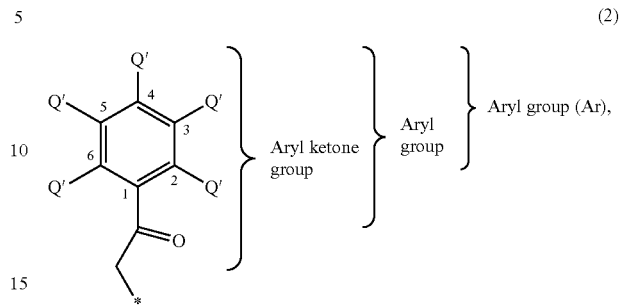

wherein carbons of the aromatic ring are numbered 1-6, each Q' is selected from the group consisting of hydrogen, halides, alkyl groups, fluoroalkyl groups, cycloalkyl groups, alkoxy groups, substituted and unsubstituted aryl groups, and substituted and unsubstituted aryloxy groups, and optionally, adjacent Q' groups complete a ring.

Exemplary non-limiting Q' groups include methyl, ethyl, isopropyl, t-butyl, hexyl, cyclohexyl, norbornyl, trifluoromethyl, trifluoroethyl, methoxy, ethoxy, propyloxy, butoxy, t-butoxy, phenyl, ortho-fluorophenyl, meta-fluorophenyl, para-fluorophenyl, pentafluorophenyl, and naphthyl.

Exemplary non-limiting aryl groups Ar include those of Scheme 1.

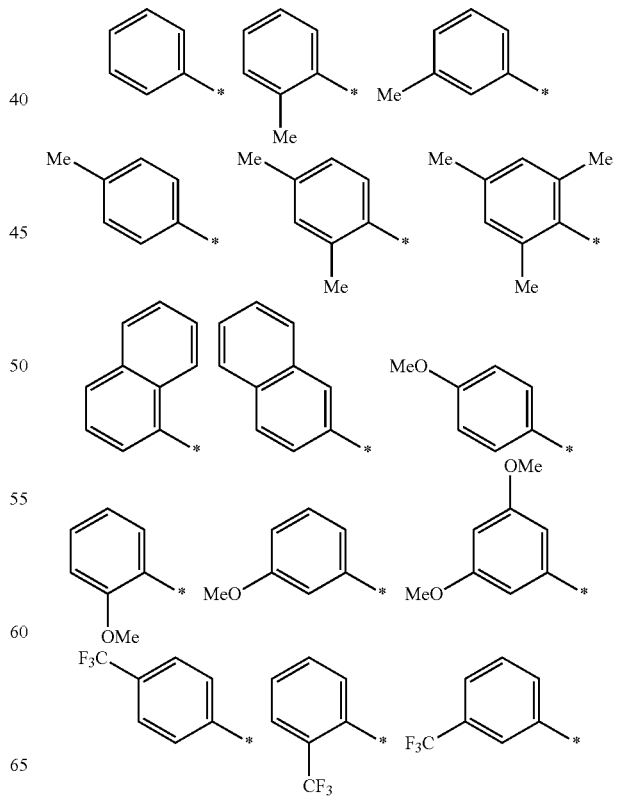

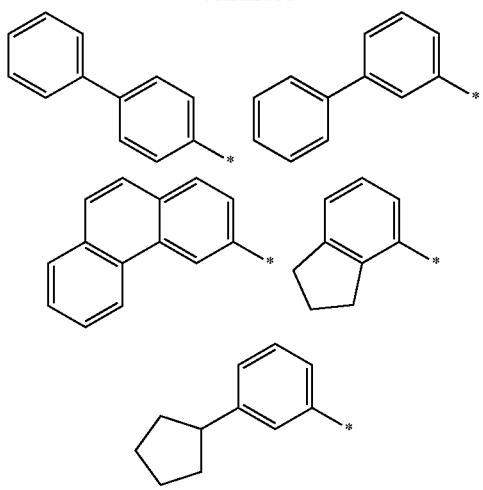
Exemplary non-limiting aroyl groups include those of Scheme 1A.
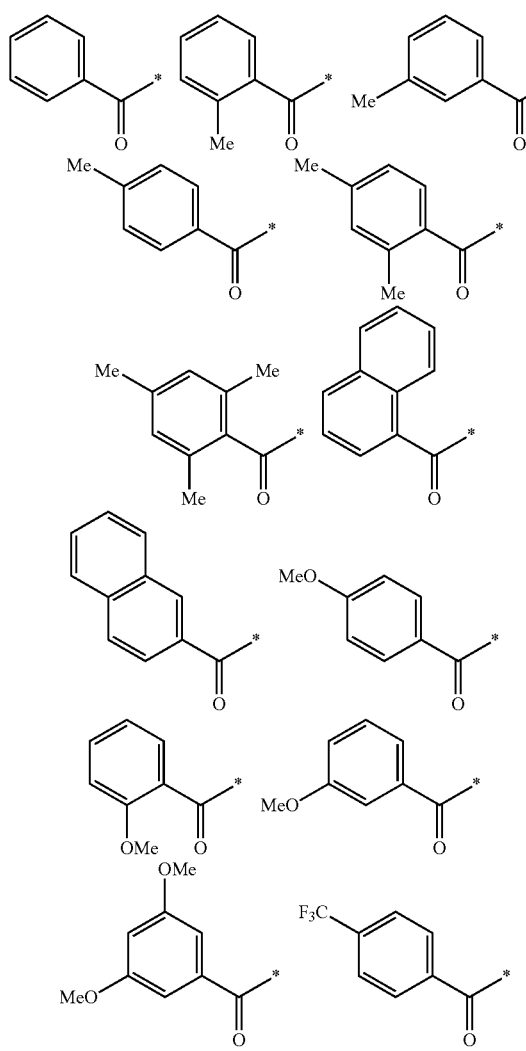
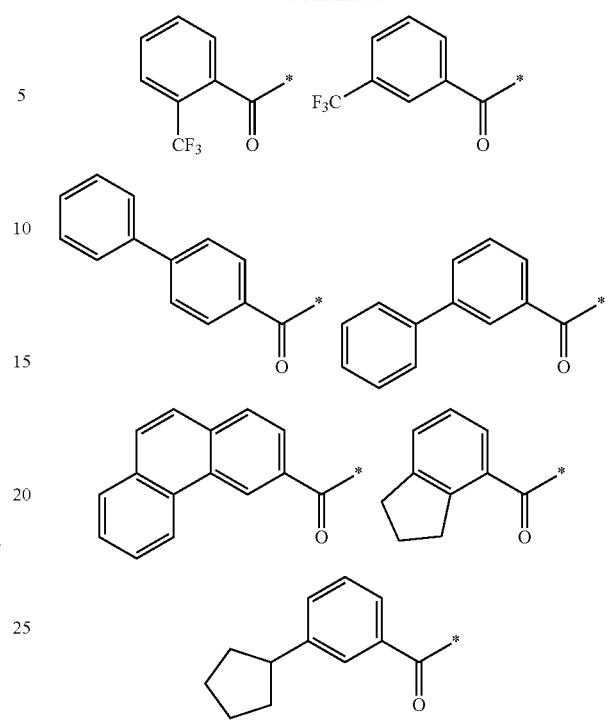
Exemplary non-limiting aryl ketone groups include those of Scheme 1B.
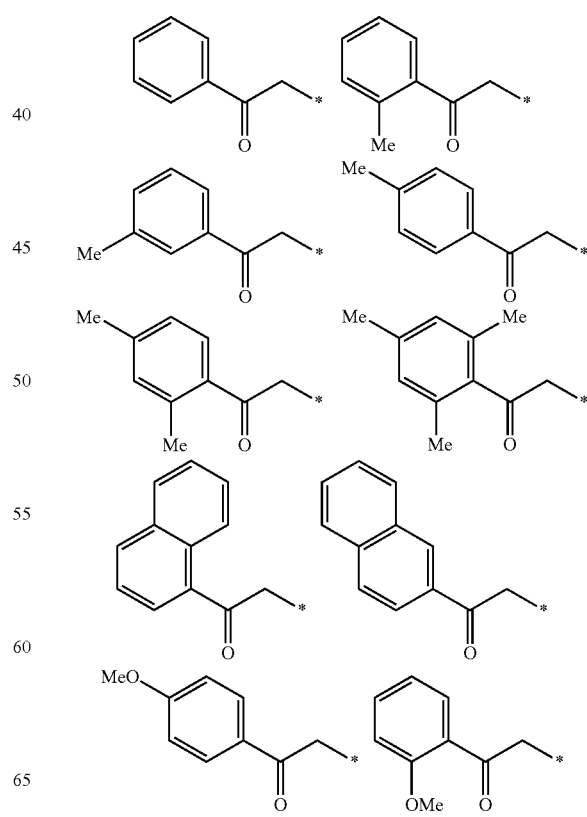

-continued

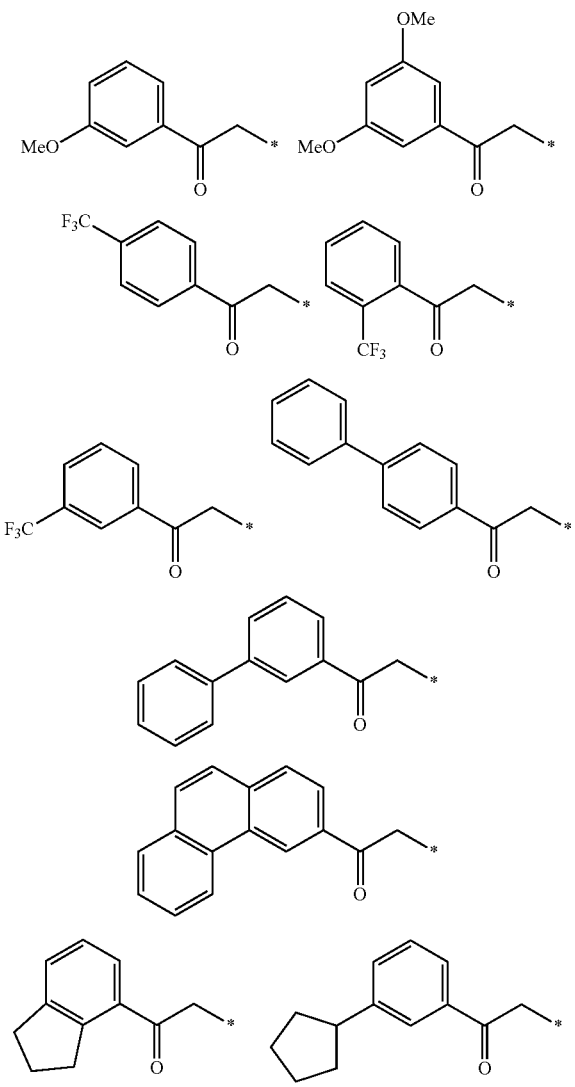

The PAG has a structure according to formula (3):

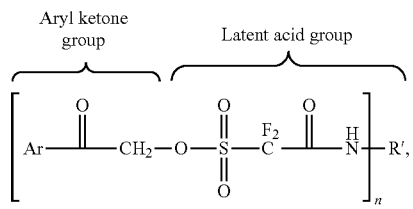

(3)

wherein n is a positive integer having a value of 1 to 4,

Ar is a monovalent aryl radical comprising one or more aromatic rings, and

R' is a hydrocarbon radical having a valency of n and comprising 2-20 carbons.

In an embodiment, n is 1 or 2. More specific PAG compounds have a structure according to formula (3A):

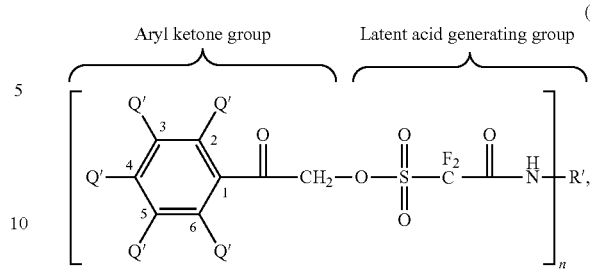

(3A)

wherein aromatic carbons of the aryl ketone group are numbered 1-6, n is a positive integer having a value of 1 to 4, each Q' is selected from the group consisting of hydrogen, halides, alkyl groups, fluoroalkyl groups, cycloalkyl groups, alkoxy groups, substituted and unsubstituted aryl groups, substituted and unsubstituted aryloxy groups, and a covalent bond which is linked to and completes a ring with an adjacent foregoing Q' group, and R' is a hydrocarbon radical having a valency of n and comprising 2-20 carbons.

Preferably, R' comprises 6-20 carbons.

Monovalent R' Groups (n=1)

Exemplary non-limiting monovalent R' groups include $C_6$-$C_{20}$ branched and unbranched alkyl groups (e.g., n-hexyl ($C_6H_{13}$), 3,3-dimethylbutan-2-yl, n-heptyl ($C_7H_{15}$), n-octyl ($C_8H_{17}$), octan-2-yl, 6-methylheptan-2-yl, n-nonyl ($C_9H_{19}$), nonan-2-yl, n-decyl ($C_{10}H_{21}$), n-undecyl ($C_{11}H_{23}$), n-dodecyl ($C_{12}H_{25}$), n-tridecyl ($C_{13}H_{27}$), n-tetradecyl ($C_{14}H_{29}$), n-pentadecyl ($C_{15}H_{31}$), n-hexadecyl ($C_{16}H_{33}$), n-heptadecyl ($C_{17}H_{35}$), n-octadecyl ($C_{18}H_{37}$), n-nonadecyl ($C_{19}H_{39}$), and n-icosyl ($C_{20}H_{41}$).

Other monovalent R' groups include substituted and unsubstituted, branched and unbranched, $C_6$-$C_{20}$ monocyclo-, bicyclo-, and tricyclo-alkanes such as those of Scheme Scheme 2

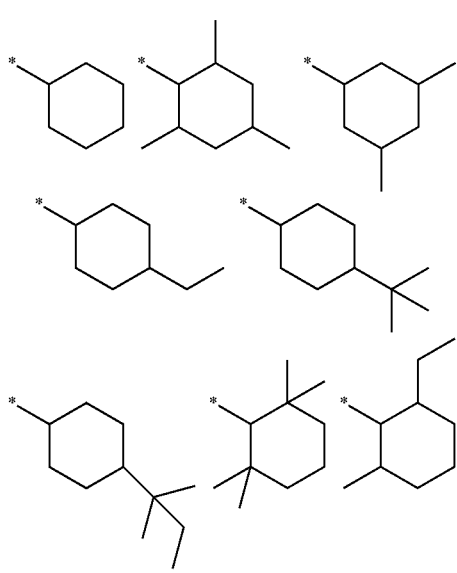

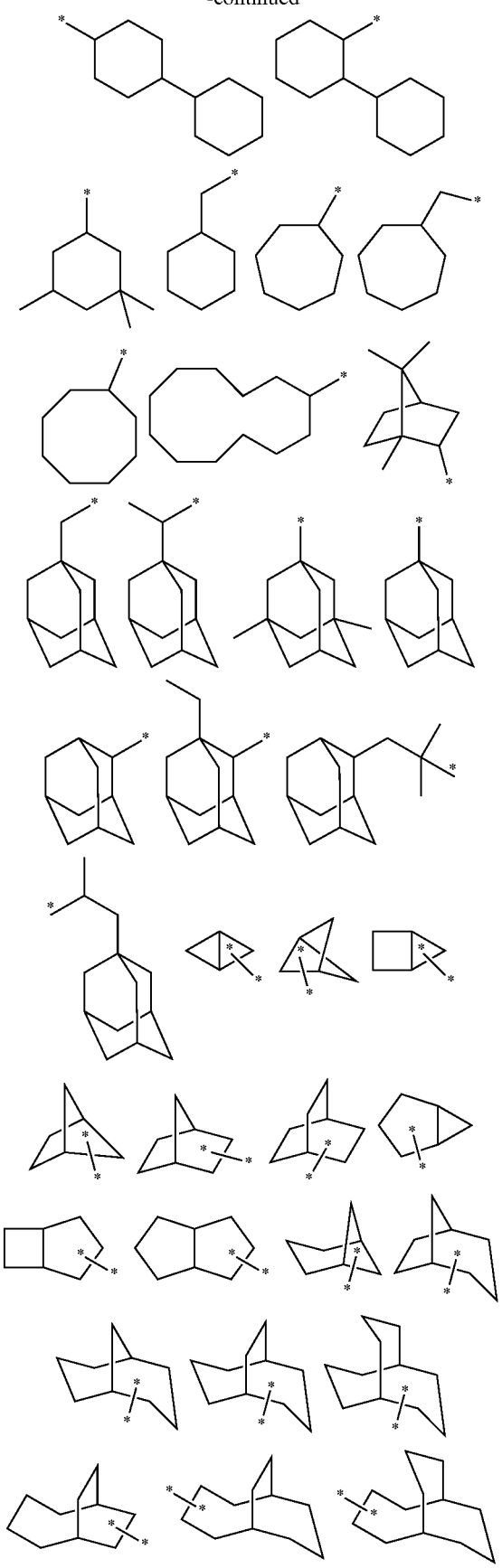

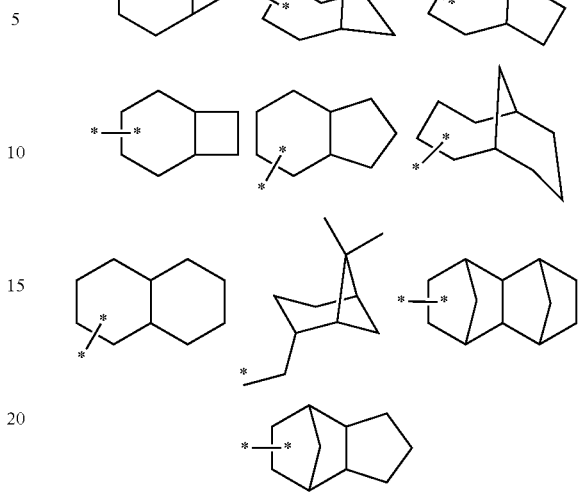

A bond with two asterisks crossing a bond means one end of the bond can be linked to any one of the carbons of the structure, and the other end of the bond is linked to the nitrogen of formula (3). As an example, the structure

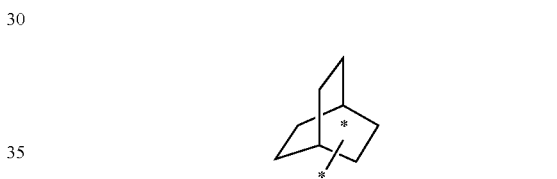

includes the following structures,

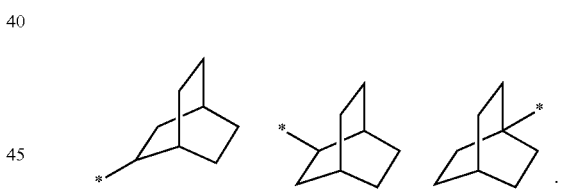

Other non-limiting monovalent R' groups include substituted and unsubstituted aromatic groups, such as those of Scheme 3.

Scheme 3

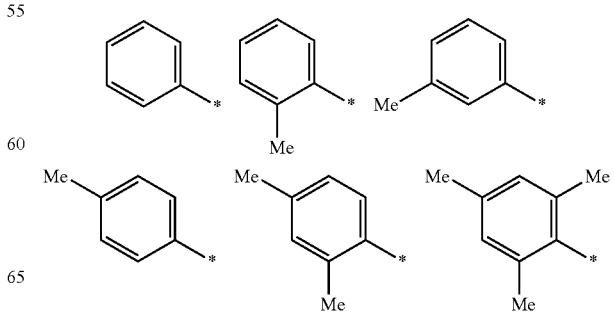

-continued

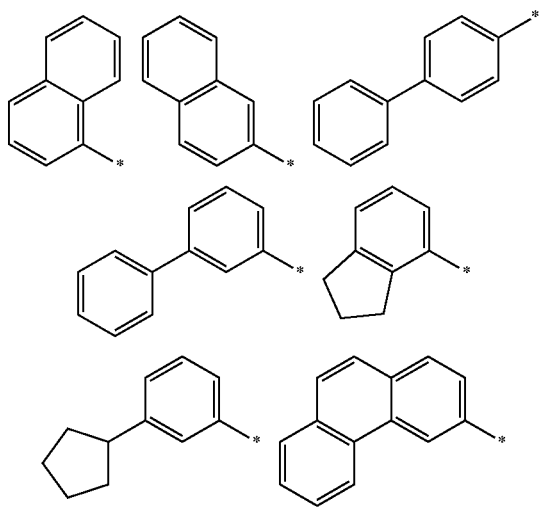

Divalent R' Groups (n=2)

Exemplary non-limiting divalent R' groups include $C_2$-$C_{20}$ branched and unbranched divalent hydrocarbylene groups (e.g., ethan-1,2-diyl (*—$CH_2CH_2$—*), propan-1,3-diyl (*—$CH_2CH_2CH_2$—*), propan-1,2-diyl (*—$CH(CH_3)CH_2$—*), butan-1,4-diyl (*—$CH_2(CH_2)_2CH_2$—*), butan-1,3-diyl (*—$CH_2CH_2CH(CH_3)$—*), pentan-1,5-diyl (*—$CH_2(CH_2)_3CH_2$—*), and hexan-1,6-diyl (*—$CH_2(CH_2)_4CH_2$—*), heptan-1,7-diyl (*—$CH_2(CH_2)_5CH_2$—*), octan-1,8-diyl (*—$CH_2(CH_2)_6CH_2$—*), and nonan-1,9-diyl (*—$CH_2(CH_2)_7CH_2$—*)).

Other non-limiting divalent R' groups include those of Scheme 4.

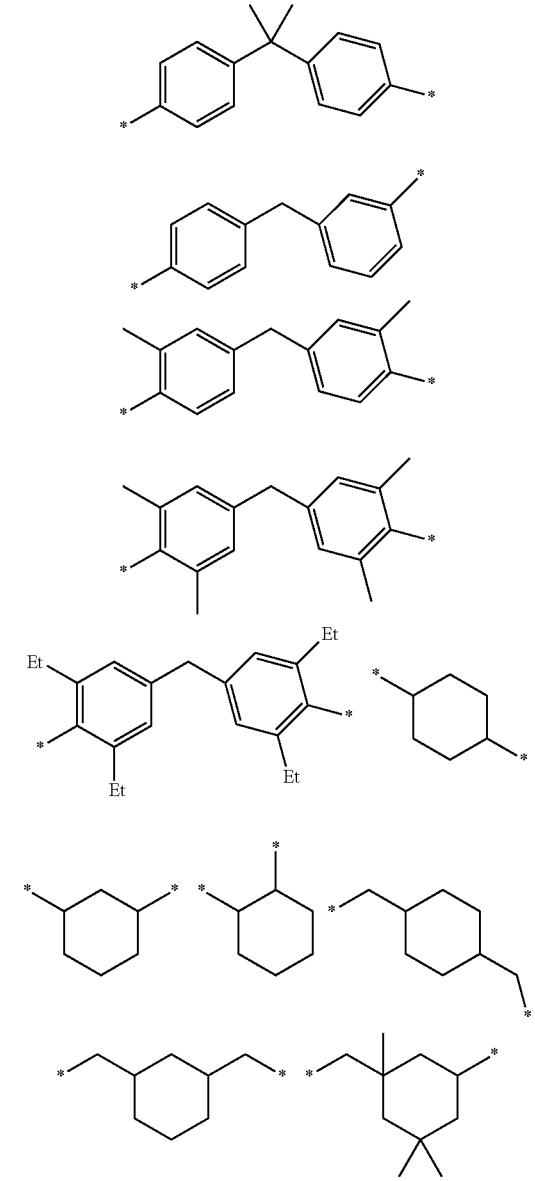

Scheme 4

In an embodiment, R' is 1,6-hexylene (*—$CH_2(CH_2)_4CH_2$—*).

The aryl ketone groups and/or R' groups can be stereospecific or non-stereospecific.

Trivalent R' Groups (n=3)

Exemplary non-limiting trivalent R' groups include branched and unbranched, cyclic and acyclic trivalent hydrocarbon groups having 3 to 2, such as the following:

Tetravalent R' Groups (n=4)

Exemplary non-limiting tetravalent R' groups include branched and unbranched, cyclic and acyclic tetravalent hydrocarbon groups having 3-20 carbons, such as the following:

Exemplary non-limiting PAG compounds include those of Scheme 5, where Ad is 1-adamantyl.

Scheme 5

The strong hydrogen bond forming amide functionality adjacent to R' limits diffusion of the photo-generated acid. The examples further below demonstrate that hydrolytic stability of the PAG can be increased by the introduction of electron donating and/or bulky groups in the ortho position (carbons 2 and/or 6) and para positions (carbon 4) of the aryl ketone group and/or by utilizing a polycyclic aryl ketone group in place of the monocyclic aryl ketone group.

Preparation of PAGs

The PAG compounds can be prepared according to the reaction sequences of Scheme 6.

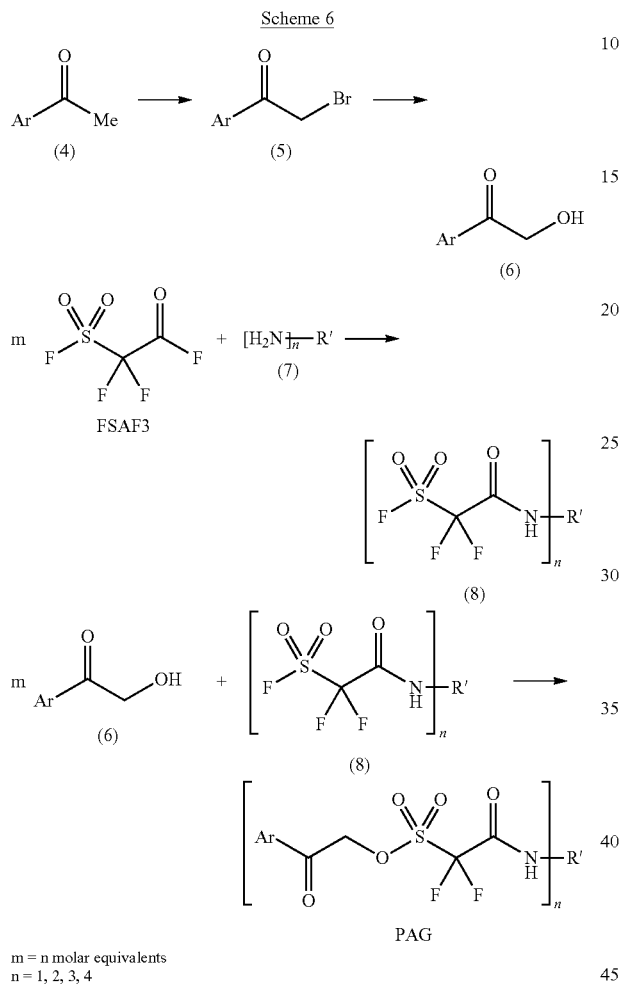

m = n molar equivalents
n = 1, 2, 3, 4

Ar and R' of Scheme 6 have the same meanings discussed further above.

In the first step, an aryl ketone of formula (4) is converted to an alpha-hydroxy aryl ketone of formula (6) in two steps. Treating an aryl ketone of formula (4) with N-bromosuccinimide (NBS) and p-toluenesulfonic acid monohydrate in acetonitrile forms an alpha-bromo aryl ketone of formula (5). Heating the alpha-bromo aryl ketone with sodium formate in methanol produces an alpha-hydroxy aryl ketone of formula (6). In a parallel reaction, 2-(fluorosulfonyl) difluoroacetyl fluoride (FSAF3) is treated with an amine $[H_2N]_n$—R' (n=1, 2, 3, or 4 of formula (7)), thereby forming a sulfonyl fluoride compound of formula (8). The molar equivalents of FSAF3 used in the reaction corresponds to n of formula (7). For example, 2 molar equivalents of FSAF3 are used per equivalent of a diamine of formula (7), where n=2. Under suitable conditions demonstrated by the examples below, the amine compound can preferentially react at the carboxylic acid halide site of the bis-acid halide FSAF3, forming the intermediate amide sulfonyl halide compound of formula (8). This reaction is preferably conducted at a temperature of about 0° C. The amide sulfonyl halide compound of formula (8) is then treated with the alpha-hydroxy aryl ketone of formula (6), forming the PAG compound.

Particularly preferred aryl ketone compounds of formula (4) include those of Scheme 7.

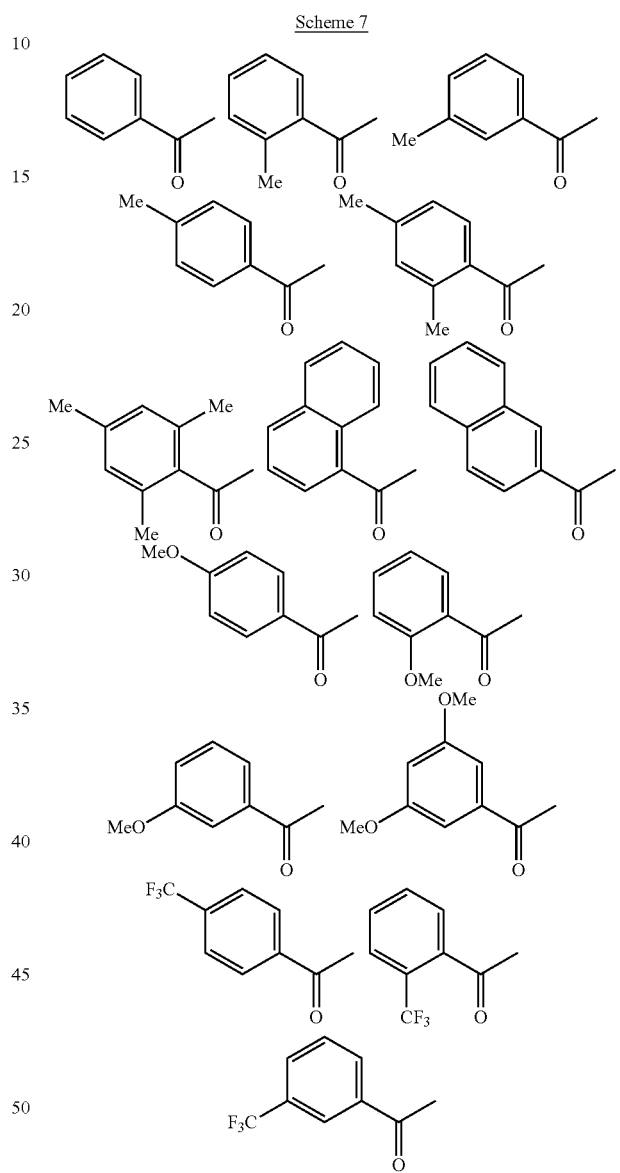

Non-limiting examples of amines of formula (7) include those of Scheme 8.

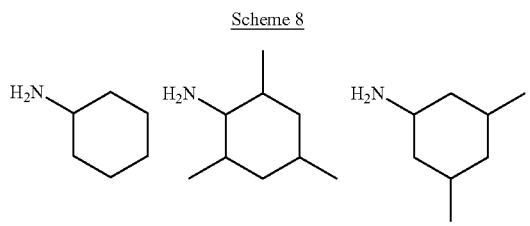

-continued
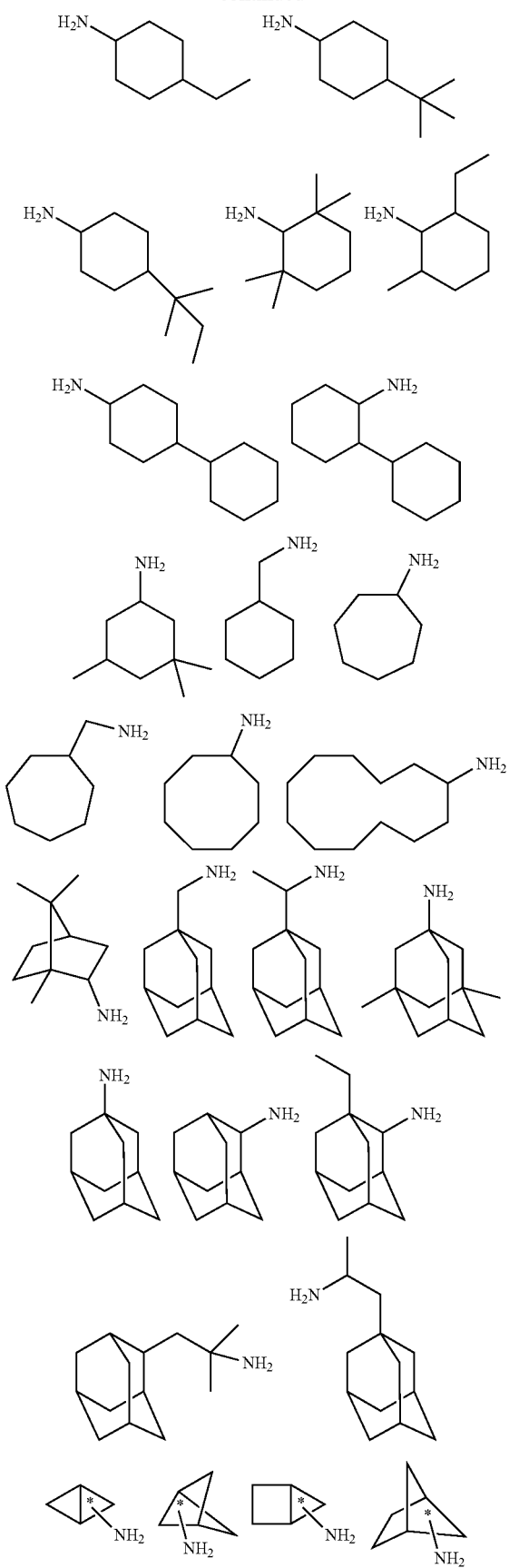
-continued
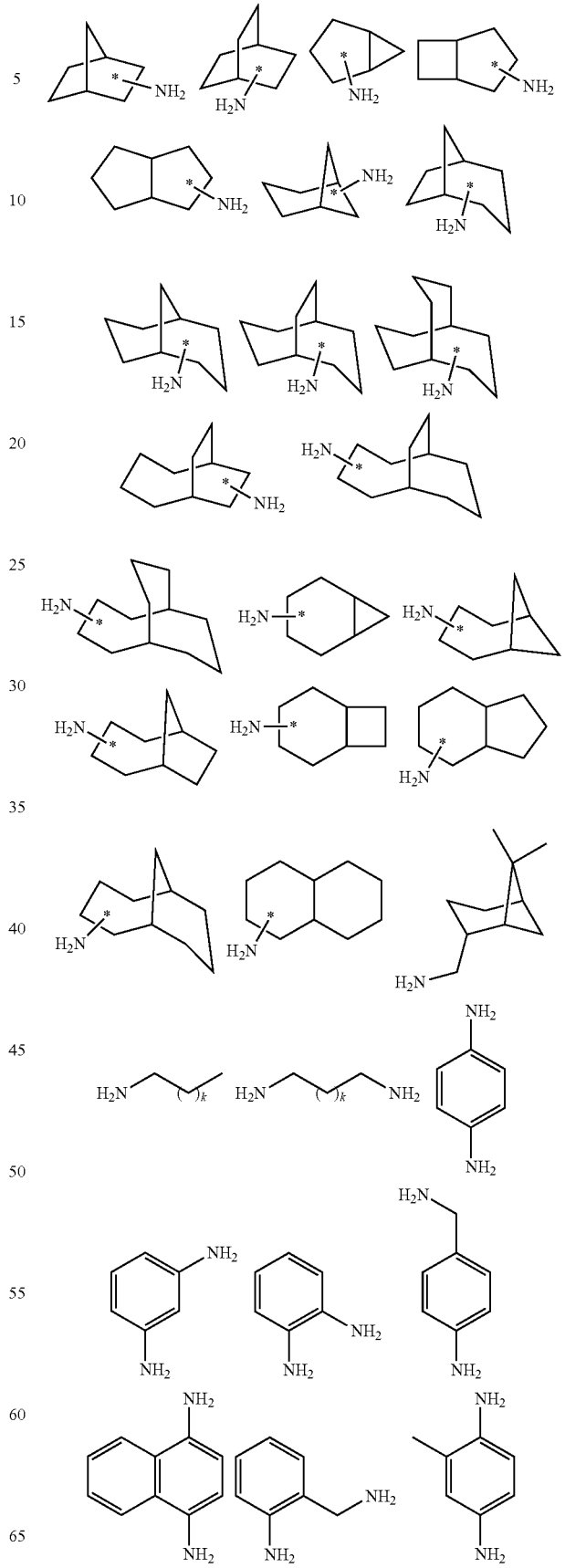

-continued

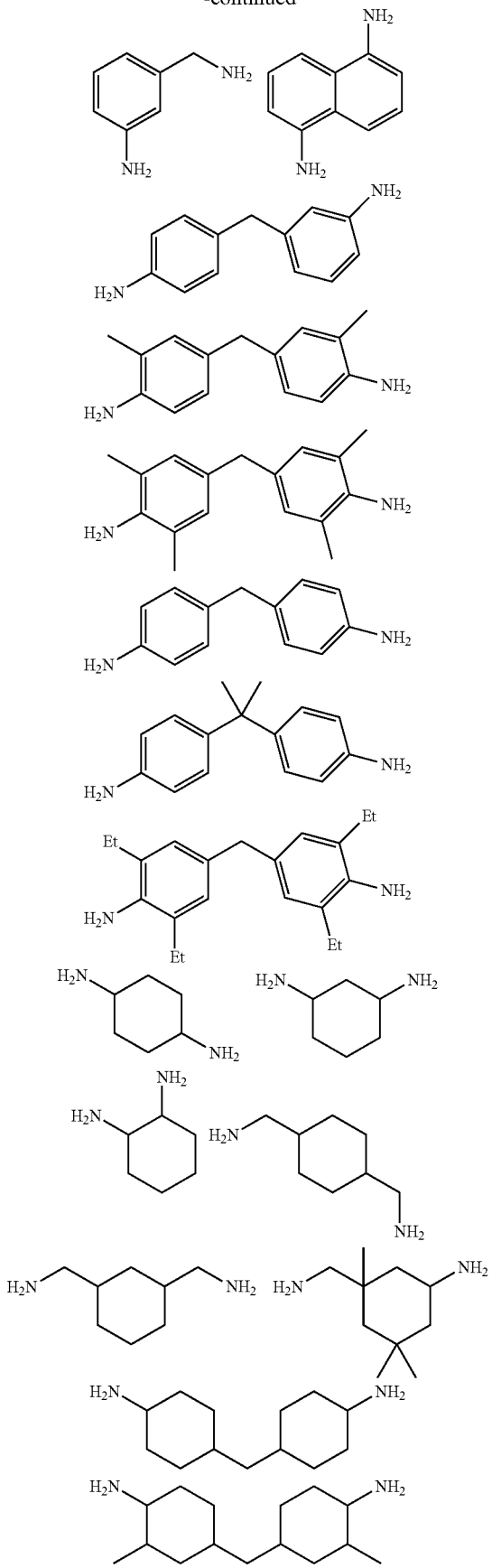
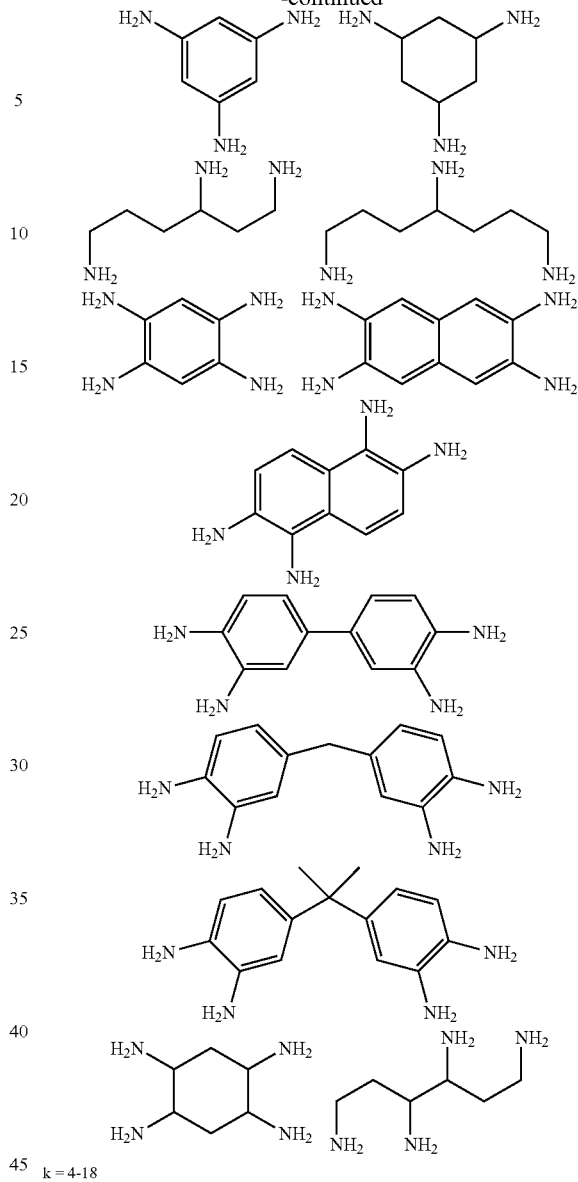

k = 4-18

In an embodiment, the amine is a compound selected from the group consisting of phenylamine, 1-adamantylamine, and 1,6-hexanediamine.

Non-limiting exemplary solvents for the above reactions include dichloromethane, chloroform, toluene, diethyl ether, carbon tetrachloride, 1,2-dichloroethane, tetrachloroethylene, chlorobenzene, dimethylformamide and acetonitrile. The solvents can be used singularly or in combination.

Resist Formulation

The PAG compound is used in a resist formulation (composition) in the form of a solution mixed with other components. When the PAG compound is used with a resin, the resin can be a positive tone resin or a negative tone resin. Non-limiting exemplary resins include polymers, molecular glasses, organometallic complexes, oligomers, and the like.

The resist composition can include not only a solvent but also various additives commonly used for resist compositions such as, for example, an auxiliary resin, a quencher, a dissolution inhibitor, a plasticizer, a stabilizer, a coloring agent, a surfactant, a viscosity improver, a leveling agent, an antifoaming agent, a compatibilizer, a primer, and/or an antioxidant. In the case of the negative resist composition, other additives such as a crosslinking agent and/or a basic compound can further be added. The additives can be used in addition to the following materials.

Resin

The resin can contain an acid-labile group so as to perform a positive resist function, or a cross-linking functionality so as to perform a negative resist function.

Examples of resins for a positive resist composition are those comprising a repeat unit having a pendant carboxyl group or acidic hydroxyl group protected by an acid-labile group on a side chain thereof, and a main chain portion derived from a polymerization of a vinyl polymerizable group, such as a repeat unit formed by polymerization of acrylic acid, methacrylic acid, α-trifloromethylacrylic acid, a vinyl group, an allyl group, and/or norbornene group.

Examples of the resin for the negative resist composition are those comprising a repeat unit having a cross-linking functionality on a side chain thereof such as, for example, hydroxyl groups, carboxyl groups, oxiranes (epoxides), oxetanes, blocked isocyanates, and a main chain portion resulting from a polymerization of a vinyl polymerizable group, such as a repeat unit formed by polymerization of acrylic acid, methacrylic acid, α-trifloromethylacrylic acid, vinyl group, allyl group, and/or norbornene group. The cross-linking functionalities can be present singularly or in combination.

The resin generally has a number average molecular weight of 1,000 to 1,000,000, preferably 2,000 to 500,000, as measured by gel permeation chromatography (GPC) If the number average molecular weight of the resin is less than 1,000, the resulting resist composition generally does not form a film with sufficient strength. If the number average molecular weight of the resin exceeds 1,000,00, the solubility of the resin in the solvent decreases, adversely affecting the uniformity of films formed with the resist composition. The molecular weight distribution (Mw/Mln, PDI) of the resin is preferably in the range of 1.01 to 3.00, most preferably 1.10 to 2.50.

Crosslinking Agents

Non-limiting exemplary cross-linking agents for a negative resist composition, include compounds formed by reacting an amino-containing compound (e.g., melamine, acetoguanarnine, benzoguanarnine, urea, ethylene urea, propylene urea, and glycoluril) with formaldehyde or a mixture of formaldehyde and lower alcohol, thereby substituting a hydrogen atom of the amino group with a hydroxymethyl group or a lower alkoxymethyl group. Herein, the cross-linking agents using melamine, urea, alkylene urea (e.g., ethylene urea, propylene urea, and the like) and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethymelamine, hexapropoxymethylmelamine and hexabutoxymethylmelamine. Hexamethoxymethyl melamine is preferred.

Examples of the urea-based cross-linking agents are bismethoxymethylurea, bisethoxymethylurea, bispropoxymethylurea and bisbutoxymethylurea. Bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimeth oxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, uri- and/or tetra-ethoxymethylated glycoluril, mono-, di-, tri- and/or tetra-propoxymethylated glycoluril and mono-, di-, tri- and/or tetra-butoxymethylated glycoluril.

The total amount of the cross-linking agent used is preferably 3 to 30 parts by mass, more preferably 3 to 25 parts by mass, most preferably 5 to 20 parts by mass, per 100 parts by mass of the resin of the resist composition. If the total amount of the cross-linking agent is less than 3 parts by mass of the resin, the resist composition is generally not capable of sufficient cross-linking to form a desirable resist pattern. The resist composition can exhibit poor storage stability and/or deteriorate in sensitivity with time if the total amount of the cross-linking agent exceeds 30 parts by mass of the resin.

Basic Compounds

The basic compound is preferably contained as an optional component in the resist composition so as to function as a quencher or to obtain improvements in resist pattern shape and post exposure stability.

Exemplary basic compounds include primary, secondary and tertiary aliphatic amines, aromatic amines, heterocyclic amines, nitrogen-containing compounds with hydroxyphenyl group, alcoholic nitrogen-containing compounds and amide derivatives. Other basic compounds include tetraalkylammonium hydroxides (e.g., tetraoctylammonium hydroxide). Secondary and tertiary aliphatic amines, aromatic amines and heterocyclic amines are preferred. The amine N—H group can optionally be protected by a tert-butyloxycarbonyl group (t-BOC group).

The aliphatic amines can be in the form of alkylamines or alkylalcohol amines each obtained by replacing at least one hydrogen atom of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethyl amine, triethylamine, tri-n-propy amine, tri-n-butylamine, tri-n-hexylamine, tri-n-pentylamine, tri-n-heptylamine, tri-n-octylamine, tri-n-nonylamine, tri-n-decanyl amine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethyaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoltuidine, heterocyclic amines such as 1,5-diazabicyclo[4.3.0]non-5-ene, 1,8-diazabicyclo[5.4.0] undec-7-ene, 1,4-diazabicyclo[2.2.2]octane, 4-dimethylaminopyridine, hexamethylenetetramine and 4,4-dimethylimidazoline, and hindered amines such as bis(1,2, 2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethyl ethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, and 2-phenyl benzimidazole. The basic compounds can be used singularly or in combination.

The amount of the basic compound used is generally 0.01 to 5 parts by mass per 100 parts by mass of the resin of the resist composition.

Acid Additives

In the case of the negative resist resin, an organic carboxylic acid, a phosphorus oxo acid, and/or a derivative thereof can be added as an optional component in order to prevent sensitivity deterioration caused by the addition of the basic compound and to obtain improvements in resist pattern shape and post exposure stability. This acid compound can be used singularly or in combination with the basic compound.

Exemplary organic carboxylic acid include malonic acid, citric acid, malic acid, succinic acid, benzoic acid and salicylic acid.

Examples of phosphorus oxo acid and its derivatives are: phosphoric acids and ester derivatives thereof such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Phosphonic acid is particularly preferred.

Solvents

There is no particular limitation on the organic solvent as long as the PAG compound can be dissolved in the organic solvent. Non-limiting organic solvents include: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; lactones such as gamma-butyrolactone; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used singularly or in combination.

Surfactants

Non-limiting surfactants for the resist composition include one or more fluorine- and/or silicon-based surfactants (i.e., fluorine-based surfactant, silicon-based surfactants, and surfactant containing both of fluorine and silicon atoms).

A resist composition comprising a surfactant is generally effective for use with an exposure light source of 250 nm or less wavelength, notably 220 nm or less wavelength and for pattern formation with a narrower pattern line width. It is possible to attain good sensitivity and resolution and obtain good resist patterning with less adhesion/development failures.

Other Acid Generators

The PAG compounds can be used singularly or in combination. The amount of the PAG compound used, including any second acid generating material, is generally in the range of 0.5 to 20 parts by mass per 100 parts by mass of the resist composition. If the amount of the acid generator is less than 0.5 parts by mass, the resist composition is generally not effective in forming good resist patterns. Moreover, storage stability of the resist composition decreases. The PAG compound is generally used in an amount of 1 to 100 parts by mass, preferably 1.0 to 100 parts by mass, more preferably 30 to 100 parts by mass, per 100 parts by mass of the total acid generator content.

Additive Resins

The resin composition can include one or more auxiliary resins in addition to the resin. There is no particular limitation placed on the auxiliary resin as long as the auxiliary resin can be dissolved in the solvent used and has compatibility with the other components of the resist composition. The auxiliary resin can function as an in-situ top coat, a plasticizer, a stabilizer, as a viscosity improver, a leveling agent, an antifoaming agent, a compatibilizer, and/or a primer.

Pattern Formation Method

Pattern formation using the resist composition can be performed by well-known lithographic processes. The process generally involves coating, prebaking, exposing to high-energy radiation (typically E-Beam, deep ultraviolet (DUV, e.g., 248 nm, 193 nm), or extreme ultraviolet (EUV, e.g., 13.5 nm), post exposure baking (PEB), and developing with alkaline developer. These steps are described in more detail below.

The term "substrate" refers to all underlying layers of a structure on which the resist layer is disposed. The term "disposed" refers to a layer in contact with a surface of another layer. "Disposing" or "applying" refer to forming a layer to be in contact with a surface of another layer, without limitation as to the method employed unless otherwise stated, providing the desirable properties of the disposed or applied layer are not adversely affected (e.g., uniformity and thickness). The term "casting" refers to forming a layer of a material by disposing a solution of the material dissolved in a solvent on a surface of another layer, and removing the solvent.

The substrate can have one or more layers arranged in a stack. The substrate, and more particularly the surface of the substrate, can comprise inorganic or organic materials such as metals, carbon, or polymers. The terms "surface" or "underlying surface" refer to the substrate surface on which the resist layer is disposed. More particularly, the substrate and/or surface of the substrate can comprise an inorganic material and/or organometallic material such as, for example, Si, SiGe, SiGeC, SiC, $SiO_2$, SiN, SiON, SiOC, TiN, WSi, BPSG, SOG, Ge alloys, GaAs, InAs, InP, as well as other III-V or II-VI compound semiconductors. The inorganic material and/or organometallic material can be doped, undoped or contain both doped and undoped regions therein. The substrate can also comprise a layered semiconductor such as Si/SiGe, or a semiconductor-on-insulator (SOI). In particular, the substrate can contain a Si-containing semiconductor material (i.e., a semiconductor material that includes Si) such as, for example, silicon dioxide, silicon nitride, and quartz. A more particular surface layer comprises Cr, CrO, CrON, MoSi, and the like.

In a multi-layered substrate, the layer directly below and in contact with the resist layer is the top-most layer of the substrate, also referred to as "the underlayer" to the resist layer. As non-limiting examples, the resist layer can be disposed on the surface of a silicon wafer or a metal foil, or more particularly on the surface of an anti-reflection layer (ARC) of a multi-layer substrate, where the ARC layer is the top-most layer of the substrate. In this example, the ARC layer is also the underlayer of the resist layer. In another example, the ARC layer has a polymer brush layer attached to the top surface. In this example, the polymer brush layer is also the underlayer of the resist layer.

It should be understood that in some cases (e.g., when forming dense, high resolution patterns) all of the resist layer can receive some dose of radiation exposure. "Non-exposed resist" refers to resist that has received an insufficient dose to switch the solubility of the resist in a given developer compared to the pre-exposed resist (including pre-exposed resist that has been treated with an optional bake and/or optional rinse). "Exposed resist" has received sufficient exposure to switch the solubility of the resist in a given developer compared to the pre-exposed resist.

"Polarity change" implies an altered chemical composition that affects relative solubility without crosslinking. The extent of the polarity change can be measured by comparing the solubility of the exposed resist and non-exposed resist in a given developer. "Inducing a polarity change" in the resist layer means subjecting the resist layer to a treatment involving exposure, a post-exposure bake (PEB) and/or an optional rinse that alters the chemical composition of the layer such that the treated resist has a different solubility compared to the pre-treated resist in a given developer (e.g., tetramethylammonium hydroxide (TMAH) solution in water).

Figure 1B:
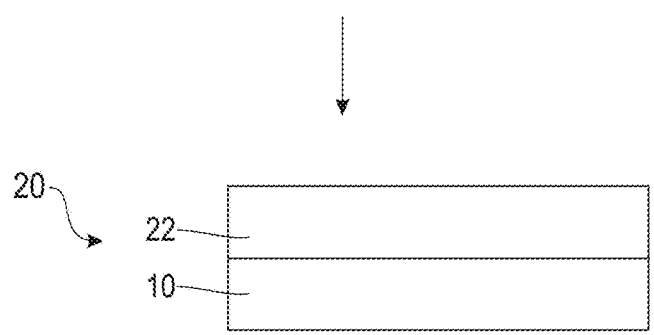

In the following example, the resin is capable of chemical amplification by formation of acid groups. In this instance, a positive-tone lithographic pattern can be formed, as illustrated in the schematic layer diagrams of FIGS. 1A to 1E. A resist composition comprising at least the resin, PAG compound, base quencher, and a solvent is disposed on surface 12 of substrate 10 (FIG. 1A) using any suitable coating technique (e.g., spin casting) followed by removal of the solvent to form resist layer 22 of structure 20 (FIG. 1B). Resist layer 22 comprises the solid components of the resist composition.

Resist layer 22 can be treated with an optional post-application bake (PAB) and/or an optional solvent rinse under suitable conditions of time and temperature before pattern-wise exposure. The optional PAB treatment is typically performed at a temperature of 50° C. to 250° C. for a period of 1 second to 10 minutes, more specifically 90° C. to 130° C. for about 1 minute. The PAB can be used to dry the film of excess solvent, remove unwanted or excess organic ligand, and/or partially crosslink the resist layer. The thermally treated dry film typically will have a thickness of 0.01 micrometers to 10 micrometers, depending on the subsequent radiation source and the desired application.

Figure 1C:
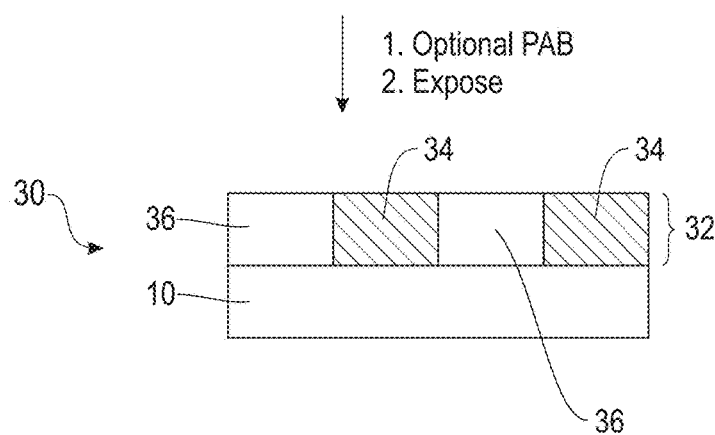

Then, the resist film is exposed to high-energy radiation, such as deep ultraviolet (DUV) light, excimer laser, x-ray, or extreme ultraviolet (EUV) light through a mask having a desired pattern. Pattern-wise exposure of resist layer 22 to high energy radiation results in exposed resist layer 32 of structure 30 (FIG. 1C). An ultraviolet light exposure dose is preferably on the order of about 1 $mJ/cm^2$ to about 200 $mJ/cm^2$, more preferably about 10 $mJ/cm^2$ to about 100 $mJ/cm^2$. The exposure can be performed by conventional lithography or by liquid immersion lithography. The liquid immersion exposure device uses a medium such as water and/or a fluorinated solvent between the mask and the resist film in the optical path, which causes less absorption of high energy radiation and enables more efficient fine processing in terms of numerical aperture and effective wavelength. In this case, a protective film that is insoluble in water can be applied beforehand to the resist film. Alternatively, a pattern can be written on the resist film directly with an electron beam (e-beam), in which case the exposure dose is generally in the range of about 1 $\mu C/cm^2$ to about 400 $\mu C/cm^2$.

Exposed resist layer 32 is composed of regions of exposed resist 34 and regions of non-exposed resist 36. Exposed resist layer 32 can be treated with an optional post-exposure bake (PEB) and/or an optional solvent rinse under suitable conditions of time and temperature before development. The optional PEB can be performed at a temperature of 50° C. to 150° C. for 1 second to 10 minutes, more specifically 80° C. to 140° C. for about 1 to 5 minutes.

The resist layer can be rinsed before or after the exposure, the PAB, and/or the PEB with a solvent (e.g., water, aqueous solutions, including water/alcohol mixtures, and organic solvents). Typically, a rinse is performed after the PAB. Rinses can be performed at or near room temperature (e.g., 10° C. to 50° C.) for a period of 1 second to 1 hour. The optional baking (PAB and/or PEB) treatments and/or optional rinsing treatments can enhance the solubility difference of the exposed resist compared to the non-exposed resist. A PAB and/or PEB can facilitate deprotection of acid sensitive protecting groups and/or elimination of reaction byproducts of the resist composition.

Figure 1D:
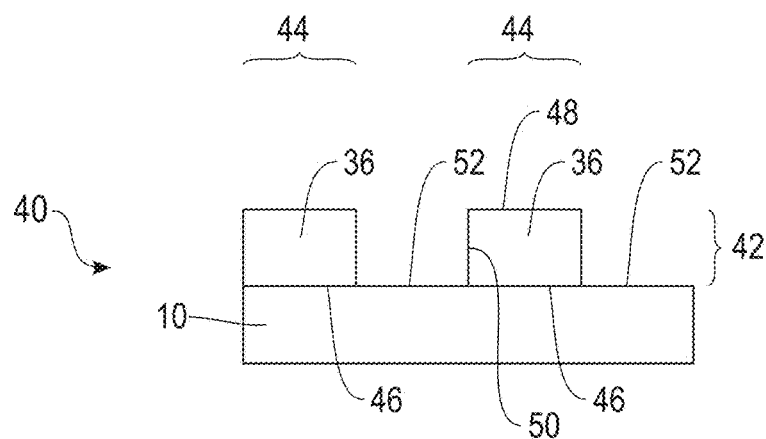

The exposed resist 34 and/or baked exposed resist 34 has greater solubility in an aqueous alkaline developer compared to non-exposed resist 36. Consequently, aqueous alkaline development of the exposed resist layer affords a positive-tone image by removing regions of exposed resist 34. Typically, the developer is 0.1 to 5 wt %, preferably 2 to 3 wt % aqueous solution of tetramethylammonium hydroxide (TMAH), and the development time is for 0.1 to 3 minutes, preferably 0.5 to 2 minutes. Development can be conducted by conventional techniques such as dip, puddle and spray techniques, resulting in layered structure 40 comprising patterned resist layer 42 (FIG. 1D). Patterned resist layer 42 is a topographical relief pattern comprising resist features 44 composed of non-exposed resist 36. Resist features 44 are disposed on surface 46 of substrate 10 and have top surface 48 and sidewall 50. Substrate surface 52 is in contact with air.

Optionally, the pre-developed resist layer and/or post-developed resist layer can be treated with water vapor and/or alcohol vapor either at room temperature or at elevated temperature on a time scale of 1 minute to 5 hours. Such a treatment after exposure and PEB can be conducted, for example, to promote deprotection of acid sensitive groups by acid-catalyzed hydrolysis (e.g. the deprotection of acetal-based protecting groups).

Figure 1E:
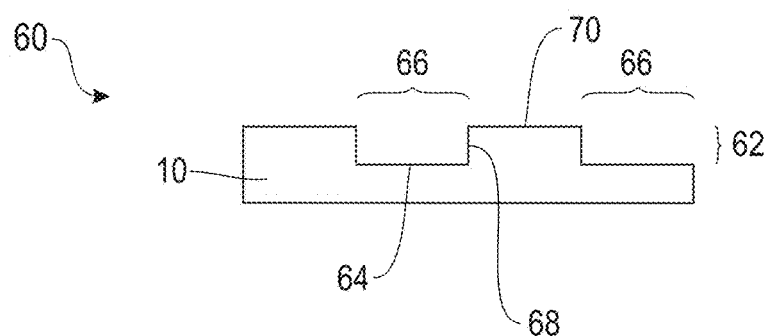

The topographical relief pattern of patterned resist layer 42 can be transferred to substrate 10 by known methods followed by removal of resist features 44 (e.g., oxygen ion etching), resulting in structure 60 (FIG. 1E). Structure 60 comprises a transferred topographical pattern 62 within substrate 10, whose features 66 comprise bottom surface 64, sidewall surface 68, and top surface 70 of substrate 10.

Developers

The aqueous alkaline developer for positive tone development can comprise any suitable base. Non-limiting exemplary bases include sodium hydroxide, potassium hydroxide, sodium carbonate, and various tetraalkyl ammonium hydroxides such as, for example, tetramethylammonium hydroxide (TMAH) and tetrabutylammonium hydroxide (TBAH). The aqueous alkaline developer can comprise one or more bases. Preferably, the aqueous alkaline developer comprises a tetraalkylammonium hydroxide, more preferably tetramethylammonium hydroxide. Preferably, the TMAH developer comprises 0.1 to 5 wt % tetramethylammonium hydroxide (TMAH) based on total weight of the developer solution in water.

The organic solvent developer for negative tone development can comprise any suitable organic solvent. Non-limiting exemplary organic solvents include ketone-based solvents, ester-based solvents, alcohol-based solvents, amide-based solvents, ether-based solvents, and hydrocarbon-based solvents. More specific organic solvent developers include methyl benzoate (MeB), ethyl 3-ethoxypropionate (EEP), 2-heptanone (MAK), 4-methyl-2-pentanone (4M2P), n-butyl acetate (NBA), amyl acetate, propylene glycol methyl ether acetate (PGMEA), anisole, acetophenone, and combinations thereof.

Post-Development Treatment

The patterned resist layer can also be given a post-development treatment, for example, to increase etch resistance. The post-development treatment can be photochemical, thermal, chemical, or a combination thereof. As an example, the patterned resist layer can be given a second exposure to a second radiation, thereby forming a treated patterned resist layer. The second exposure can be performed with a single wavelength of second radiation or a combination of suitable wavelengths (broad band) of second radiation, so long as the exposure is effective in inducing the desired response of the treated patterned resist layer. The second exposure treatment can be a flood exposure. The flood exposure can be a single conventional whole area exposure or a combination of conventional whole area exposures. The exposure treatment can also be a scanning exposure delivered by a digital writing device employing light emitting sources. The second exposure can be followed by a thermal treatment to chemically amplify the formation of chemical functional groups in the treated patterned resist layer. For example, the flood exposure can release an acid from previously unreacted photoacid generator (PAG) that upon subsequent heating catalyzes the deprotection of additional acid-sensitive carboxylic acid esters, aromatic acetals/ketals, and/or carbonates, thereby increasing the concentration of carboxylic acid and phenol groups in the treated patterned resist layer. With sufficient polarity change, the treated patterned resist layer can be rendered insoluble in either a low polarity solvent (e.g., anisole) or a more polar organic solvent, while retaining solubility in aqueous alkaline developer and/or a second organic solvent, without crosslinking the resist.

A post-development thermal treatment can further tailor the solvent compatibility, chemical structure of the resist material, and/or etch resistance of the patterned resist layer. The thermal treatment can be conducted at a temperature of 50° C. to 600° C., 50° C. to 300° C., or 50° C. to 200° C. for a period of 1 sec to 1 day.

A chemical treatment can include, for example, contacting the patterned resist layer with the vapors of a volatile Lewis acid, such as hydrochloric acid, sulfuric acid, nitric acid, or a sulfonic acid. In each type of treatment, the chemical alteration of the resist is preferentially uniformly distributed throughout the treated resist, not just at the surface. The post-development chemical treatment can cause a chemical change in the revealed surface of the substrate, producing (after removal of the resist features) a chemically patterned surface of the substrate.

Other post development treatments can include infiltration by ALD (aka SIS process) or chemical infiltration methods to infiltrate inorganic components into the resist and improve its etch properties.

Etching includes any common etching technique applied in the manufacture of semiconductor devices, for example, dry-etching such as plasma etching, or wet-etching using selective solvents. Typically, dry etching processes are employed for etching at sub-50 nm dimensions.

Figure 2:
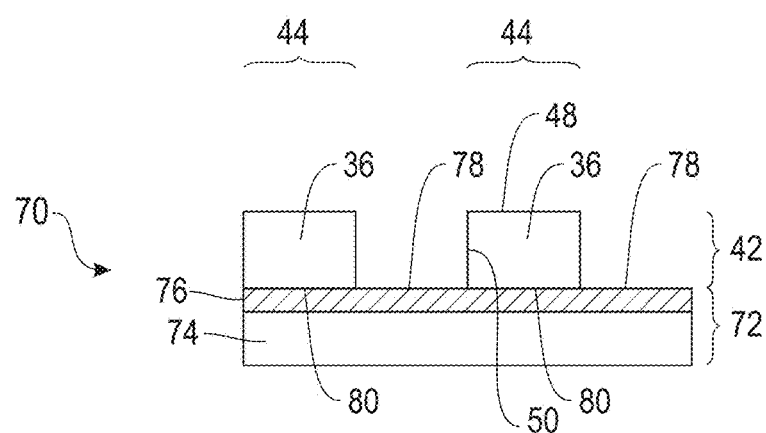
FIG. 2 is a schematic layer diagram of multi-layered structure that includes a topographical patterned layer comprising exposed resist composition disposed on a two layered substrate.

To further illustrate a multi-layered substrate, structure 40 of FIG. 1D is reproduced as structure 70 of FIG. 2, with the exception that substrate 72 of FIG. 2 has two layers, a bottom layer 74 and an intermediate layer 76. Bottom layer 74 of substrate 72 can be, for example, a silicon wafer. Intermediate layer 76 can be, for example, an ARC layer. In this example, surface 78 is a surface of the ARC layer in contact with air, and resist features 44 are disposed on ARC surface 80.

The following examples demonstrate the preparation of the PAG compounds, resist compositions thereof, and resist patterns formed therefrom. The resist formulations were not optimized.

EXAMPLES

Commercially available materials used in the following examples are listed in Table 1.

TABLE 1

| ABRE-VIATION | DESCRIPTION | SUPPLIER |
|---|---|---|
| MF-26A | 2.3 Wt % Aqeous Tetramethyl Ammonium Hydroxide Solution (TMAH) | FUJIFILM |
| Quencher 1 | 2-Phenyl Benzimidazole | Sigma-Aldrich |
| FSAF3 | 2-(Fluorosulfonyl)Difluoroacetyl Fluoride | Synquest |
| | 2-Hydroxyacetophenone | Sigma-Aldrich |
| | Aniline | Sigma-Aldrich |
| | 1-Adamantylamine | Sigma-Aldrich |
| | 4-(Chlorosulfonyl)Benzoic Acid | Sigma-Aldrich |
| | 2,3,4,5,6-Pentafluorobenzenesulfonyl Chloride | Sigma-Aldrich |
| | Benzoin | Sigma-Aldrich |
| | 2,3,5,6-Tetrafluoro-4-Sulfobenzoic Acid | TCI |
| | 4,4'-Biphenylsulfonyl Chloride | TCI |
| | Hexamethylenediamine | Sigma-Aldrich |
| | N-Bromosuccinimide | Sigma-Aldrich |
| | 2-Bromo-4'-Methoxyacetophenone | Sigma-Aldrich |
| | 4'-Trifluoromethylacetophenone | Sigma-Aldrich |
| | 2'-Methylacetophenone | Sigma-Aldrich |
| | 2'-Methoxyacetophenone | Sigma-Aldrich |
| | 2'-Trifluoromethylacetophenone | Sigma-Aldrich |
| | 1-Acetonaphthone | Sigma-Aldrich |
| | 2-Bromopropiophenone | Sigma-Aldrich |
| | (Diacetoxyiodo)Benzene | Sigma-Aldrich |

TABLE 1-continued

| ABRE-VIATION | DESCRIPTION | SUPPLIER |
|---|---|---|
| NBHFAMA | 2-{[5-(1',1',1'-Trifluoro-2'-Trifluoro-methyl-2'-Hydroxy)Propyl]Norbornyl]} Methacrylate | Central Glass |
| ECPMA | 1-Ethylcyclopentyl Methacrylate | JSR |

Herein, Mn is the number average molecular weight, Mw is the weight average molecular weight, and MW is the molecular weight of one molecule.

The following examples are intended to provide those of ordinary skill in the art with a complete disclosure and description of how to prepare and use the compositions disclosed and claimed herein. Unless indicated otherwise, parts are parts by weight, temperature is in degrees centigrade (° C.) and pressure is at or near atmospheric. Additionally, all starting materials including the co-monomers other than the PAG monomers were obtained commercially or were synthesized using known procedures.

Where appropriate, the following techniques and equipment were utilized in the examples below: $^1$H NMR and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using Cr(acac)$_3$ as a relaxation agent on an Avance 400 spectrometer. Thermo-gravimetric analysis (TGA) was performed at a heating rate of 5° C./minute in N$_2$ on a TA Instrument Hi-Res TGA 2950 Thermogravimetric Analyzer. Differential scanning calorimetry (DSC) was performed at a heating rate of 10° C./minute on a TA Instruments DSC 2920 modulated differential scanning calorimeter. Number average and weight average molecular weights were measured in tetrahydrofuran (THF) or dimethylformamide (DMF) on a Waters Model 150 chromatograph relative to polystyrene standards.

In the structures that follow, Ph=phenyl, and Ad=1-Adamantyl.

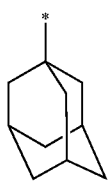

1-Adamantyl

Resist film layers containing the PAGs were exposed using a 193 nm interferometric tool (IBM Designed NEMO) or a 0.3 NA EUV micro-exposure tool (EUV-MET) at Lawrence-Berkeley National laboratory.

Synthesis of Starting Materials for PAG

Amide-sulfonyl fluoride compounds of Examples 1-3 were prepared using the general reaction shown below.

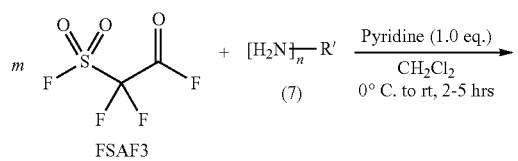

FSAF3

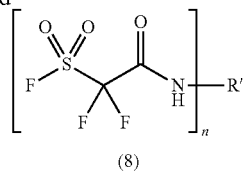

(8)

m = n molar equivalents
n = 1, 2, 3, 4

Example 1. Preparation of SM-1: 1,1-difluoro-2-oxo-2-(phenylamino)ethane-1-sulfonyl fluoride

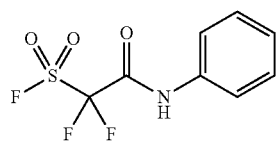

SM-1

A 100 mL flask was charged with CH$_2$Cl$_2$ (10 mL) under nitrogen stream at 0° C. and then 2-(fluorosulfonyl)difluoroacetyl fluoride (4.00 g, 22.6 mmol, 1.2 eq.) was added and the mixture was stirred for 5 minutes at 0° C. A CH$_2$Cl$_2$ (8 mL) solution of aniline (1.71 g, 18.4 mmol, 1.0 eq.) and pyridine (1.45 g, 18.4 mmol, 1.0 eq.) was added drop wise to the mixture over 10 minutes and subsequently the mixture was stirred for an hour at 0° C. In addition, the mixture was allowed to warm to RT and stirred for 4 hours at RT. CH$_2$Cl$_2$ (36 mL) and 1N HCl (18 mL) were added to the final reaction mixture and then the lower layer was separated and washed with 1N HCl (18 mL×2) and brine (18 mL×2). The solution was dried over anhydrous MgSO$_4$ and filtrated and then CH$_2$Cl$_2$ was removed in an evaporator. The target compound as pale yellow solid (4.53 g) in 97.3% yield was obtained. $^1$H-NMR (CDCl$_3$, delta in ppm): delta 7.35 (tt, J=7.4, 1.1 Hz, 1H), 7.45 (dd, J=7.6, 8.4 Hz, 2H), 7.61 (dd, J=1.0, 8.6 Hz, 2H), 8.08 (brs, 1H). $^{19}$F-NMR (CDCl$_3$δ in ppm, standard: C$_6$F$_6$=−162.2 ppm): 41.25 (t, J=4.7 Hz, 1F), −105.32 (d, J=4.2 Hz, 2F).

Example 2. Preparation of SM-2: 1,1-Difluoro-2-oxo-2-(1-adamntylamino) ethanesulfonyl fluoride

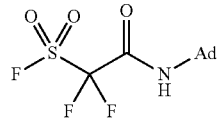

SM-2

A 100 mL flask was charged with CH$_2$Cl$_2$ (20 mL) under nitrogen stream at 0° C. and then 2-(fluorosulfonyl)difluoroacetyl fluoride (8.49 g, 47.1 mmol, 1.2 eq.) was added and the mixture was stirred for 10 minutes at 0° C. A CH$_2$Cl$_2$ (20 mL) solution of 1-adamantylamine (5.94 g, 39.3 mmol, 1.0 eq.) and Pyridine (3.10 g, 39.3 mmol, 1.0 eq.) was added drop wise to the mixture over 15 minutes and subsequently the mixture was stirred for 4 hours at 0° C. to room temperature. CH$_2$Cl$_2$ (40 mL) and 1N HCl (40 mL) were added to the final reaction mixture and then the lower layer was separated and washed with 1N HCl (40 mL) and brine (40 mL). The solution was dried over anhydrous MgSO$_4$ and filtrated and then CH$_2$Cl$_2$ was removed in an evaporator. The target compound as yellow solid (11.77 g) in 96.2% yield was obtained. $^1$H-NMR (CDCl$_3$), delta (ppm): 1.56 (brs, 6H), 2.03 (brs, 6H), 2.13 (brs, 3H), 6.02 (brs, 1H), $^{19}$F-NMR (CDCl$_3$), delta in ppm, standard: C$_6$F$_6$=−162.2 ppm): 40.55 (t, J=4.8 Hz, 1F), −105.02 (d, J=4.9 Hz, 2F).

Example 3. Preparation of SM-3: 2,2'-(hexane-1,6-diylbis(azanediyl)bis(1,1-difluoro-2-oxoethane-1-sulfonyl Fluoride

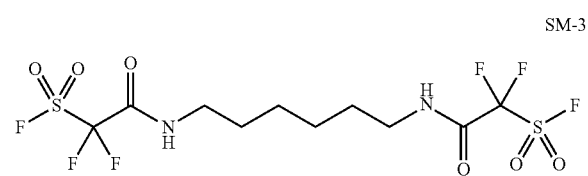 [SMILES: O=C(NCCCCCCNC(=O)C(F)(F)S(=O)(=O)F)C(F)(F)S(=O)(=O)F]

SM-3

A 100 mL flask was charged with CH$_2$Cl$_2$ (10 mL) under nitrogen stream at 0° C. and then 2-(Fluorosulfonyl)difluoroacetyl fluoride (5.82 g, 32.3 mmol, 2.5 eq.) was added and the mixture was stirred for 10 minutes at 0° C. A CH$_2$Cl$_2$ (15 mL) solution of hexamethylenediamine (1.50 g, 12.9 mmol, 1.0 eq.) and Pyridine (2.04 g, 25.8 mmol, 2.0 eq.) was added drop wise to the mixture over 10 minutes and the mixture was allowed to warm to RT and stirred for an hour at RT. Et$_2$O (100 mL) and 1N HCl (20 mL) were added to the final reaction mixture and then the upper layer was separated and washed with 1N HCl (20 mL) and brine (20 mL×2). The solution was dried over anhydrous MgSO$_4$ and filtrated and then solvents were removed in an evaporator. The crude material was purified by recrystallization (hexane/Et$_2$O×3). The target compound as white solid (3.88 g) in 68.9% yield was obtained. $^1$H-NMR (d-Acetone), delta (ppm): 1.37-1.41 (m, 4H), 1.60-1.64 (m, 4H), 3.41 (q, J=6.6 Hz, 4H), 8.97 (brs, 2H). $^{19}$F-NMR (d-Acetone), delta in ppm, standard: C$_6$F$_6$=−162.2 ppm: 41.51 (dd, J=4.7, 5.1 Hz, 2F), −102.03 (d, J=4.9 Hz, 2F), −102.09 (d, J=4.7 Hz, 2F).

Synthesis of Alpha-Hydroxy Aryl Ketones

Alpha-hydroxy ketone compounds of Examples 4-10 were prepared starting from an aryl ketone or an alpha-halo aryl ketone using the general reaction conditions shown below.

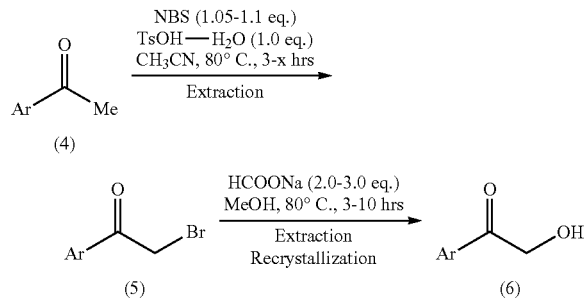

Example 4. Preparation of SM-4: 2-Hydroxy-4'-methoxyacetophenone

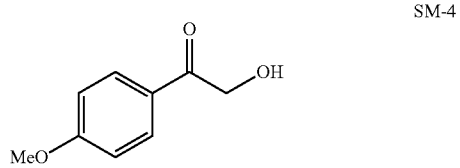 [SMILES: COc1ccc(C(=O)CO)cc1]

SM-4

A 100 mL flask was charged with 2-Bromo-4'-methoxyacetophenone (6.30 g, 27.5 mmol, 1.0 eq.) and MeOH (55 mL) under nitrogen stream and then HCOONa (5.61 g, 82.5 mmol, 3.0 eq.) was added. The mixture was stirred for 3 hours at 80° C. The mixture was then allowed to cool to room temperature and stirred for 15 hours. The remaining solid (HCOONa) was filtrated off and the filtrate was concentrated in an evaporator and then CH$_2$Cl$_2$ (100 mL) and H$_2$O (50 mL) were added. The lower layer was separated and washed with H$_2$O (50 mL) twice and then brine (50 ml). The solution was dried over anhydrous MgSO$_4$ and filtrated and then solvents were removed in an evaporator. The crude material was purified by recrystallization (hexane/CH$_2$Cl$_2$, 40° C. to 0° C.) to obtain the target compound as white solid (3.65 g) in 79.9% yield. $^1$H-NMR (CDCl$_3$), delta (ppm): 3.60 (t, J=4.6 Hz, 1H), 3.91 (s, 3H), 4.85 (d, J=4.6 Hz, 2H), 6.99 (d, J=8.9 Hz, 2H), 7.93 (d, J=8.9 Hz, 2H).

Example 5. Preparation of SM-5: 2-Hydroxy-4'-trifluoromethylacetophenone

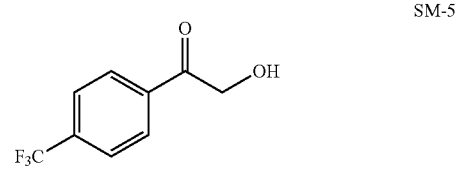 [SMILES: O=C(CO)c1ccc(C(F)(F)F)cc1]

SM-5

Step A. A 200 mL flask was charged with 4'-trifluoromethylacetophenone (9.41 g, 50 mmol), N-bromosuccinimide (9.79 g, 55 mmol, 1.1 eq.), p-toluenesulfonic acid (10.46 g, 55 mmol, 1.1 eq.) and MeCN (100 mL) under nitrogen stream and the mixture was stirred for 4 hours at 80° C. The mixture was allowed to cool to room temperature and then MeCN was removed in an evaporator. CHCl$_3$ (150 mL) and H$_2$O (50 mL) were added to the residue and the lower layer was separated and then washed with saturated aqueous NaHCO$_3$ (50 mL) twice and brine (50 mL). The solution was dried over anhydrous MgSO$_4$ and filtrated. The solvents were removed in an evaporator and a white solid (13.27 g) in 99.4% yield was obtained. This was identified as 2-Bromo-4'-trifluoromethylacetophenone contaminated with some dibromo compound. $^1$H-NMR (CDCl$_3$), delta (ppm): 4.48 (s, 2H), 7.81 (d, J=8.2 Hz, 2H), 8.13 (d, J=8.2 Hz, 2H), $^{19}$F-NMR (CDCl$_3$), delta (ppm), standard: C$_6$F$_6$=−162.2 ppm: −63.77 (s, 3F)

Step B. A 200 mL flask was charged with the crude of 2-Bromo-4'-trifluoromethylacetophenone from Step A (13.27 g, 50 mmol, 1.0 eq.) and MeOH (100 mL) under nitrogen stream and then HCOONa (10.20 g, 150 mmol, 3.0 eq.) were added. The mixture was stirred for 6 hours at 80°

C. The mixture was allowed to cool to room temperature and the remaining solid (HCOONa) was filtrated and then filtrate was concentrated in an evaporator. CHCl₃ (150 mL) was added to the residue and the precipitated solid was filtered off and the filtrate was washed with CHCl₃ (50 mL). H₂O (50 mL) was added to the filtrate and the lower layer was separated and washed with 1N HCl (50 mL) and brine (50 ml) twice. The solution was dried over anhydrous MgSO₄ and filtered. The solvents were removed in an evaporator. The crude material obtained was purified by recrystallization (hexane/AcOEt, 60° C. to 0° C.) to obtain the target compound as white solid (4.57 g) in 44.8% yield. ¹H-NMR (CDCl₃), delta (ppm): 3.43 (brs, 1H), 4.94 (s, 2H), 8.2 (d, J=8.2 Hz, 2H), 8.07 (d, J=8.1 Hz, 2H), ¹⁹F-NMR (CDCl₃), delta in ppm, standard: C₆F₆=−162.2 ppm: −63.81 (s, 3F).

Example 6. Preparation of SM-6:
2-Hydroxy-2'-methylacetophenone

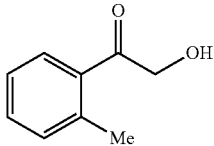

SM-6

Step A. A 200 mL flask was charged with 2'-methylacetophenone (6.71 g, 50 mmol), N-bromosuccinimide (9.34 g, 52.5 mmol, 1.05 eq.), p-toluenesulfonic acid (9.99 g, 52.5 mmol, 1.05 eq.) and MeCN (100 mL) under nitrogen stream and the mixture was stirred for 3 hours at 80° C. The mixture was allowed to cool to room temperature and then MeCN was removed in an evaporator. CHCl₃ (100 mL) and H₂O (50 mL) were added to a residue and the lower layer was separated and then washed with saturated aqueous NaHCO₃ (50 mL) twice and brine (50 mL). The solution was dried over anhydrous MgSO₄ and filtered. Solvents were removed in an evaporator and the crude product as an orange oil (11.01 g) was obtained in >99.9% yield. This product was identified as 2-Bromo-2'-methylacetophenone contaminated with some dibromo compound. ¹H-NMR (CDCl₃), delta (ppm): 2.51 (s, 3H), 4.41 (s, 2H), 7.24-7.30 (m, 2H), 7.41 (dt, J=1.3, 7.5 Hz, 1H), 7.60-7.70 (m, 1H)

Step B. A 200 mL flask was charged with the crude 2-Bromo-2'-methylacetophenone obtained in Step A (11.01 g, 50 mmol, 1.0 eq.) and MeOH (100 mL) under nitrogen stream, and then HCOONa (10.20 g, 150 mmol, 3.0 eq.) was added. The mixture was stirred for 4 hours at 80° C. The mixture was allowed to cool to room temperature and the remaining solid (HCOONa) was filtrated and the filtrate was concentrated in an evaporator. CHCl₃ (150 mL) was added to the residue and the precipitated solid was filtered and the solid was washed with CHCl₃ (50 mL). H₂O (50 mL) were added to the combined filtrate and the lower layer was separated and washed with H₂O (50 mL) twice and brine (50 ml) twice. The solution was dried over anhydrous MgSO₄ and filtrated and then solvents were removed in an evaporator. The crude product was purified by column chromatography (hexane/AcOEt) and recrystallization (hexane/AcOEt, 25° C. to −50° C.) followed by washing the solid with hexane. The target compound as orange solid (2.03 g) with NMR purity of 90% in 27.0% yield was obtained. ¹H-NMR (CDCl₃), delta (ppm): 2.57 (s, 3H), 3.57 (t, J=4.7 Hz, 1H), 4.75 (d, J=4.6 Hz, 2H), 7.21-7.38 (m, 2H), 7.39-7.50 (m, 1H), 7.61 (d, J=8.0 Hz, 1H).

Example 7. Preparation of SM-7:
2-Hydroxy-2'-methoxyacetophenone

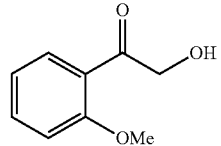

SM-7

Step A. A 200 mL flask was charged with 2'-methoxyacetophenone (7.51 g, 50 mmol), N-bromosuccinimide (9.79 g, 55 mmol), p-toluenesulfonic acid (10.79 g, 55 mmol) and MeCN (100 mL) under nitrogen stream and the mixture was stirred for 3.5 hours at 80° C. The mixture was allowed to cool to room temperature and then MeCN was removed by an evaporator. CHCl₃ (150 mL) and H₂O (50 mL) were added to a residue and the lower layer was separated and then washed with saturated aqueous NaHCO₃ (50 mL) twice and brine (50 mL). The solution was dried over anhydrous MgSO₄ and filtrated. Solvents were then removed in an evaporator and the crude product as orange-brown oil (11.74 g) in >99.9% yield was obtained. This product was identified as 2-Bromo-2'-methoxyacetophenone contaminated with some dibromo compound. ¹H-NMR (CDCl₃), delta (ppm): 3.93 (s, 3H), 4.59 (s, 2H), 6.97 (d, J=8.4 Hz, 1H), 7.00-7.06 (m, 1H), 7.50 (ddd, J=1.8, 7.3, 8.4 Hz, 1H), 7.81 (dd, J=1.8, 7.7 Hz, 1H).

Step B. A 200 mL flask was charged with the crude 2-Bromo-2'-methoxyacetophenone obtained in Step A (11.74 g, 50 mmol, 1.0 eq.) and MeOH (100 mL) under nitrogen stream, and then HCOONa (10.20 g, 150 mmol, 3.0 eq.) was added. The mixture was stirred for 4 hours at 80° C. The mixture was allowed to cool to room temperature and the remaining solid (HCOONa) was filtrated and then the filtrate was concentrated in an evaporator. CHCl3 (150 mL) was added to the residue and the precipitated solid was filtrated through celite and the celite was washed with CHCl₃ (50 mL). H₂O (50 mL) were added to the filtrate and the lower layer was separated and washed with saturated aqueous NaHCO₃ (50 mL) twice and brine (50 mL). MeOH (50 mL) and HCOONa (3.4 g, 50 mmol, 1.0 eq.) were added to the crude material and then the mixture was stirred for 3 hours at 80° C. The mixture was allowed to cool to room temperature and the remaining solid (HCOONa) was filtrated and then the filtrate was concentrated in an evaporator. CHCl₃ (100 mL) was added to the residue and the precipitated solid was filtrated and then the solid was washed with CHCl₃ (50 mL). H₂O (50 mL) were added to the combined filtrate and the lower layer was separated and washed with 1N HCl (50 mL) and brine (50 ml) twice. The solution was dried over anhydrous MgSO₄ and filtered and then solvents were removed in an evaporator. The crude material was purified by column chromatography (hexane/AcOEt) to obtain the target compound as pale yellow solid (4.22 g) in 50.8% yield. ¹H-NMR (CDCl₃), delta (ppm): 4.8 (t, J=4.8 Hz), 3.97 (s, 3H), 4.79 (d, J=4.0 Hz, 2H), 7.03 (d, J=8.4 Hz, 1H), 7.09 (ddd, J=0.8, 7.5, 7.6 Hz, 1H), 7.58 (ddd, J=1.8, 7.6, 8.1 Hz, 1H), 8.08 (dd, J=1.8, 7.8 Hz, 1H).

Example 8. Preparation of SM-8: 2-Hydroxy-2'-trifluoromethylacetophenone

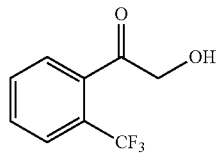

SM-8

Step A. A 200 mL flask was charged with 2'-trifluoromethylacetophenone (9.41 g, 50 mmol), N-bromosuccinimide (9.79 g, 55 mmol, 1.1 eq.), p-toluenesulfonic acid (10.46 g, 55 mmol, 1.1 eq.) and MeCN (100 mL) under nitrogen stream and the mixture was stirred for 4 hours at 80° C. The mixture was allowed to cool to room temperature and then MeCN was removed by an evaporator. CHCl$_3$ (150 mL) and H$_2$O (50 mL) were added to the residue and the lower layer was separated and then washed with saturated aqueous NaHCO$_3$ (50 mL) twice and brine (50 mL). The solution was dried over anhydrous MgSO$_4$ and filtered and then solvents were removed in an evaporator to obtain the crude product as yellow oil (13.66 g) in >99.9% yield. This product was identified as 2-Bromo-2'-trifluoromethylacetophenone contaminated with some dibromo compound. $^1$H-NMR (CDCl$_3$), delta (ppm): 4.36 (s, 2H), 7.48-7.50 (m, 1H), 7.60-7.64 (m, 2H), 7.72-7.75 (m, 1H), $^{19}$F-NMR (CDCl$_3$), delta in ppm, standard: C$_6$F$_6$=−162.2 ppm: −58.68.

Step B. A 200 mL flask was charged with the crude of 2-Bromo-2'-trifluoromethylacetophenone obtained in Step A (13.66 g, 50 mmol, 1.0 eq.) and MeOH (100 mL) under nitrogen stream, and then HCOONa (10.20 g, 150 mmol, 3.0 eq.) was added. The mixture was stirred for 12 hours at 80° C. The mixture was then allowed to cool to room temperature and the remaining solid (HCOONa) was filtrated and then filtrate was concentrated in an evaporator. CHCl$_3$ (150 mL) was added to the residue and the precipitated solid was filtrated and the solid was washed with CHCl$_3$ (50 mL). 1N HCl (50 mL) was added to the combined filtrate and the lower layer was separated and washed with 1N HCl (50 mL) and brine (50 ml). The solution was dried over anhydrous MgSO$_4$ and filtered and then the solvents were removed in an evaporator. The crude material was purified by column chromatography (hexane/AcOEt) to obtain the target compound as orange oil (2.15 g) in 21.0% yield. $^1$H-NMR (CDCl$_3$), delta (ppm): 4.65 (s, 2H), 7.42-7.49 (m, 1H), 7.60-7.69 (m, 2H), 7.73-7.81 (m, 1H), $^{19}$F-NMR (CDCl$_3$), delta in ppm, standard: C$_6$F$_6$=−162.2 ppm: −58.84 (s, 3F).

Example 9. Preparation of SM-9: 2-Hydroxy-1-acetonaphthone

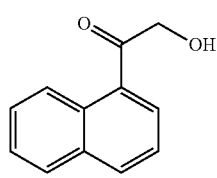

SM-9

Step A. A 200 mL flask was charged with 1-acetonaphthone (8.51 g, 50 mmol), N-bromosuccinimide (9.79 g, 55 mmol, 1.1 eq.), p-toluenesulfonic acid (10.46 g, 55 mmol, 1.1 eq.) and MeCN (100 mL) under nitrogen stream and the mixture was stirred for 6 hours at 80° C. The mixture was allowed to cool to room temperature and then MeCN was removed by an evaporator. CHCl$_3$ (150 mL) and H$_2$O (50 mL) were added to the residue and the lower layer was separated and then washed with saturated aqueous NaHCO$_3$ (50 mL) twice and brine (50 mL). The solution was dried over anhydrous MgSO$_4$ and filtered and then solvents were removed in an evaporator to obtain a product identified as 2-Bromo-1-acetonaphthone contaminated with some dibromo compound. $^1$H-NMR (CDCl$_3$), delta (ppm): 4.56 (s, 2H), 7.48-7.64 (m, 3H), 7.86-7.92 (m, 2H), 8.03 (d, J=8.2 Hz, 1H), 8.62 (d, J=8.7 Hz, 1H)

Step B. A 200 mL flask was charged with the crude of 2-Bromo-1-acetonaphthone and MeOH (100 mL) under nitrogen stream, and then HCOONa (10.20 g, 150 mmol, 3.0 eq.) was added. The mixture was stirred for 4 hours at 80° C. The mixture was then allowed to cool to room temperature and the remaining solid (HCOONa) was filtrated off and the filtrate was concentrated in an evaporator. CHCl$_3$ (150 mL) was added to the residue and the precipitated solid was filtrated and the solid was then washed with CHCl$_3$ (50 mL). H$_2$O (50 mL) was added to the combined filtrate and the lower layer was separated and washed with 1N HCl (50 mL) and brine (50 ml). The solution was dried over anhydrous MgSO$_4$ and filtered and then solvents were removed in an evaporator. The crude material was purified by column chromatography (hexane/AcOEt) to obtain the target compound as yellow sticky oil to yellow solid (3.55 g) in 38.1% yield. $^1$H-NMR (CDCl$_3$), delta (ppm): 3.71 (brs, 1H), 4.95 (s, 2H), 7.53-7.64 (m, 2H), 7.69 (ddd, J=1.4, 6.9, 8.5 Hz, 1H), 7.93 (dd, J=1.4, 8.2 Hz, 1H), 8.11 (d, J=8.2 Hz, 1H), 8.90 (d, J=8.7 Hz, 1H)

Example 10. Preparation of SM-10: 2-Hydroxypropiophenone

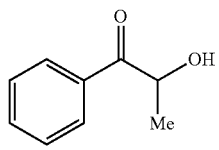

SM-10

A 200 mL flask was charged with the crude of 2-Bromopropiophenone (10.65 g, 50 mmol, 1.0 eq.) and MeOH (100 mL) under nitrogen stream, and then HCOONa (10.20 g, 150 mmol, 3.0 eq.) was added. The mixture was stirred for 12 hours at 80° C. The mixture was allowed to cool to room temperature and the remaining solid (HCOONa) was filtrated off and then the filtrate was concentrated in an evaporator. CHCl$_3$ (150 mL) was added to the residue and the precipitated solid was filtrated and the solid was washed with CHCl$_3$ (50 mL). The combined filtrate was then washed with 1N HCl (50 mL) and brine (50 ml). The solution was dried over anhydrous MgSO$_4$ and filtered and then the solvents were removed in an evaporator. The crude product was purified by column chromatography (hexane/AcOEt) to obtain the target compound as colorless oil (5.56 g) in 74.0% yield. $^1$H-NMR (CDCl$_3$), delta (ppm): 1.48 (d, J=7.0 Hz, 3H), 5.19 (q, J=7.0 Hz, 1H), 7.54 (dd, J=7.5, 7.8 Hz, 2H), 7.65 (tt, J=1.2, 7.4 Hz, 1H), 7.95 (dd, J=1.2, 8.3 Hz, 2H)

PAG Synthesis

The PAG compounds of Examples 11-24 were prepared using the general reaction conditions shown below.

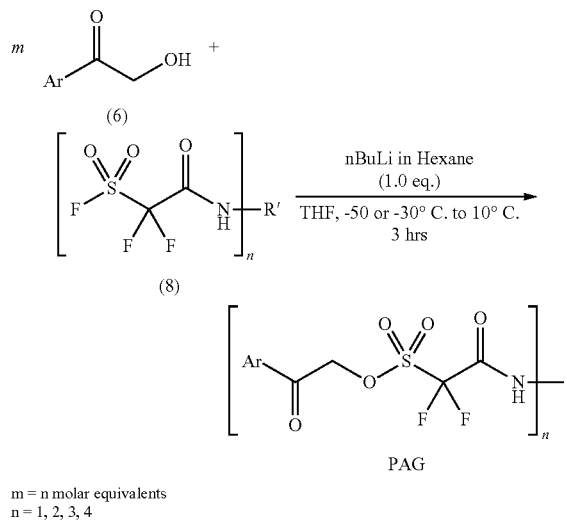

m = n molar equivalents
n = 1, 2, 3, 4

Example 11. Preparation of PAG-1

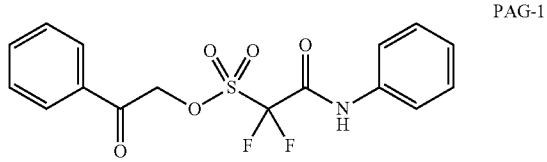 [SMILES: O=C(COS(=O)(=O)C(F)(F)C(=O)Nc1ccccc1)c1ccccc1]

A 200 mL flask was charged with 1-difluoro-2-oxo-2-(phenylamino)ethane-1-sulfonyl fluoride (SM-1) (2.53 g, 10.0 mmol, 1.0 eq.), 2-hydroxyacetophenone (Sigma-Aldrich) (1.36 g, 10.0 mmol, 1.0 eq.) and THF (50 mL) under nitrogen stream, and the mixture was stirred for 10 minutes at −30° C. n-BuLi (1.6 M, 6.3 mL, 10.0 mmol, 1.0 eq.) was added drop wise to the mixture over 10 minutes. The mixture was allowed to warm to 0° C. and stirred for 2 hours at 0° C. 1N HCl (50 mL) was added to the final reaction mixture and then AcOEt (150 mL) was added. The upper layer was separated and washed with saturated aqueous NaHCO$_3$ (25 mL×3) and brine (15 mL) and the solution was subsequently dried over anhydrous MgSO$_4$ and filtered. Solvents were removed in an evaporator and then CH$_2$Cl$_2$ (50 mL) was added to the crude material. The sodium salt separated was removed by filtration and the filtrate was concentrated in an evaporator. The residue was washed with 2×40 mL hexane and the hexane was removed by decantation. The obtained crude product was purified by recystallization (hexane/CH$_2$Cl$_2$, 40° C. to 0° C.) to obtain the target PAG as white solid (0.69 g) in 18.8% yield. $^1$H-NMR (CDCl$_3$), delta (ppm): 5.86 (s, 2H), 7.27 (t, J=7.4 Hz, 1H), 7.44 (dd, J=8.4, 7.5 Hz, 2H), 7.61 (dd, J=7.7, 7.9 Hz, 2H), 7.76 (dt, J=1.2, 7.5 Hz, 1H), 7.82 (dd, J=1.1, 8.2 Hz, 2H), 7.99 (dd, J=1.2, 8.4 Hz, 2H), 10.00 (brs, 1H). $^{19}$F-NMR (CDCl$_3$), delta in ppm, standard: C$_6$F$_6$=−162.2 ppm: −108.26 (s, 2F).

Example 12. Preparation of PAG-2

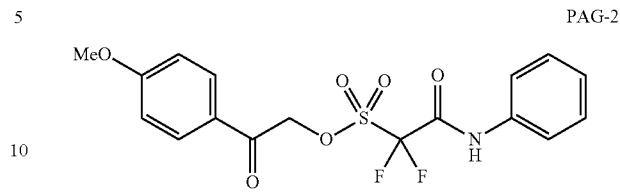

A 100 mL flask was charged with 1,1-difluoro-2-oxo-2-(phenylamino)ethane-1-sulfonyl fluoride (SM-1) (0.97 g, 3.89 mmol, 1.0 eq.), 2-hydroxy-4'-methoxyacetophenone (SM-4) (0.64 g, 3.98 mmol, 1.0 eq.) and THF (20 mL) under nitrogen stream and the mixture was stirred for 10 minutes at −30° C. n-BuLi (1.6 M, 2.4 mL, 3.89 mmol, 1.0 eq.) was added drop wise to the mixture over 10 minutes. The mixture was stirred for 2 hours at −30° C. to 10° C. 1N HCl (20 mL) was added to the final reaction mixture and then AcOEt (60 mL) was added. The upper layer was separated and washed with saturated aqueous NaHCO$_3$ aq./brine (20 mL/20 mL) and brine (20 mL) and the solution was subsequently dried over anhydrous MgSO$_4$ and filtered. Solvents were removed in an evaporator and then CH$_2$Cl$_2$ (50 mL) was added to the residue and the sodium salt separated was removed by filtration and the filtrate was concentrated in an evaporator. The concentrate was then washed with 3×50 mL hexane and the hexane was removed by decantation. This crude material was purified by column chromatography (hexane/AcOEt) followed by recrystallization (hexane/AcOEt, 50° C. to 0° C.) to obtain the target PAG as a white solid (0.49 g) in 31.2% yield. $^1$H-NMR (CDCl$_3$), delta (ppm): 3.91 (s, 1H), 5.78 (s, 2H), 7.01 (d, J=8.9 Hz, 2H), 7.21 (t, J=7.5 Hz, 1H), 7.39 (dd, J=7.6, 8.4 Hz, 2H), 7.80 (d, J=8.1 Hz, 2H), 7.93 (d, J=9.0 Hz, 2H), 10.31 (brs, 1H), $^{19}$F-NMR (CDCl$_3$), delta in ppm, standard: C$_6$F$_6$=−162.2 ppm: −108.28 (s, 2F).

Example 13. Preparation of PAG-3

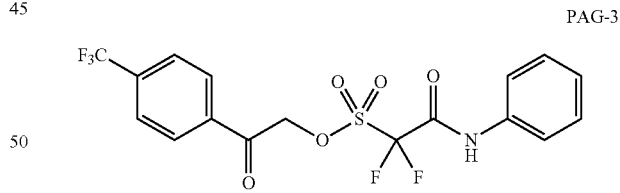

A 100 mL flask was charged with 1,1-difluoro-2-oxo-2-(phenylamino)ethane-1-sulfonyl fluoride (SM-1) (1.22 g, 4.80 mmol, 1.0 eq.), 2-hydroxy-4'-trifluoromethylacetophenone (SM-5) (0.98 g, 4.80 mmol, 1.0 eq.) and THF (24 mL) under nitrogen stream, and the mixture was stirred for 5 minutes at −30° C. n-BuLi (1.6 M, 3.0 mL, 4.80 mmol, 1.0 eq.) was added dropwise to the mixture over 5 minutes. The mixture was stirred for 2 hours at −30° C. to 10° C. 1N HCl (24 mL) was added to the final reaction mixture and then AcOEt (72 mL) was added. The upper layer was separated and washed with 1N HCl (24 mL), saturated aqueous NaHCO$_3$ (24 mL) and brine (24 mL) and the solution was subsequently dried over anhydrous MgSO$_4$ and filtered. Solvents were removed in an evaporator and then hexane (100 mL) was added to the residue and this mixture was stirred for 45 minutes at 40° C. and finally the hexane was removed by decantation. This procedure was repeated two more times. CH$_2$Cl$_2$ (100 mL) was then added to the remaining material and the sodium salt formed was removed by filtration and the filtrate was concentrated in an evaporator. The obtained crude product was purified by recrystallization (hexane/CHCl$_3$, 50° C. to 0° C.) to obtain the target PAG as white solid (0.22 g) in 10.3% yield. $^1$H-NMR (d-Acetone), delta (ppm): 6.12 (s, 2H), 7.26 (t, J=7.4 Hz, 1H), 7.43 (dd, J=7.6, 8.4 Hz, 2H), 7.75 (d, J=8.5 Hz, 2H), 7.96 (d, J=8.3 Hz, 2H), 8.28 (d, J=8.2 Hz, 2H), 10.42 (brs, 1H), $^{19}$F-NMR (d-Acetone), delta in ppm, standard: C$_6$F$_6$=−162.2 ppm: −61.36 (s, 3F), −105.32 (s, 1F), −105.37 (s, 1F).

Example 14. Preparation of PAG-4

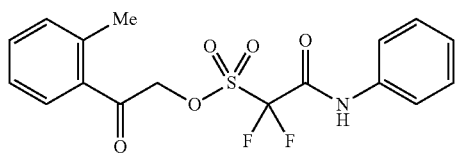

PAG-4

A 100 mL flask was charged with 1,1-difluoro-2-oxo-2-(phenylamino)ethane-1-sulfonyl fluoride (SM-1) (1.22 g, 4.80 mmol, 1.0 eq.), 2-Hydroxy-2'-methylacetophenone (SM-6) (0.79 g, 5.38 mmol, 1.1 eq.) and THF (24 mL) under nitrogen stream and the mixture was stirred for 10 minutes at −30° C. n-BuLi (1.6 M, 3.0 mL, 4.80 mmol, 1.0 eq.) was added dropwise to the mixture over 5 minutes. The mixture was stirred for 2.5 hours at −30° C. to 10° C. 1N HCl (24 mL) was added to the final reaction mixture and then AcOEt (72 mL) was added. An upper layer was separated and washed with 1N HCl (24 mL), saturated aqueous NaHCO$_3$ (24 mL) and brine (24 mL). The solution was subsequently dried over anhydrous MgSO$_4$ and filtered. Solvents were removed in an evaporator and then hexane (100 mL) was added to the crude and a mixture was stirred for 20 minute at room temperature and the hexane was removed by decantation. This procedure was repeated two more times. CH$_2$Cl$_2$ (70 mL) was added to the remaining material and the sodium salt separated was removed by filtration and the filtrate was concentrated in an evaporator. The obtained crude product was purified by recrystallization (hexane/CHCl$_3$, 60° C. to 0° C.) to obtain the target PAG as white solid (0.45 g) in 24.3% yield. $^1$H-NMR (CDCl$_3$), delta (ppm): 2.61 (s, 3H), 5.69 (s, 2H), 7.22 (t, J=7.5 Hz, 1H), 7.32-7.43 (m, 2H), 7.39 (dd, J=7.6, 7.7 Hz, 2H), 7.53 (t, J=7.6 Hz, 1H), 7.59 (d, J=7.6 Hz, 1H), 7.76 (d, J=8.2 Hz, 2H), $^{19}$F-NMR (CDCl$_3$), delta in ppm, standard: C$_6$F$_6$=−162.2 ppm: −108.28 (s, 2F).

Example 15. Preparation of PAG-5

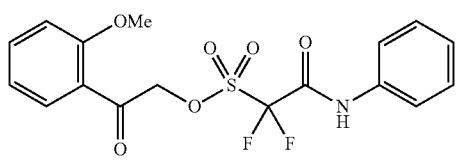

PAG-5

A 100 mL flask was charged with 1,1-difluoro-2-oxo-2-(phenylamino)ethane-1-sulfonyl fluoride (SM-1) (1.22 g, 4.80 mmol, 1.0 eq.), 2-Hydroxy-2'-methoxyacetophenone (SM-7) (0.80 g, 4.80 mmol, 1.0 eq.) and THF (24 mL) under nitrogen stream and the mixture was stirred for 5 minutes at −30° C. n-BuLi (1.6 M, 3.0 mL, 4.80 mmol, 1.0 eq.) was added dropwise to the mixture over 5 minutes. The mixture was stirred for 3 hours at −30° C. to 10° C. 1N HCl (24 mL) was added to the final reaction mixture and then AcOEt (72 mL) was added. The upper layer was separated and washed with 1N HCl (24 mL), saturated aqueous NaHCO$_3$ (24 mL) and brine (24 mL). The solution was subsequently dried over anhydrous MgSO$_4$ and filtered. Solvents were removed in an evaporator and then hexane (100 mL) was added to the residue and the mixture was stirred for 45 minute at 40° C. and then the hexane was removed by decantation. This procedure was repeated two more times. CH$_2$Cl$_2$ (100 mL) was added to the remaining material and the sodium salt separated was removed by filtration and the filtrate was concentrated in an evaporator. This crude product was purified by recrystallization (hexane/CHCl$_3$, 50° C. to 0° C.) to obtain the target PAG as white solid (0.63 g) in 32.6% yield. $^1$H-NMR (CDCl$_3$), delta (ppm): 4.00 (s, 3H). 5.70 (s, 2H), 7.05 (d, J=8.3 Hz, 1H), 7.13 (d, J=7.2 Hz, 1H), 7.21 (t, J=7.4 Hz, 1H), 7.39 (dd, J=7.6, 8.4 Hz, 2H), 7.64 (ddd, J=1.8, 7.3, 8.6 Hz, 1H), 7.81 (dd, J=1.1, 8.8 Hz, 2H), 8.12 (dd, J=1.8, 7.9 Hz, 1H), 10.30 (brs, 1H), $^{19}$F-NMR (CDCl$_3$), delta in ppm, standard: C$_6$F$_6$=−162.2 ppm: −108.54 (s, 2F).

Example 16. Preparation of PAG-6

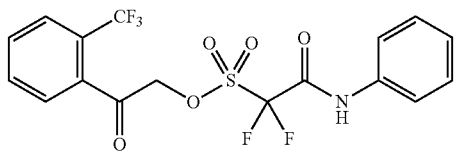

PAG-6

A 100 mL flask was charged with 1,1-difluoro-2-oxo-2-(phenylamino)ethane-1-sulfonyl fluoride (SM-1) (1.36 g, 5.34 mmol, 1.0 eq.), 2-Hydroxy-2'-trifluoromethylacetophenone (SM-8) (1.09 g, 5.34 mmol, 1.0 eq.) and THF (27 mL) under nitrogen stream and the mixture was stirred for 10 minutes at −50° C. n-BuLi (1.6 M, 3.3 mL, 5.34 mmol, 1.0 eq.) was added dropwise to the mixture over 10 minutes. The mixture was stirred for 3 hours at −50° C. to 10° C. 1N HCl (27 mL) was added to the final reaction mixture and then AcOEt (81 mL) was added. The upper layer was separated and washed with 1N HCl (27 mL) and brine (27 mL). The solution was subsequently dried over anhydrous MgSO$_4$ and filtered. Solvents were removed in an evaporator and the crude product was purified by column chromatography (hexane/AcOEt) twice and recrystallization (hexane/CHCl$_3$, 50° C. to 0° C.) to obtain the target PAG as pale yellow solid (0.32 g) in 13.7% yield. $^1$H-NMR (CDCl$_3$), delta (ppm): 5.49 (s, 2H), 7.20 (t, J=7.6 Hz, 1H), 7.38 (dd, J=7.6, 8.4 Hz, 2H), 7.52-7.54 (m, 1H), 7.64-7.77 (m, 4H), 7.79-7.86 (m, 1H), $^{19}$F-NMR (CDCl$_3$), delta in ppm, standard: C$_6$F$_6$=−162.2 ppm: −58.61 (s, 3F), −108.15 (s, 2F).

Example 17. Preparation of PAG-7

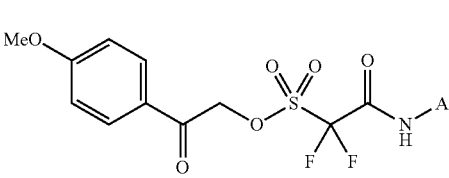

PAG-7

A 100 mL flask was charged with 1, 1-Difluoro-2-oxo-2-(1-adamantylamino)ethanesulfonyl fluoride (SM-2) (1.49 g, 4.80 mmol, 1.0 eq.), 2-Hydroxy-4'-methoxyacetophenone (SM-4) (0.80 g, 4.80 mmol, 1.0 eq.) and THF (24 mL) under nitrogen stream and the mixture was stirred for 10 minutes at −30° C. n-BuLi (1.6 M, 3.0 mL, 4.80 mmol, 1.0 eq.) was added drop wise to the mixture over 5 minutes. The mixture was stirred for 3 hours at −30° C. to 10° C. 1N HCl (24 mL) was added to the final reaction mixture and then AcOEt (72 mL) was added. The upper layer was separated and washed with saturated aqueous NaHCO₃ (24 mL) twice and brine (24 mL). The solution was subsequently dried over anhydrous MgSO₄ and filtered. Solvents were removed in an evaporator and then hexane (100 mL) was added to the crude material. The mixture was stirred overnight at room temperature and then the solid formed was filtrated and the solid was washed with hexane (50 mL). This solid was mostly soluble in CHCl₃ (70 mL) and the remaining insoluble solid was filtrated off and the filtrate was concentrated. Hexane (100 mL) was added to the concentrate and the mixture was stirred for 1.5 hours at 40° C. and finally the hexane was separated by decantation. This procedure was repeated three more times. The obtained crude product was purified by recrystallization (hexane/CHCl₃, 50° C. to 0° C.) to obtain the target PAG as white solid (0.45 g) in 20.5% yield. $^1$H-NMR (CDCl₃), delta (ppm): 1.69 (brs, 6H), 2.09 (brs, 6H), 2.11 (brs, 3H), 3.88 (s, 3H), 5.62 (s, 2H), 6.97 (d, J=9.0 Hz, 2H), 7.12 (brs, 1H), 7.86 (d, J=8.0 Hz, 2H), $^{19}$F-NMR (CDCl₃), delta in ppm, standard: C₆F₆=−162.2 ppm: −107.78 (2F).

Example 18. Preparation of PAG-8

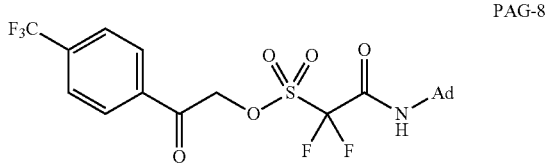

PAG-8

A 100 mL flask was charged with 1, 1-Difluoro-2-oxo-2-(1-adamntylamino)ethanesulfonyl fluoride (SM-2) (0.84 g, 2.71 mmol, 1.0 eq.), 2-Hydroxy-4'-trifluoromethylacetophenone (SM-4) (0.55 g, 2.71 mmol, 1.0 eq.) and THF (14 mL) under nitrogen stream and the mixture was stirred for 5 minutes at −50° C. n-BuLi (1.6 M, 1.7 mL, 2.71 mmol, 1.0 eq.) was added dropwise to the mixture over 5 minutes. The mixture was stirred for 3 hours at −50° C. to 10° C. 1N HCl (14 mL) was added to the final reaction mixture and then AcOEt (42 mL) was added. The upper layer was separated and washed with 1N HCl (14 mL), saturated aqueous NaHCO₃ (7 mL) and brine (14 mL). The solution was subsequently dried over anhydrous MgSO₄ and filtered. Solvents were removed in an evaporator and then hexane (50 mL) was added to the residue and the mixture was stirred overnight at room temperature. The solid separated was filtrated and washed with hexane (50 mL). This solid was mostly soluble in CH₂Cl₂ (100 mL) and the insoluble part was filtrated off and the filtrate was concentrated. The obtained crude product was purified by column chromatography (hexane/AcOEt) and recrystallization (hexane/CHCl₃, 50° C. to 0° C.) to obtain the target PAG as white solid (0.20 g) in 14.9% yield. $^1$H-NMR (CDCl₃), delta (ppm): 1.69 (brs, 6H), 2.06 (brs, 6H), 2.12 (brs, 3H), 5.64 (s, 2H), 6.56 (brs, 1H), 7.78 (d, J=8.6 Hz, 2H), 8.01 (d, J=8.7 Hz, 2H), $^{19}$F-NMR (CDCl₃), delta in ppm, standard: C₆F₆=−162.2 ppm: −63.88 (s, 3H) −107.41 (s, 2F).

Example 19. Preparation of PAG-9

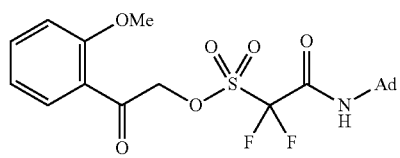

PAG-9

A 100 mL flask was charged with 1, 1-Difluoro-2-oxo-2-(1-adamntylamino)ethanesulfonyl fluoride (SM-2) (1.49 g, 4.80 mmol, 1.0 eq.), 2-Hydroxy-2'-methoxyacetophenone (SM-7) (0.80 g, 4.80 mmol, 1.0 eq.) and THF (24 mL) under nitrogen stream and the mixture was stirred for 10 minutes at −50° C. n-BuLi (1.6 M, 3.0 mL, 4.80 mmol, 1.0 eq.) was added drop wise to the mixture over 10 minutes. The mixture was stirred for 3 hours at −50° C. to 10° C. 1N HCl (24 mL) was added to the final reaction mixture and then AcOEt (72 mL) was added. The upper layer was separated and washed with 1N HCl (24 mL) and brine (24 mL). The solution was subsequently dried over anhydrous MgSO₄ and filtered. Solvents were removed in an evaporator and then hexane (100 mL) was added to the residue and the mixture was stirred for 2.5 hours at room temperature. The solid formed was filtrated and washed with hexane (50 mL). This solid was mostly soluble in CH₂Cl₂ (100 mL) and the remaining insoluble solid was filtrated off and then the filtrate was concentrated. The obtained crude product was purified by column chromatography (hexane/AcOEt) and recrystallization (hexane/CHCl₃, 50° C. to 0° C.) to obtain the target PAG as white solid (0.99 g) in 45.2% yield. $^1$H-NMR (CDCl₃), delta (ppm): 1.69 (brs, 6H), 2.10 (brs, 9H), 3.97 (s, 3H), 5.56 (s, 2H), 7.00 (d, J=8.4 Hz, 1H), 7.08 (dd, J=7.2, 7.9 Hz, 1H), 7.59 (ddd, J=1.8, 7.6, 8.1 Hz, 1H), 8.02 (dd, J=1.8, 7.9 Hz, 1H), $^{19}$F-NMR (CDCl₃), delta in ppm, standard: C₆F₆=−162.2 ppm: −108.29 (s, 2F).

Example 20. Preparation of PAG-10

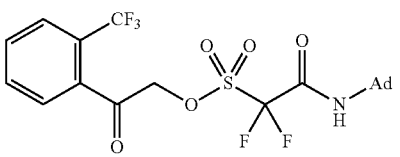

PAG-10

A 100 mL flask was charged with 1, 1-Difluoro-2-oxo-2-(1-adamntylamino)ethanesulfonyl fluoride (SM-2) (1.49 g, 4.80 mmol, 1.0 eq.), 2-Hydroxy-2'-trifluoromethylacetophenone (SM-8) (0.98 g, 4.80 mmol, 1.0 eq.) and THF (24 mL) under nitrogen stream and the mixture was stirred for 10 minutes at −50° C. n-BuLi (1.6 M, 3.0 mL, 4.80 mmol, 1.0 eq.) was added dropwise to the mixture over 10 minutes. The mixture was stirred for 3 hours at −50° C. to 10° C. 1N HCl (24 mL) was added to the final reaction mixture and then AcOEt (72 mL) was added. The upper layer was separated and washed with 1N HCl (24 mL) and brine (24 mL). This solution was subsequently dried over anhydrous MgSO₄ and filtered. The Solvents were removed in an evaporator and then the crude product was purified by column chromatography (hexane/AcOEt) to obtain the target PAG as colorless oil (0.70 g) in 29.6% yield. $^1$H-NMR (CDCl₃), delta (ppm):

1.68 (t, J=3.0 Hz, 3H), 2.04 (brs, 3H), 2.05 (brs, 3H), 2.11 (brs, 3H), 5.35 (s, 2H), 6.52 (brs, 1H), 7.48-7.51 (m, 1H), 7.66-7.68 (m, 2H), 7.77-7.79 (m, 1H), $^{19}$F-NMR (CDCl$_3$), delta in ppm, standard: C$_6$F$_6$=−162.2 ppm: −58.66 (s, 3F), −107.51 (s, 2F).

Example 21. Preparation of PAG-11

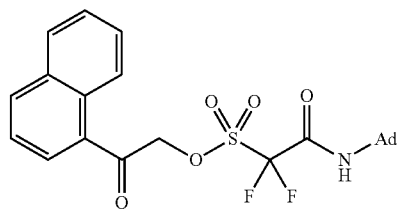

PAG-11

A 100 mL flask was charged with 1, 1-Difluoro-2-oxo-2-(1-adamntylamino)ethanesulfonyl fluoride (SM-2) (1.58 g, 5.10 mmol, 1.0 eq.), 2-Hydroxy-1-acetonaphthone (SM-9) (0.94 g, 5.10 mmol, 1.0 eq.) and THF (25 mL) under nitrogen stream and the mixture was stirred for 10 minutes at −50° C. n-BuLi (1.6 M, 3.2 mL, 5.10 mmol, 1.0 eq.) was added dropwise to the mixture over 5 minutes. The mixture was stirred for 2.5 hours at −50° C. to 5° C. 1N HCl (25 mL) was added to the final reaction mixture and then AcOEt (75 mL) was added. The upper layer was separated and the lower layer was extracted with AcOEt (50 mL) and then the organic solutions were combined. This solution was washed with 1N HCl (25 mL) and brine (25 mL). The solution was subsequently dried over anhydrous MgSO$_4$ and filtered. The solvents were removed in an evaporator and the crude product was purified by column chromatography (hexane/AcOEt) followed by recrystallization (hexane/CHCl$_3$, 50° C. to 0° C.) to obtain the target PAG as white solid (0.39 g) in 16.3% yield. $^1$H-NMR (CDCl$_3$), delta (ppm): 1.73 (brs, 6H), 2.13 (brs, 9H), 5.70 (s, 2H), 6.84 (brs, 1H), 7.55-5.72 (m, 3H), 7.86 (d, J=7.3 Hz, 1H), 7.94 (d, J=8.0 Hz, 1H), 8.14 (d, J=8.3 Hz, 1H), 8.75 (d, J=8.5 Hz, 1H), $^{19}$F-NMR (CDCl$_3$), delta in ppm, standard: C$_6$F$_6$=−162.2 ppm: −107.70 (s, 2F).

Example 22. Preparation of DPAG-1

A 100 mL flask was charged with 2,2'-(hexane-1,6-diylbis (azanediyl)bis(1,1-difluoro-2-oxoethane-1-sulfonyl fluoride (SM-3) (1.68 g, 3.9 mmol, 1.0 eq.), 2-Hydroxy-Acetophenone (Sigma-Aldrich) (1.05 g, 7.7 mmol, 2.0 eq.) and THF (40 mL) under nitrogen stream and the mixture was stirred for 5 minutes at −30° C. n-BuLi (1.6 M, 4.8 mL, 7.7 mmol, 2.0 eq.) was added dropwise to the mixture over 10 minutes. The mixture was allowed to warm to 0° C. and stirred for 2 hours at 0° C. 1N HCl (40 mL) was added to the final reaction mixture and then AcOEt (120 mL) was added. The upper layer was separated and washed with saturated aqueous NaHCO$_3$ (40 mL) and brine (40 mL). This solution was subsequently dried over anhydrous MgSO$_4$ and filtered. The solvents were removed in an evaporator and the crude product was purified by column chromatography (hexane/AcOEt=8/2 to 3/7). The obtained solid was purified by recystallization (hexane/AcOEt, 70° C. to 0° C.) to obtain the target PAG as white solid (0.34 g) in 13.4% yield. $^1$H-NMR (CDCl$_3$), delta (ppm): 1.45 (brs, 4H), 1.65-1.69 (m, 4H), 3.48 (dt, J=6.6, 6.4 Hz, 4H), 5.75 (s, 4H), 7.56 (dd, J=7.8, 8.0 Hz, 4H), 7.71 (t, J=7.4 Hz, 2H), 7.71 (brs, 2H), 7.92 (dd, J=1.4, 7.9 Hz, 2H). $^{19}$F-NMR (CDCl$_3$), delta in ppm, standard: C$_6$F$_6$=−162.2 ppm: −108.21 (s, 2F).

Example 23. Preparation of DPAG-2

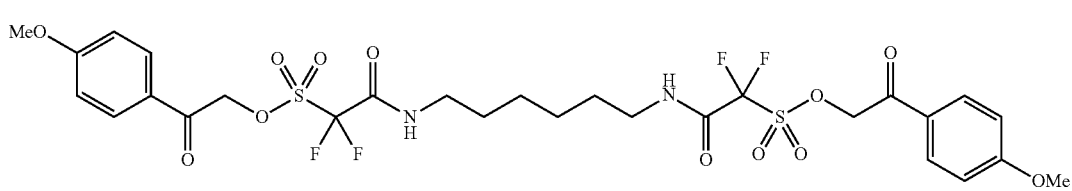

DPAG-2

A 100 mL flask was charged with 2,2'-(hexane-1,6-diylbis (azanediyl)bis(1,1-difluoro-2-oxoethane-1-sulfonyl fluoride (SM-3) (1.09 g, 2.49 mmol, 1.0 eq.), 2-Hydroxy-4'-methoxyacetophenone (SM-4) (0.83 g, 4.98 mmol, 2.0 eq.) and THF (25 mL) under nitrogen stream and the mixture was stirred for 10 minutes at −30° C. n-BuLi (1.6 M, 3.1 mL, 4.98 mmol, 2.0 eq.) was added dropwise to the mixture over 10 minutes. The mixture was stirred for 2 hours at −30 to 10° C. 1N HCl (25 mL) was added to the final reaction mixture and then AcOEt (75 mL) was added. The upper layer was separated and washed with saturated aqueous NaHCO$_3$ aq./brine (25 mL/25 mL) and brine (25 mL). This solution was subsequently dried over anhydrous MgSO$_4$ and filtered. This solution was concentrated in an evaporator. AcOEt (100 mL) was added to the residue and the solution was washed again with saturated aqueous NaHCO$_3$ aq./brine (25 mL/25 mL) twice and brine (25 mL). This solution was subsequently dried over MgSO$_4$ and filtrated and then the solvents were removed in an evaporator. Hexane (100 mL) was added to the crude and this mixture was stirred for an hour at 40° C. and the hexane was removed by decantation.

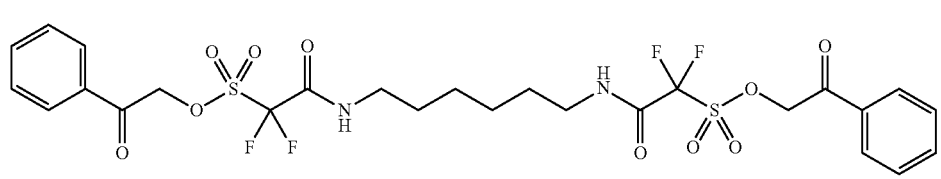

DPAG-1

This procedure was repeated two more times. CH₂Cl₂ (100 mL) was added to this crude material and the sodium salt separated was filtered off and the filtrate was concentrated in an evaporator. The obtained crude product was purified by column chromatography (hexane/AcOEt) followed by recrystallization (hexane/CH₂Cl₂, 40° C. to 0° C.) to obtain the target PAG as white solid (0.12 g) in 6.9% yield. $^1$H-NMR (d-DMSO), delta (ppm): 1.23 (t, J=7.0 Hz, 4H), 1.39 (t. J=6.6 Hz, t), 3.08 (tt, J=6.6, 6.7 Hz, 4H), 3.87 (s, 6H), 5.86 (s, 2H), 7.13 (d, J=9.0 Hz, 4H), 7.94 (d, J=9.0 Hz, 2H), 8.15 (t, J=5.6 Hz, 1H), $^{19}$F-NMR (d-DMSO), delta in ppm, standard: $C_6F_6$=−162.2 ppm: −109.30 (s, 4F).

Preparation of Comparative PAG Compounds

Example 24. Preparation of Comparative PAG, CPAG-1

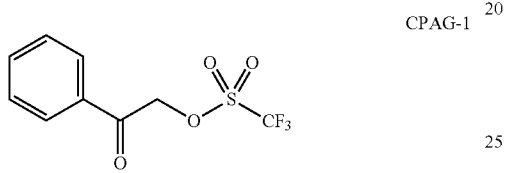

CPAG-1

This procedure was adopted from JPA2002236358. A 100 mL flask was charged with (diacetoxyiodo)benzene (Sigma-Aldrich) (3.22 g, 10.0 mmol, 1.0 eq.) and CH₃CN (25 mL) under nitrogen stream and the mixture was stirred for 5 minutes at room temperature. The CH3CN (25 mL) solution of trifluoromethanesulfonic acid (3.00 g, 20.0 mmol, 2.0 eq.) and H₂O (0.36 g, 20.0 mmol, 2.0 eq.) was added dropwise to the mixture over 5 minutes and the mixture was stirred for 10 minutes at room temperature. Acetophenone (1.20 g, 10.0 mmol, 1.0 eq.) was added to the mixture and the mixture was stirred for 2.5 hours at room temperature and the CH₃CN was removed in an evaporator. The residue was extracted with hexane (50 mL) twice and hexane layers were combined. The hexane was then removed in an evaporator. The crude product was purified by recrystallization (hexane, 35° C. to 0° C.) to obtain the target compound as white solid (0.113 g) in 4.2% yield. $^1$H-NMR (CDCl₃), delta (ppm): 5.68 (s, 2H), 7.57 (dd, J=8.0, 7.4 Hz, 2H), 7.71 (tt, J=1.2, 7.5 Hz, 1H), 7.92 (dd, J=1.3, 7.9 Hz, 2H). $^{19}$F-NMR (CDCl₃), delta in ppm, standard: $C_6F_6$=−162.2 ppm: −75.13 (s, 3F).

Example 25. Preparation of Comparative PAG, CPAG-2

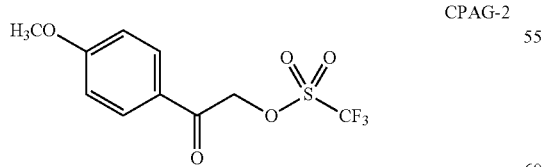

CPAG-2

A 100 mL flask was charged with (diacetoxyiodo)benzene (Sigma-Aldrich) (3.22 g, 10.0 mmol, 1.0 eq.) and CH₃CN (25 mL) under nitrogen stream and the mixture was stirred for 5 minutes at room temperature. A CH₃CN (25 mL) solution of trifluoromethanesulfonic acid (3.00 g, 20.0 mmol, 2.0 eq.) and H₂O (0.36 g, 20.0 mmol, 2.0 eq.) was added dropwise to the mixture over 5 minutes and the mixture was stirred for 30 minutes at room temperature. 4-Methoxyacetophenone (1.50 g, 10.0 mmol, 1.0 eq.) was added to the mixture and the mixture was stirred for 3.5 hours at room temperature. The mixture was concentrated in an evaporator. The residue was extracted with hexane (100 mL) twice and the hexane layers were combined. The combined hexane solution was concentrated in an evaporator. The crude product was purified by recrystallization (hexane/CHCl₃, 50° C. to 0° C.) to obtain the target compound as white solid (0.096 g) in 3.2% yield. $^1$H-NMR (CDCl₃), delta (ppm): 3.92 (s, 3H), 5.62 (s, 2H), 7.01 (d, J=9.0 Hz, 2H), 7.89 (d, J=9.0 Hz, 2H). $^{19}$F-NMR (CDCl₃), delta in ppm, standard: $C_6F_6$=−162.2 ppm: −75.27 (s, 3F).

Example 26. Preparation of Comparative PAG, CPAG-3

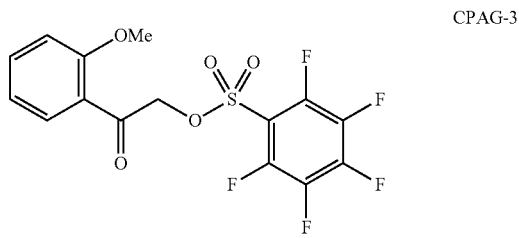 [SMILES: COc1ccccc1C(=O)COS(=O)(=O)c1c(F)c(F)c(F)c(F)c1F]

CPAG-3

A 50 mL flask was charged with 2-Hydroxy-2'-methoxy-acetophenone (SM-7) (0.8 g, 4.82 mmol, 1.0 eq.) and tetrahydrofuran (THF, 15 mL) under nitrogen stream in a dry ice acetone bath (ca. −78° C.). n-Butyl lithium in hexanes (3.0 mL of a 1.6M solution) was then added drop-wise and the mixture was allowed to stir for 30 minutes. Then 2,3,4,5,6-pentafluorobenzenesulfonyl chloride (Sigma-Aldrich) (1.285 g, 4.82 mmol, 1.0 eq.) dissolved in THF (5 mL) was added drop-wise to the reaction mixture. The mixture was stirred for 18 hours in an ice bath that was allowed to warm to room temperature. After 18 hours the reaction was twice extracted with 1M HCl (100 mL portions) and the organic portion dried over anhydrous MgSO₄ and dried in-vacuo. The resulting residue was then recrystallized from a minimum amount of CHCl₃ and excess hexanes. $^1$H NMR (400 MHz, Chloroform-d) δ 7.62-7.51 (m, 4H), 7.05 (t, J=7.1 Hz, 2H), 6.98 (d, J=8.3 Hz, 2H), 6.68 (s, 2H), 3.84 (s, 6H). $^{19}$F NMR (376 MHz, CDCl₃), delta in ppm: −134.17, −143.75, −158.75.

Example 27. Preparation of Comparative PAG, CPAG-4

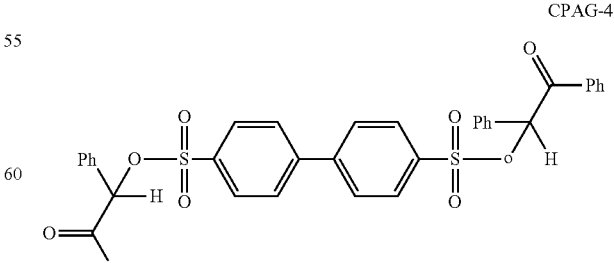

CPAG-4

Benzoin (Sigma-Aldrich) (7.64 g, 0.036 mole) and 4,4'-biphenylsulfonyl chloride (TCI) (7.02 g, 0.02 mole) were suspended in methyl ethyl ketone (30 mL) and the contents were cooled in an ice/water bath. Sodium hydroxide (1.8 g, 0.045 mole) in water (4.2 g) was added drop wise. After the addition, the mixture was stirred in the ice bath for 3 hours and was then warmed to room temperature and stirred for 17 hours. The mixture was filtered through a filter paper and the filterate was placed in the refrigerator. The precipitated solid was filtered and washed with 3×100 mL DI water followed by 50 mL cold methyl ethyl ketone. The solid was suction dried overnight to give 1.66 grams of the crude product. This solid was then recrystallized from ethyl acetate. $^1$H NMR (400 MHz, Chloroform-d), delta (ppm): 8.00-7.92 (d, 4H), 7.92-7.85 (d, 4H), 7.65-7.58 (d, 4H), 7.58-7.52 (t, 2H), 7.45-7.35 (m, 8H), 7.35-7.30 (m, 6H), 6.82 (s, 2H).

Example 28. Preparation of Comparative PAG, CPAG-5

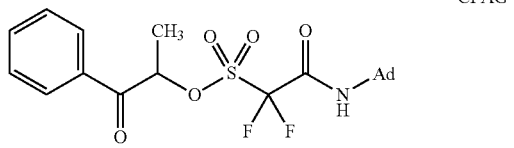

CPAG-5

A 100 mL flask was charged with 1, 1-Difluoro-2-oxo-2-(1-adamntylamino)ethanesulfonyl fluoride (SM-2) (1.62 g, 5.19 mmol, 1.0 eq.), 2-Hydroxypropiophenone (SM-10) (0.78 g, 5.19 mmol, 1.0 eq.) and THF (26 mL) under nitrogen stream and the mixture was stirred for 5 minutes at −50° C. n-BuLi (1.6 M, 3.2 mL, 5.19 mmol, 1.0 eq.) was added dropwise to the mixture over 10 minutes. The mixture was stirred for 2 hours at −50° C. to 10° C. 1N HCl (26 mL) was added to the final reaction mixture and then AcOEt (78 mL) was added. The upper layer was separated and the lower layer was extracted with AcOEt (52 mL) and then the organic solutions were combined. This solution was washed with 1N HCl (26 mL) and brine (26 mL) and the solution was subsequently dried over anhydrous MgSO$_4$ and filtered. Solvents were removed in an evaporator and then hexane (75 mL) was added to the residue and the mixture was stirred for 10 minutes at −50° C. The hexane was then removed by decantation. CHCl$_3$ (100 mL) was added to the residue and the solid remained was filtrated off. The filtrate was then concentrated in an evaporator. This crude product was partially purified by column chromatography (hexane/AcOEt) to obtain an oily material. Hexane (30 mL) was added to the concentrated oil and the mixture was stirred for 10 minutes at −50° C. Hexane was removed by decantation and CHCl$_3$ (30 mL) was added to the remaining material and filtrated. Filtrate was concentrated in an evaporator and the target PAG as colorless oil (0.22 g) in 9.6% yield was obtained. $^1$H-NMR (CDCl$_3$), delta (ppm): 1.73 (brs, 6H), 1.79 (d, J=7.0 Hz, 3H), 2.10 (brs, 6H), 2.15 (brs, 3H), 6.18 (q, J=7.1 Hz, 1H), 6.62 (drs, 1H), 7.55 (dd, J=7.4, 8.0 Hz, 2H), 7.68 (tt, J=1.3, 7.4 Hz, 1H), 7.95 (dd, J=1.3, 8.4 Hz, 2H), $^{19}$F-NMR (CDCl$_3$), delta in ppm, standard: C$_6$F$_6$=− 162.2 ppm: −106.89 (d, J=242.10, 1F), −109.19 (d, J=241.8 Hz, 1F).

PAG Thermal Stability

Table 2 summarizes the thermogravimetric analysis (TGA) data and differential scanning calorimetry (DSC) data for PAG-1 to PAG-11 and DPAG-1. $T_d$ TGA (° C.) is the main decomposition temperature according to TGA. Mp DSC (° C.) is the melting point. $T_d$ DSC (° C.) is the main decomposition temperature according to DSC.

TABLE 2

| Example | Name | $T_d$ TGA (° C.) | Mp DSC (° C.) | $T_d$ DSC (° C.) |
|---|---|---|---|---|
| 11 | PAG-1 | 155 | 109.7 | 140 |
| 12 | PAG-2 | 145 | 119.9 | 140 |
| 13 | PAG-3 | 155 | 150.1 | 160 |
| 14 | PAG-4 | 155 | 108.7 | 150 |
| 15 | PAG-5 | 115 | 127.4 | 130 |
| 16 | PAG-6 | 150 | 55.6 | 180 |
| 17 | PAG-7 | 140 | 131.5 | 140 |
| 18 | PAG-8 | 155 | 153.0 | 160 |
| 19 | PAG-9 | 130 | 136.6 | 140 |
| 20 | PAG-10 | 150 | — | 140 |
| 21 | PAG-11 | 150 | 111.9 | 145 |
| 22 | DPAG-1 | 150 | 112.7 | 130 |
| 23 | DPAG-2 | 180 | 118.4 | 175 |
| 24 (comp) | CPAG-1 | 120 | 54.6 | 120 |
| 25 (comp) | CPAG-2 | 170 | 72.0 | 140 |
| 26 (comp) | CPAG-3 | 140 | 80 | 110 |
| 27 (comp) | CPAG-4 | | | |
| 28 (comp) | CPAG-5 | 90 | | 120 |

Figure 3A:
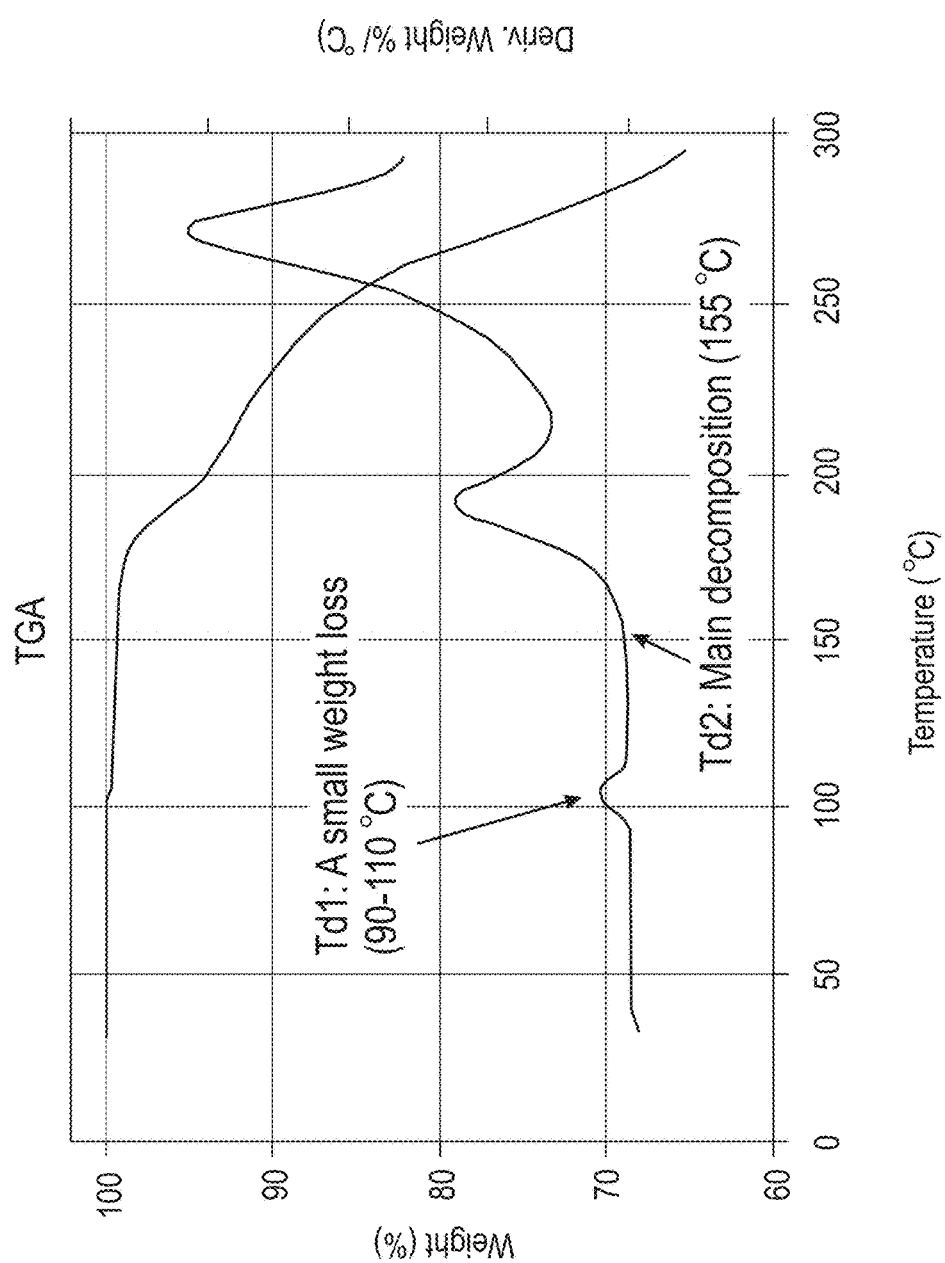
FIGS. 3A-3B are thermogravimetric analysis (TGA) and differential scanning calorimetry (DSC) curves, respectively, for PAG-1 (Example 11).
Figure 3B:
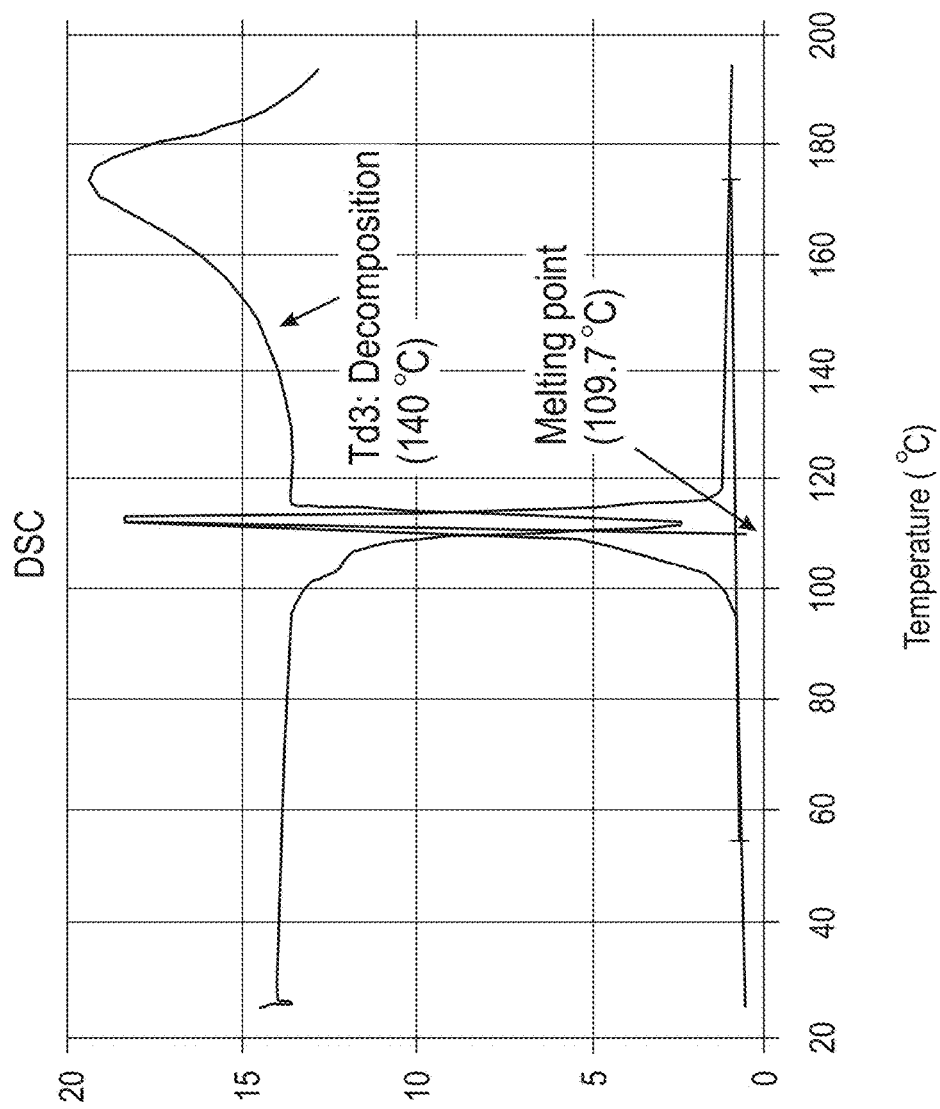

Examples 11-22 of Table 2 were relatively thermally stable. FIGS. 3A-3B show the TGA and DSC curves, respectively, for PAG-1 (Example 11). The melting point of PAG-1, according to DSC, was about 109.7° C. (FIG. 3B). At this temperature (Td1), there was a small weight loss in the corresponding TGA (FIG. 3B). This small weight loss at the melting point was observed with all the phenacyl PAGs made. The weight loss was attributed to a physical change (water evaporation, sublimation, etc.). The main decomposition starts around 140° C. (Td2, Td3) indicating the increased thermal stability of this PAG.

Figure 4A:
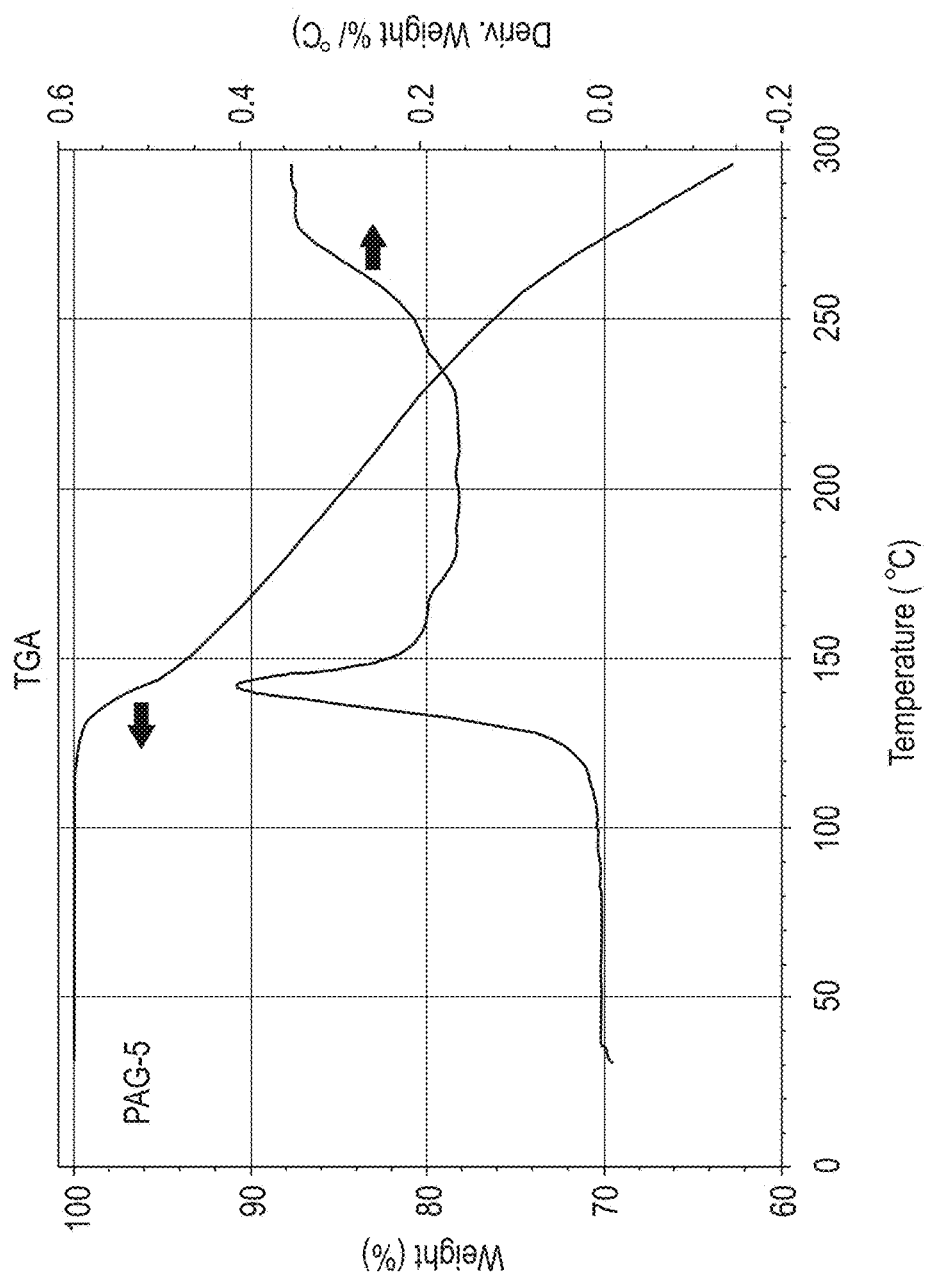
FIG. 4A is a graph showing the TGA curves for PAG-5 (Example 15).
Figure 4B:
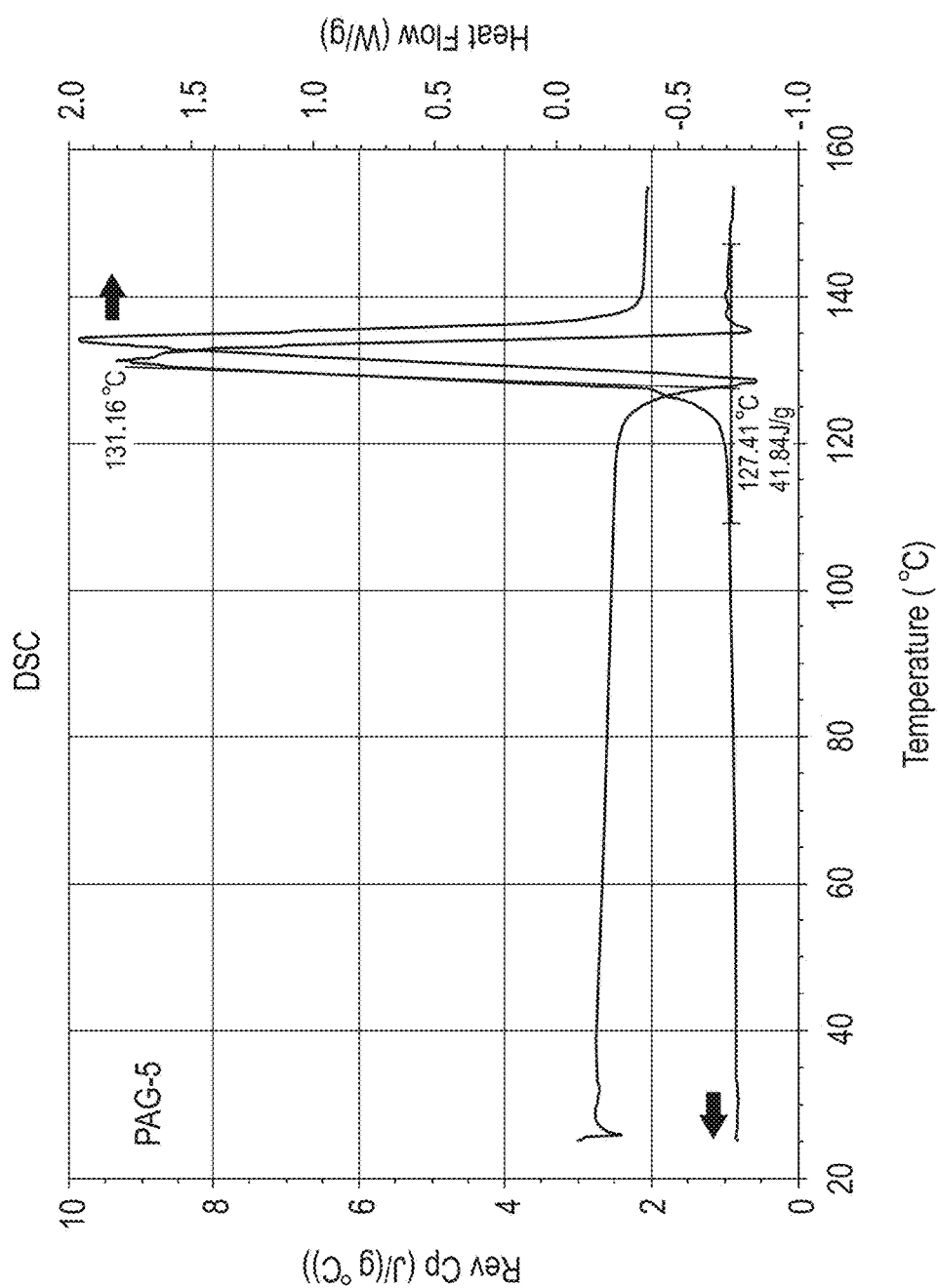
FIG. 4B is a graph showing the DSC curves for PAG-5 (Example 15).

FIG. 4A is a graph showing the TGA curve for PAG-5 and indicates the degradation temperature (where PAG-5 experiences a 5 wt. % loss) occurs at about 140° C. followed by a continual weight loss to 62 wt % at 300° C. FIG. 4B is a graph showing a DSC curve heating curve for PAG-5 indicating a large increase in the heat flow at 131° C. consistent with a melting point of PAG-5.

Figure 5A:
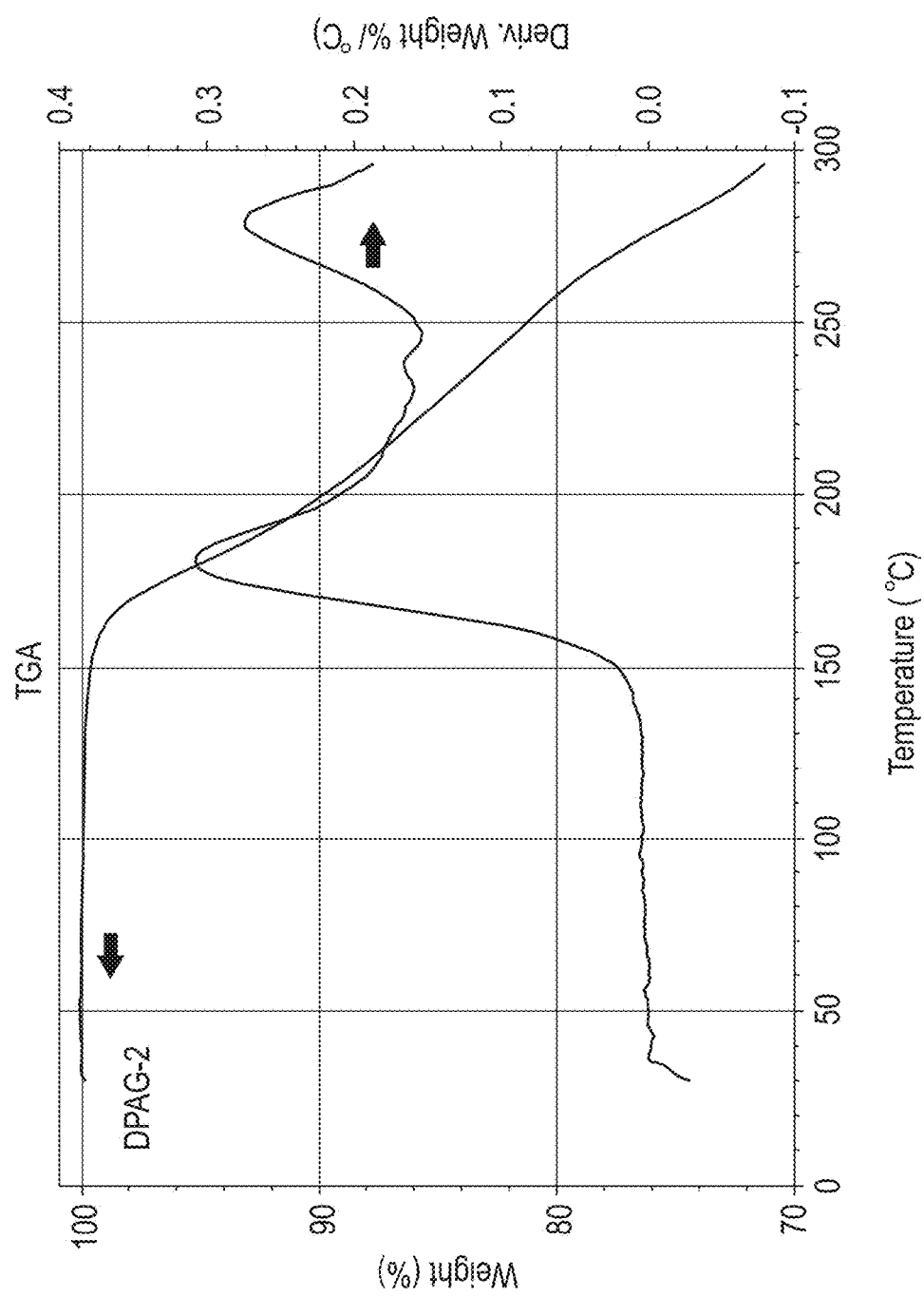
FIG. 5A is a graph showing the TGA curves for DPAG-2 (Example 23).
Figure 5B:
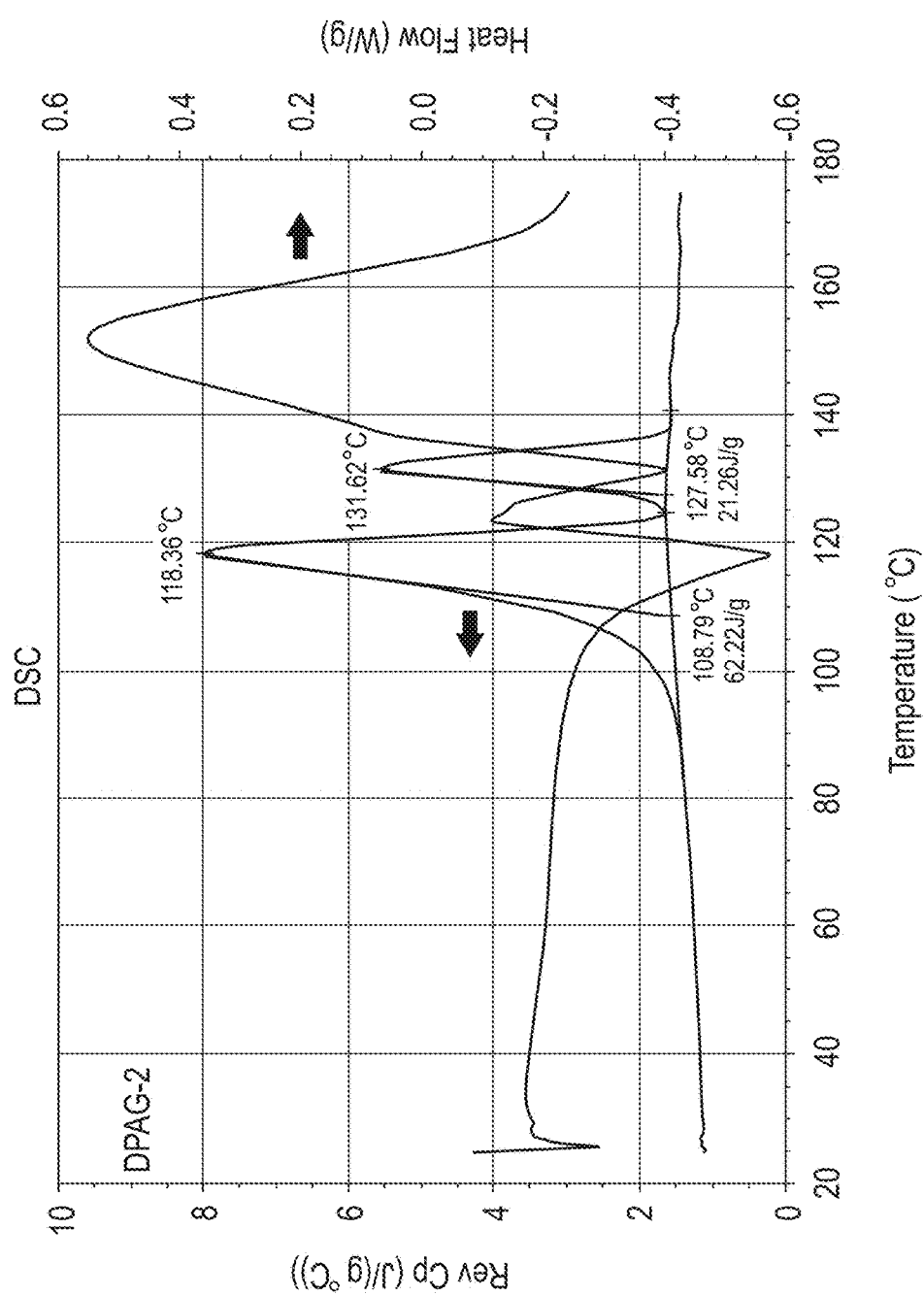
FIG. 5B is a graph showing the DSC curves for DPAG-2 (Example 23).

FIG. 5A is a graph showing the TGA curve for DPAG-2 and indicates the degradation temperature (where DPAG-2 experiences a 5 wt. % loss) occurs at ca. 175° C. followed by a continual weight loss to ca. 70 wt. % of the original weight at 300° C. FIG. 5B shows DSC heating curves for DPAG-2 indicating a large increase in the heat flow at 118° C. consistent with a melting point of DPAG-2 as well as a second thermal transition observed at 132° C.

Figure 6A:
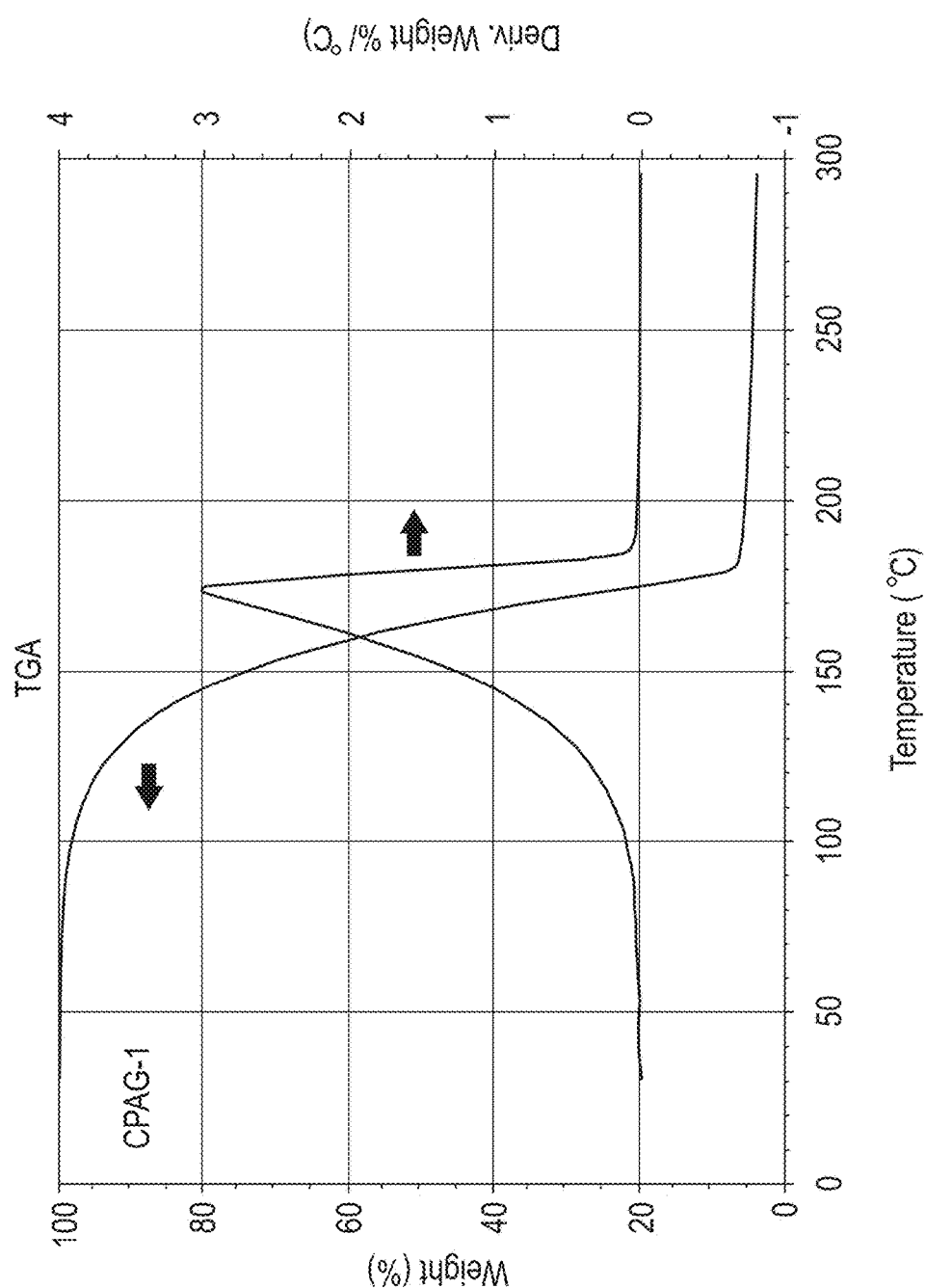
FIG. 6A is a graph showing the TGA curves for CPAG-1 (Example 24, comparative).
Figure 6B:
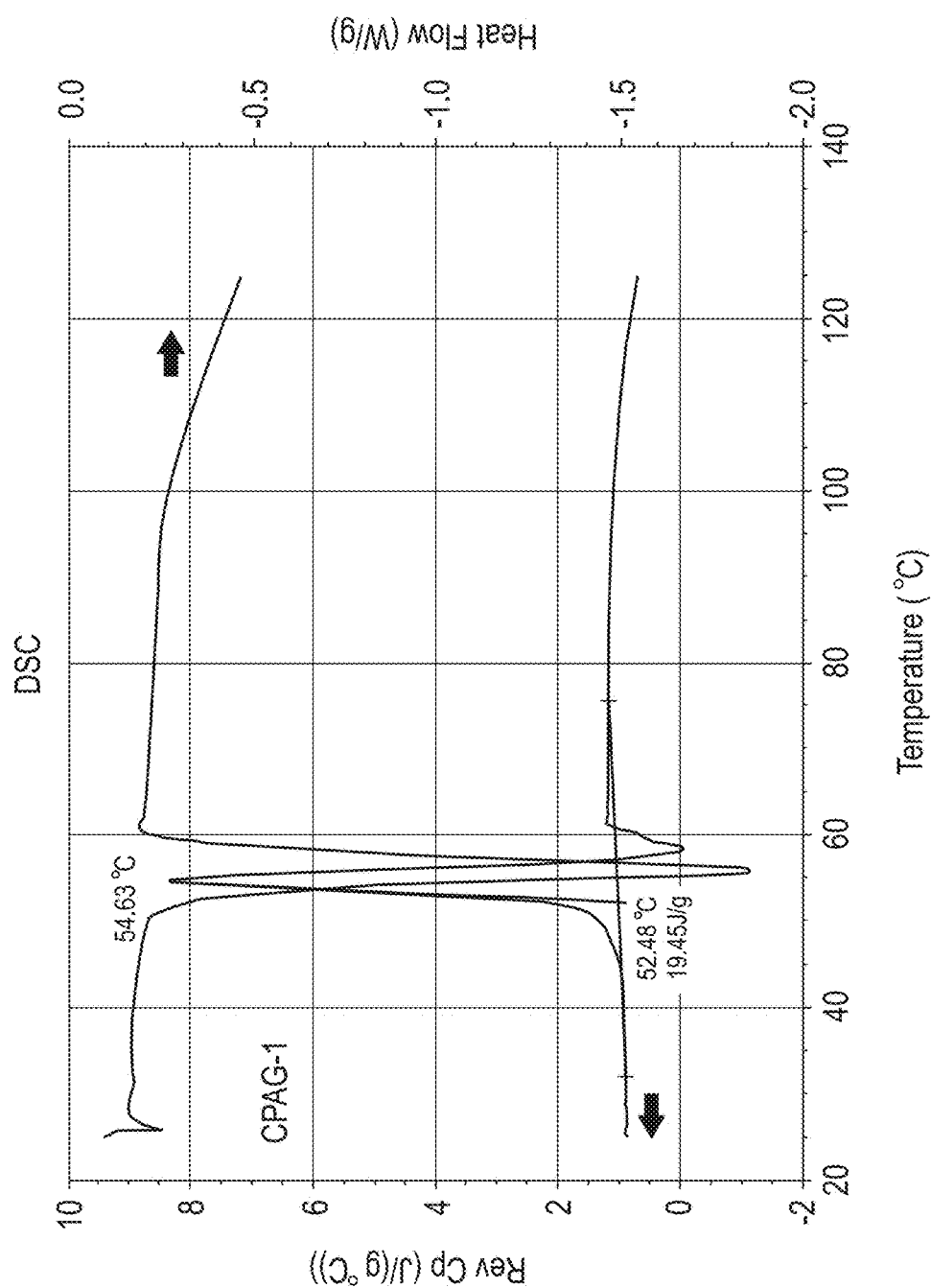
FIG. 6B is a graph showing the DSC curves for CPAG-1 (Example 24, comparative).

FIG. 6A is a graph showing the TGA curve for CPAG-1 and indicates a sharp degradation temperature, where CPAG-1 experiences a 5 wt. % loss at ca. 120° C., followed by a continual weight loss to nearly 0 wt. % of the original weight at 300° C. FIG. 6B shows DSC curves for CPAG-1 indicating a large increase in the heat flow at 54° C. consistent with a melting point of CPAG-1.

Polymer Synthesis

A standard acid-labile polymer, P(NBHFAMA-co-ECPMA) 60:40 m/m, was used as the base polymer in the formulations for the evaluation of the PAGs. End groups are not shown in the structure below.

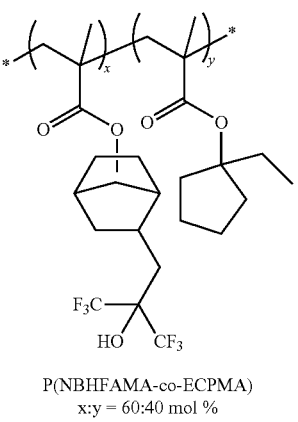

P(NBHFAMA-co-ECPMA)
x:y = 60:40 mol %

Example 29

Preparation of acid-labile polymer P-1. NBHFAMA (10.80 grams, 0.03 mole), ECPMA (3.64 grams, 0.02 mole), and 58 grams of tetrahydrofuran (THF) were placed in a round bottom flask equipped with a condenser and a nitrogen inlet. To this solution, 2,2'-azobisisobutyronitrile (AIBN) (0.33 gram, 0.002 mole) and 1-dodecanethiol (0.30 gram, 0.0015 mole) were added and stirred until dissolved. Then the solution was degassed using four vacuum/nitrogen purges. The solution was then heated at 70° C. in an oil bath for 18 hours. Afterwards, the solution was added drop-wise into hexanes (1.2 liter). The precipitated polymer was filtered through a medium frit funnel, washed with 100 mL hexanes, and dried under suction. The polymer was then dried in a vacuum oven at 60° C. Yield: 5.06 grams. Mw 11890; Mn 9355; polydispersity (PDI): 1.27; Tg: 150.8° C.

Resist Formulations

Resist compositions were prepared by forming a 3.5 wt % (weight %) solution, based on total weight of the solution, in propylene glycol monomethyl ether acetate (PGMEA) containing 100 parts polymer P(NBHFAMA-co-ECPMA) 60:40, 4 to 5 parts of PAG, and 0.33 or 0.66 parts of an organic base, 2-phenyl benzimidazole (quencher 1). The solution was then filtered through 0.2 micrometer PTFE syringe filter. The formulations were not optimized.

Examples 12-22 were stable in the resist formulations. PAG-1 (Example 11) and comparative PAGs CPAG-1 (Example 24), CPAG-2 (Example 25), and CPAG-5 (Example 28) were not stable in resist formulation. For example, the resist formulation with CPAG-5 decomposed within one week, indicating that an alkyl or aryl group substituent at the alpha-position of the aryl ketone group makes the PAG less stable.

Line Patterns

The resist formulation was spin coated to a thickness between 30 to 50 nm onto silicon wafers having a bottom anti-reflective coating (BARC). The BARC underlayer was used for adhesion purposes. The wafer was given a post-apply bake at 110° C. for 60 seconds on a hot plate. The PAGs were evaluated at 193 nm (193 nm interference lithography) and/or EUV (EUV-MET). For EU, the wafer was exposed on a 0.3-NA extreme ultraviolet (EUV) micro exposure tool (MET) at variable doses. The exposed wafer was given a post-exposure bake at 110° C. for 60 seconds. Both bakes were done with the wafer in contact with the hot plate. A 60-second development of the resist was carried out using a gentle spray of 0.26 N aqueous tetramethylammonium hydroxide solution (TMAH) to puddle followed by water rinse and spin dry. Top and cross-sectional images were inspected using a LEO Carl Zeiss scanning electron micrograph (SEM) tool. Cross sectional samples were coated with thin PdAu to avoid sample charging.

Results

Figure 7:
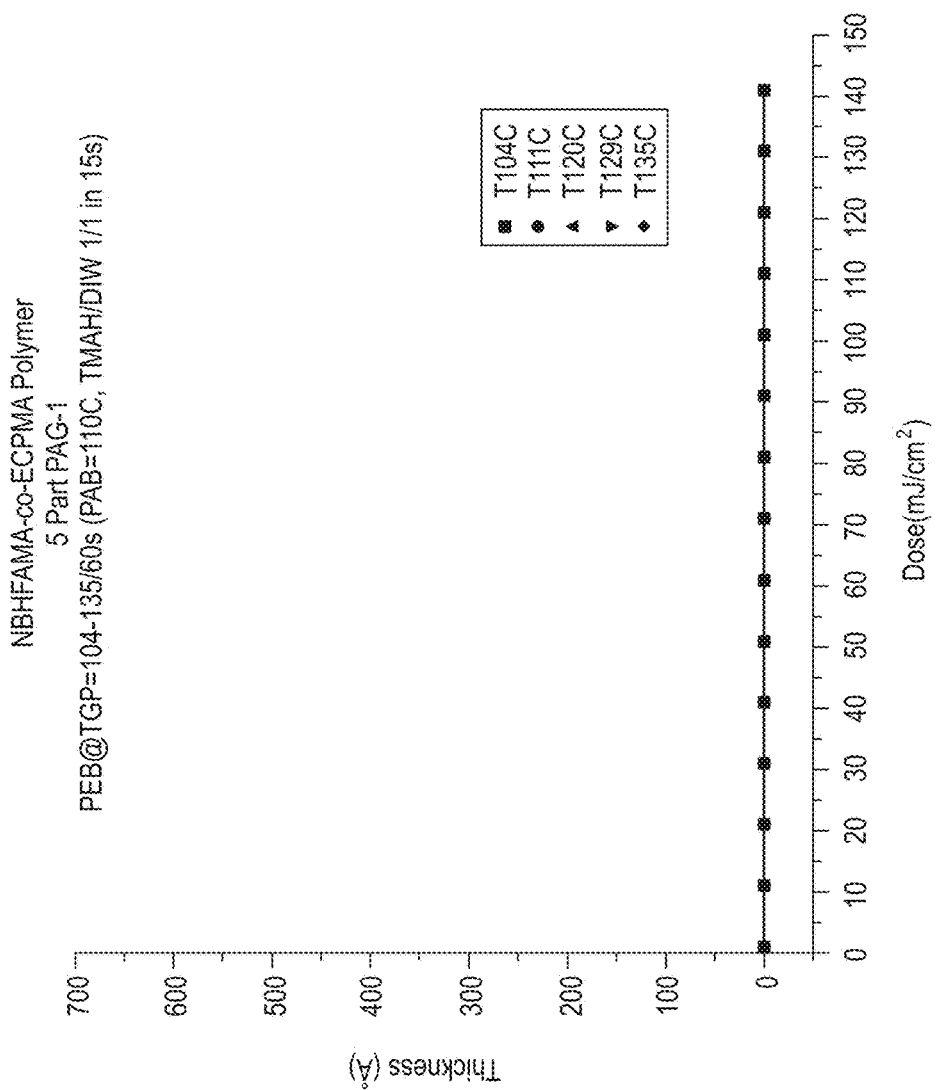
FIG. 7 is a graph showing the contrast curves for a positive resist formulation with PAG-1. The formulation was unstable in spite of the moderate thermal stability of this PAG. Irrespective of the dose, the resist film completely dissolved (no contrast).

FIG. 7 is a graph showing the contrast curves for a positive resist formulation with PAG-1. The formulation was unstable in spite of the moderate thermal stability of this PAG. Irrespective of the dose, the resist film completely dissolved (no contrast).

Figure 8A:
FIGS. 8A-8C are scanning electron micrographs (SEMs) images at magnifications 48x, 10000x, and 50000x, respectively, of a line pattern prepared with 4 parts CPAG-3 (comparative PAG compound) and 0.66 parts quencher 1 (resist layer film thickness=68 nm, exposure wavelength=193 nm, dose=5.8 mJ, 60 nm half-pitch (HP) variable prism). The line pattern showed scum and lifting.
Figure 8B:
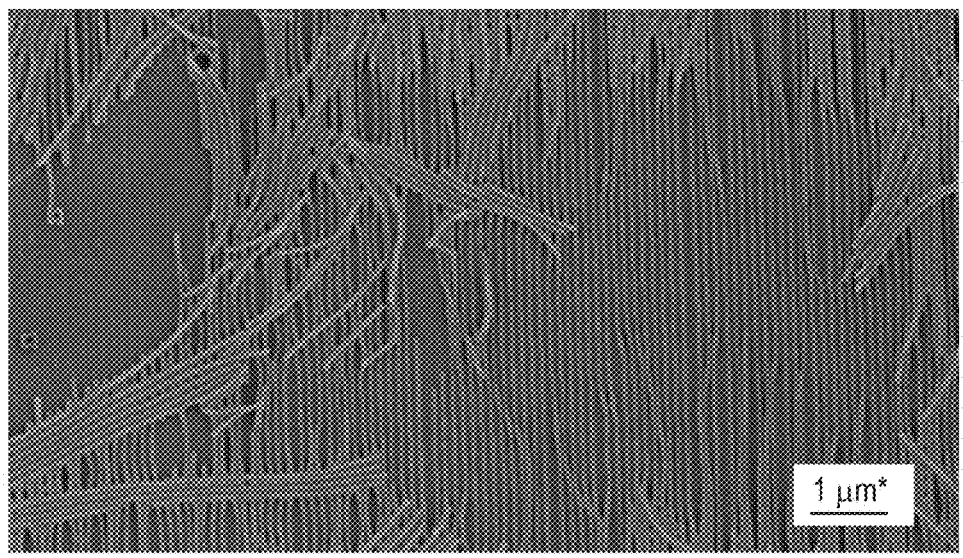
Figure 8C:
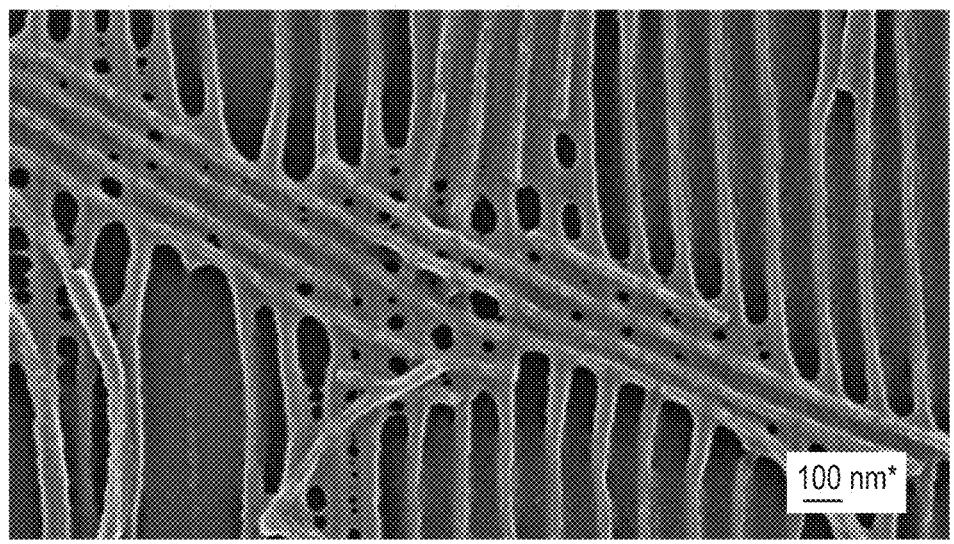
Figure 9A:
FIGS. 9A-9C are SEM images at magnifications 48x, 10000x, and 50000x, respectively, of a line pattern prepared formed with a resist formulation containing 4 parts CPAG-3 (comparative) and 0.66 parts quencher 1 (resist film thickeness=68 nm, exposure wavelength=193 nm, dose=10.7 mJ, 65 nm half-pitch (HP) variable prism). The resulting line pattern showed scum and lifting.
Figure 9B:
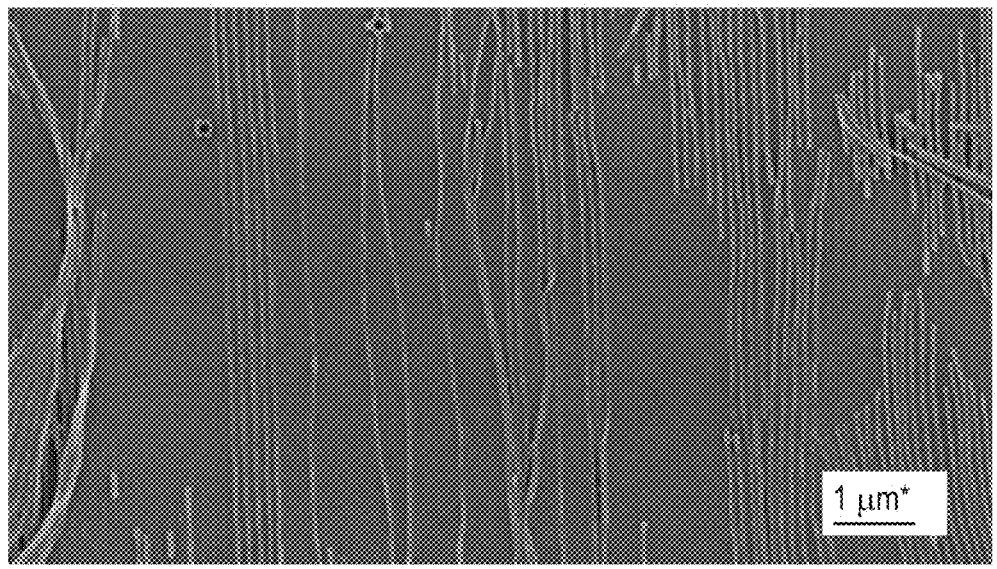
Figure 9C:
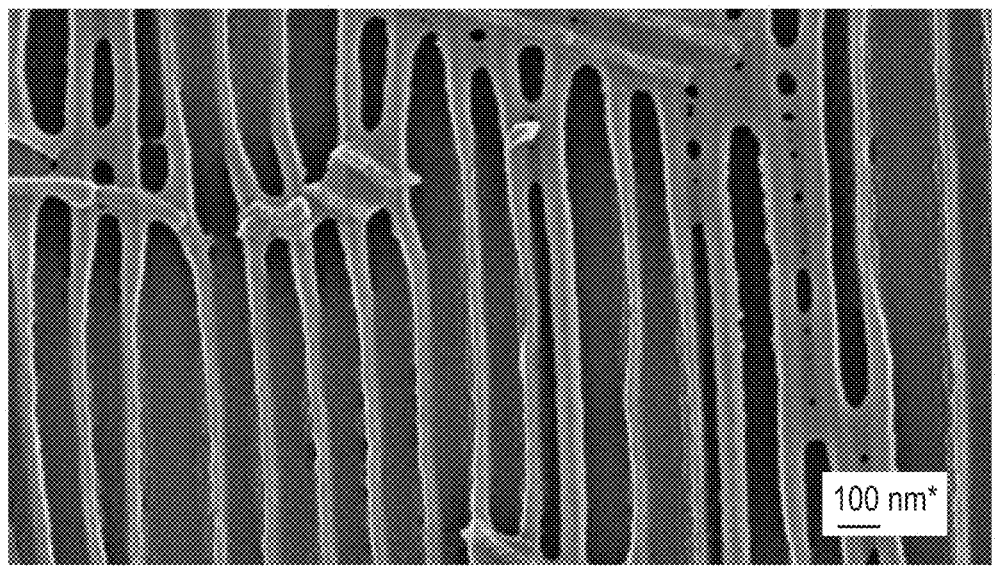

FIGS. 8A-8C are scanning electron micrographs (SEMs) images at magnifications 48×, 10000×, and 50000×, respectively, of a line pattern prepared with comparative PAG compound, CPAG-3. The resist formulation contained 4 parts CPAG-3 and 0.66 parts quencher 1. The resist layer was exposed using dry 193 nm interference lithography tool, 60 nm half pitch (HP) variable prism, and a dose 5.8 mJ. The line pattern showed scum and lifting. Similar results were observed for dose 10.7 mJ (FIGS. 9A-9C, SEMs). The poor performance is attributed to high volatility and diffusion of the photo-generated pentafluorophenyl sulfonic acid.

Figure 10:
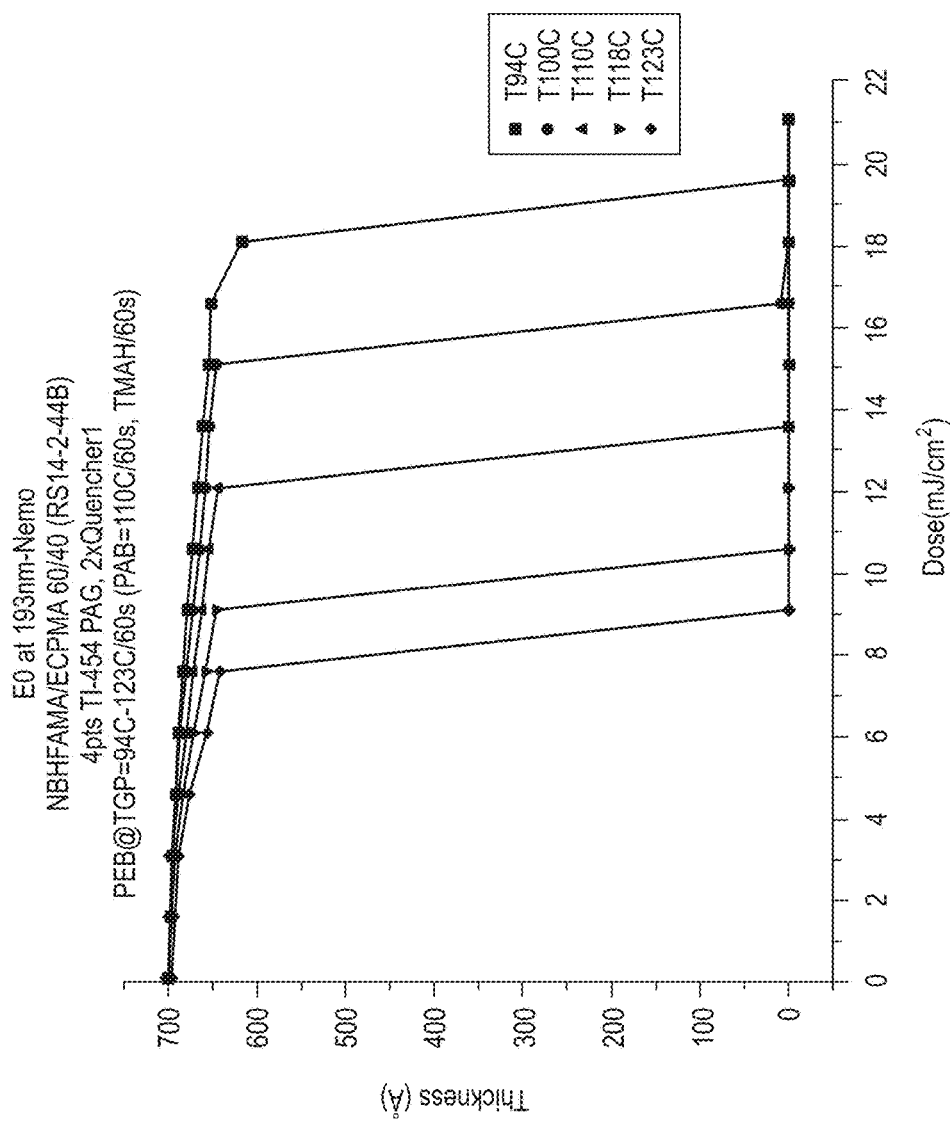
FIG. 10 is a graph showing the contrast curves obtained with PAG-5 imaged at 193 nm (dry, 193 nm interference lithography), resist layer film thickness=70 nm, 0.66 parts quencher 1.
Figure 11:
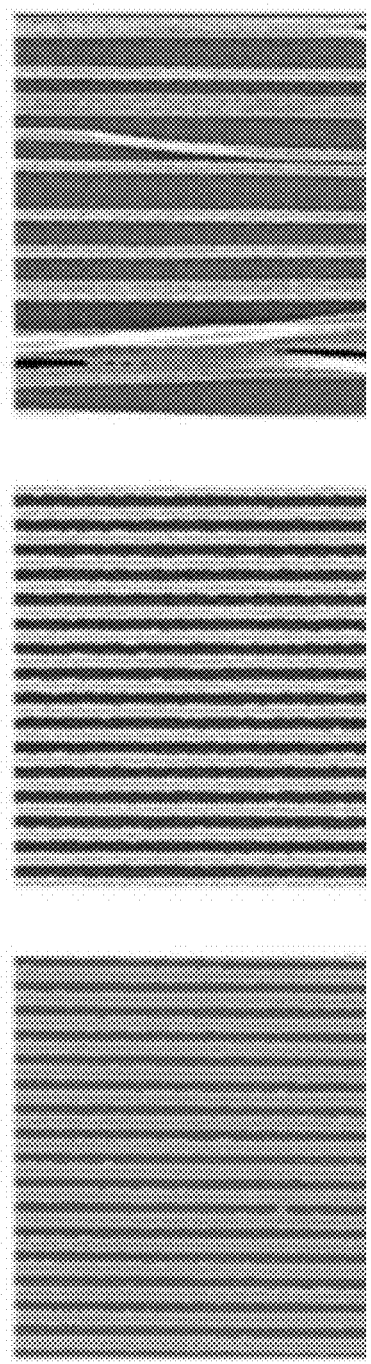
FIGS. 11A-11C are SEMs of an 80 nm HP line patterns formed using doses 5.1 mJ, 5.9 mJ, and 6.4 mJ, respectively, with resist layers containing PAG-5.

FIG. 10 is a graph showing contrast curves obtained with PAG-5. The resist layer (70 nm film thickness (FT)) contained 0.66 parts quencher 1 and was imaged using dry 193 nm interference lithography. FIGS. 11A-11C are SEMs of an 80 nm HP line patterns formed using doses 5.1 mJ, 5.9 mJ, and 6.4 mJ, respectively, with the resist formulation containing PAG-5.

Figure 12:
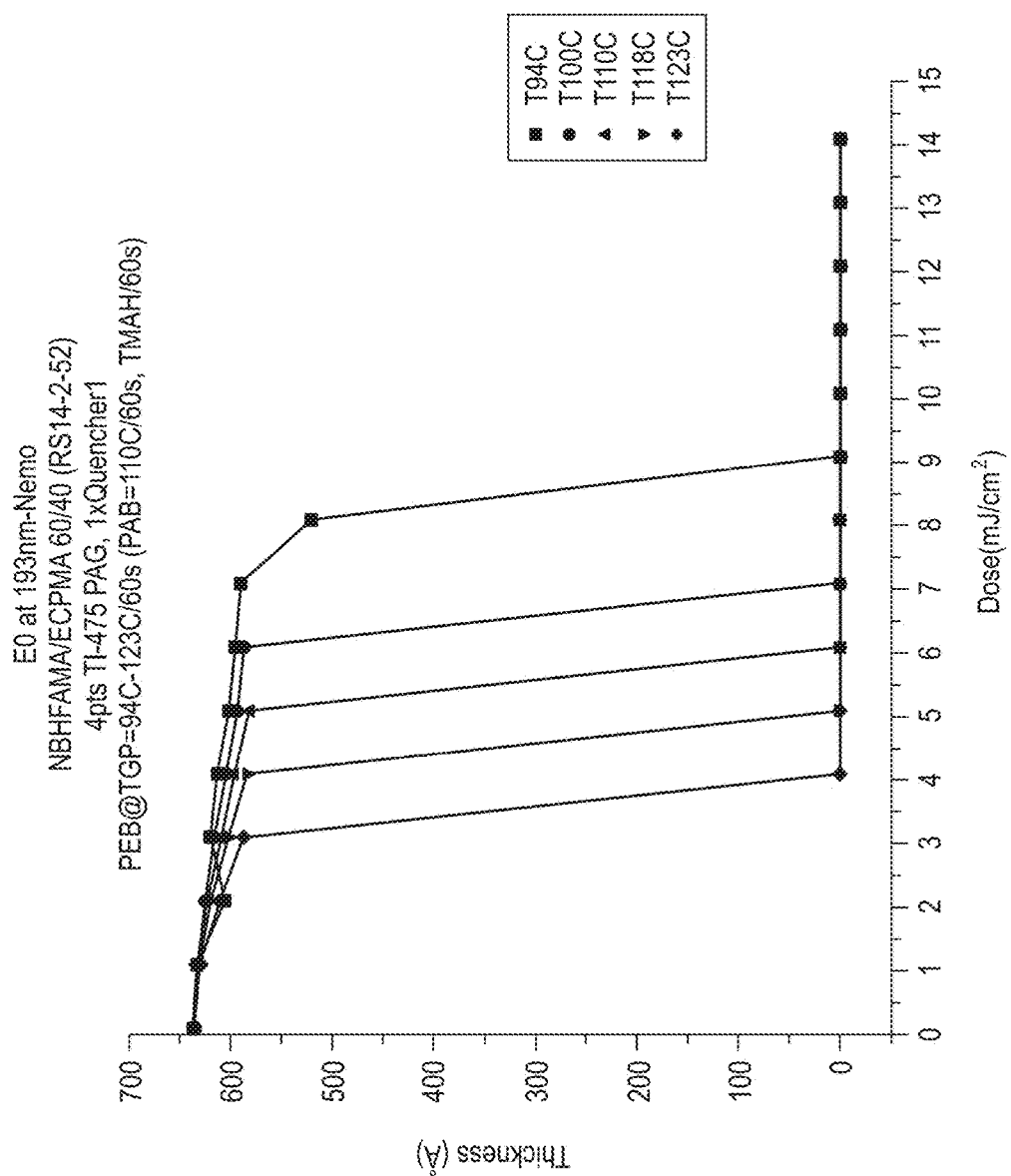
FIG. 12 is a graph showing the contrast curves obtained for a resist layers formed with PAG-9. The resist layer (film thickness ~70 nm) contained 0.33 parts quencher 1 and was imaged using dry 193 nm interference lithography.
Figure 14C:
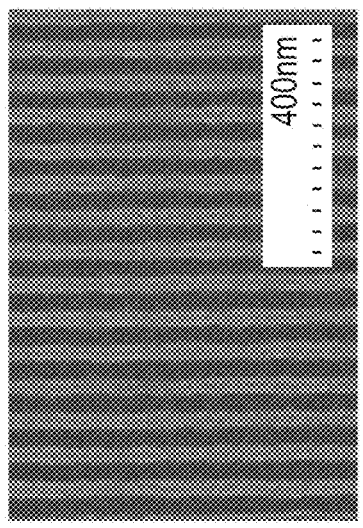
FIGS. 14A-14E are SEMs of line patterns having half pitch 28 nm, 30 nm, 32 nm, 34 nm, and 36 nm, respectively, obtained with resist layers containing PAG-9, exposed at 13.5 nm (EUV-MET), dose 16.00 mJ.
Figure 14B:
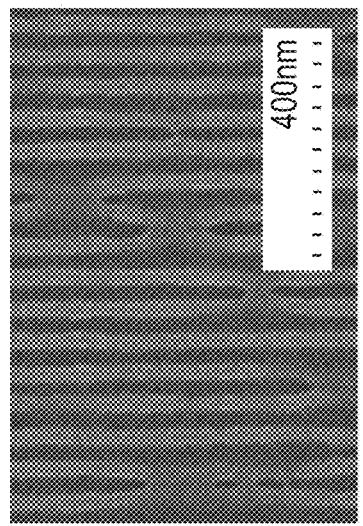
Figure 14E:
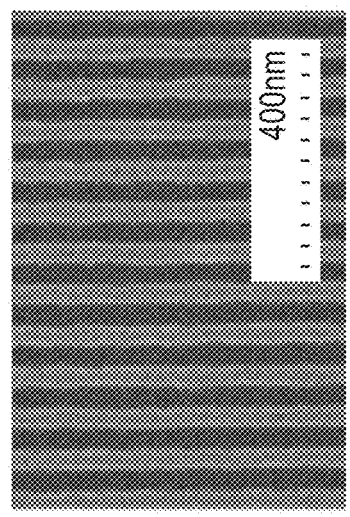
Figure 14D:
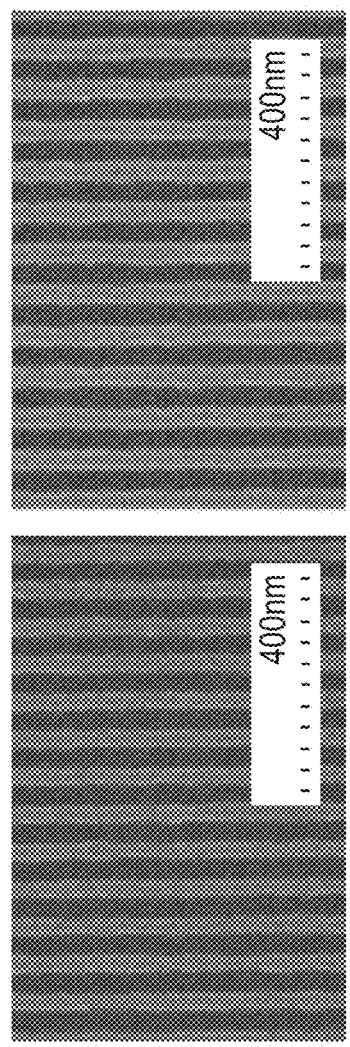
Figure 14A:
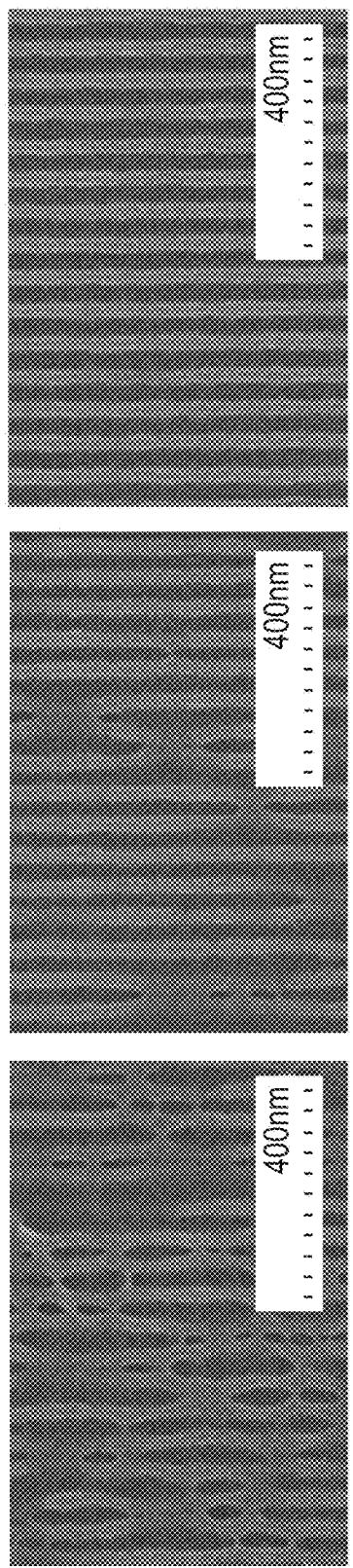

FIG. 12 is a graph showing contrast curves obtained with PAG-9. The resist layer (~70 nm FT) contained 0.33 parts quencher 1 and was imaged using dry 193 nm interference lithography. FIGS. 13A-13D are SEMs of 80 nm HP line patterns obtained with PAG-9 at doses of 5.1 mJ, 5.9 mJ, and 6.4 mJ, respectively.

The results indicate that the adamantyl substituted PAG-9 performed better than the phenyl substituted PAG-5 under identical conditions.

FIGS. 14A-14E are SEMs of line patterns having HP 28 nm, 30 nm, 32 nm, 34 nm, and 36 nm, respectively, obtained with PAG-9 using 13.5 nm EUV exposures (EUV-MET) at a dose of 16.00 mJ.

Figure 15:
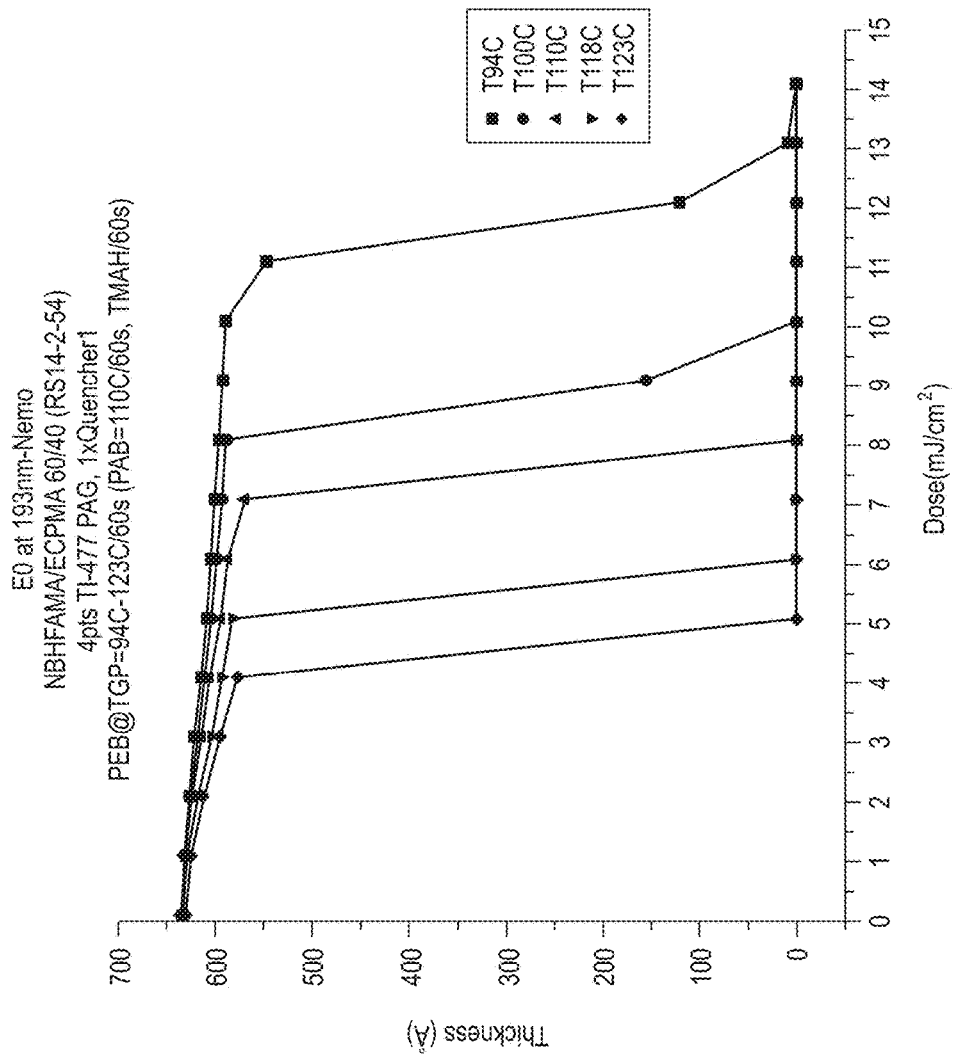
FIG. 15 is a graph showing contrast curves obtained with resist layers containing PAG-9. The resist layer (film thickness ~70 nm) contained 0.33 parts quencher 1 and was imaged using dry 193 nm interference lithography.

FIG. 15 is a graph showing contrast curves obtained with PAG-9. The resist layer (~70 nm FT) contained 0.33 parts quencher 1 and was imaged using dry 193 nm interference lithography. FIGS. 16A-16F are SEMs of 80 nm HP line patterns obtained with doses of 9.5 mJ, 10.4 mJ, 11.5 mJ, 12.4 mJ, 14.4 mJ, and 13.5 mJ, respectively, of resist layers containing PAG-9.

Figure 17:
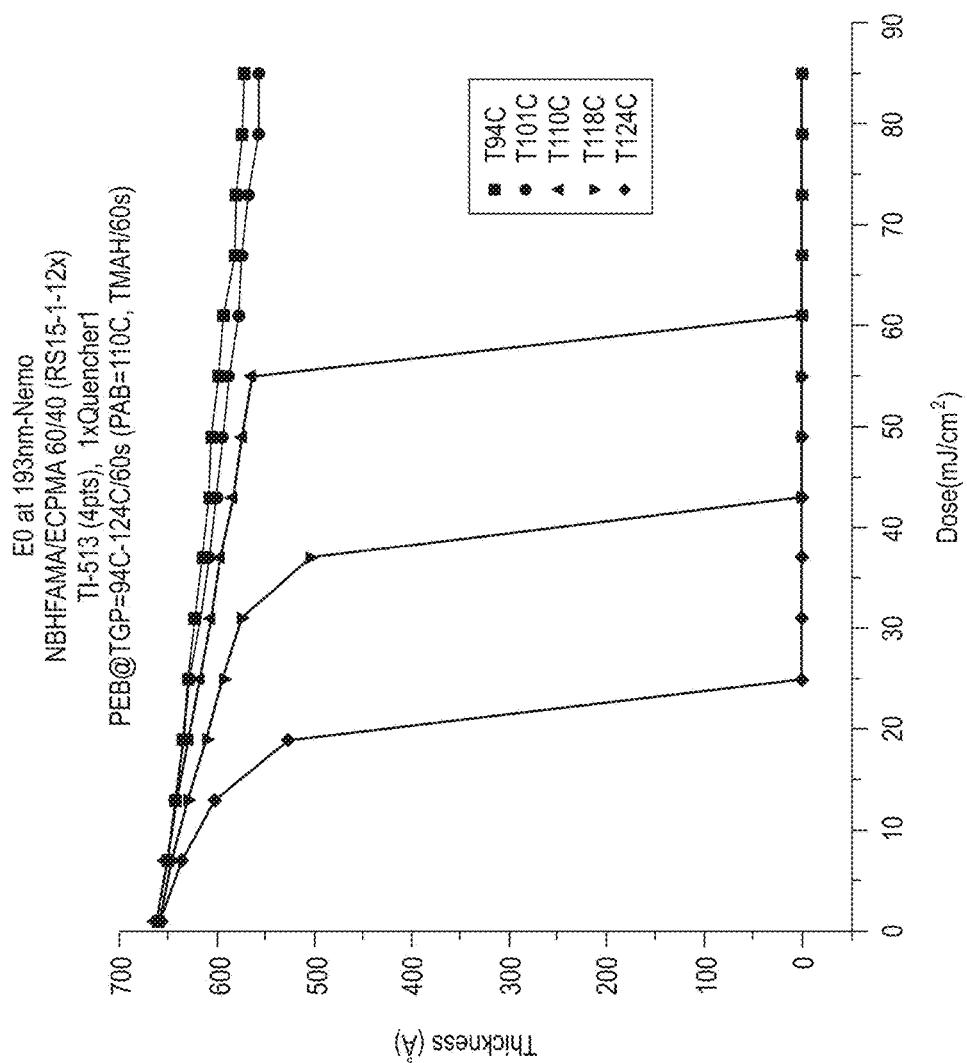
FIG. 17 is a graph showing contrast curves obtained with resist layers comprising PAG-11. The resist layer (film thickness ~67 nm) contained 0.33 parts quencher 1 and was imaged using dry 193 nm interference lithography.
Figure 18:
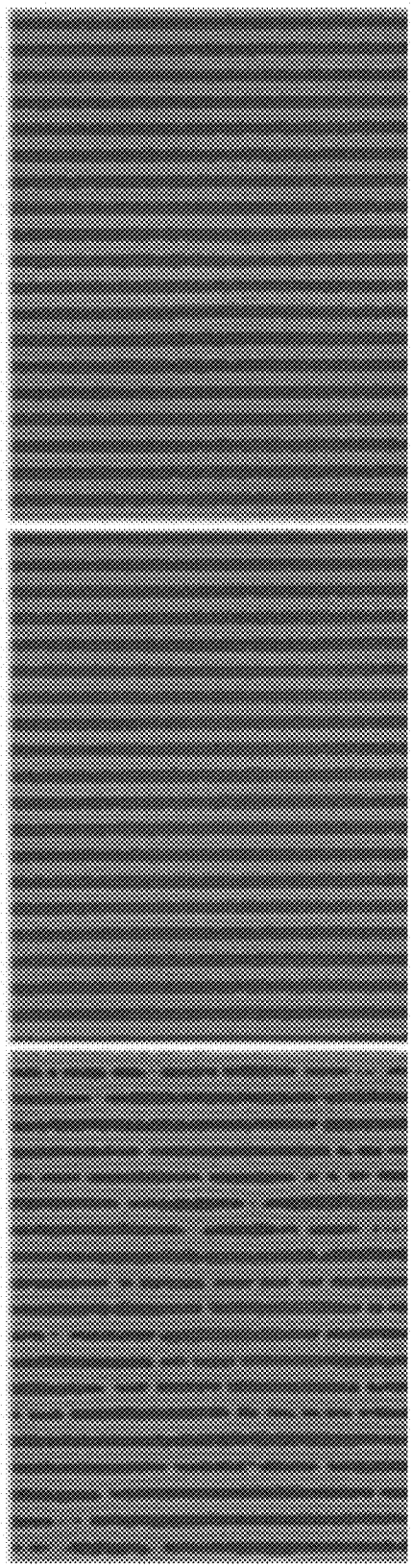
FIGS. 18A-18C are SEMs of 60 nm HP line patterns obtained with doses of 36.5 mJ, 37.0 mJ, and 38.5 mJ, respectively, of resist layers containing PAG-11.

FIG. 17 is a graph showing contrast curves obtained with PAG-11. The resist layer (~67 nm FT) contained 0.33 parts quencher 1 and was imaged using dry 193 nm interference lithography. FIGS. 18A-18C are SEMs of 60 nm HP line patterns obtained with doses of 36.5 mJ, 37.0 mJ, and 38.5 mJ, respectively of resist layers containing PAG-11.

Figure 19:
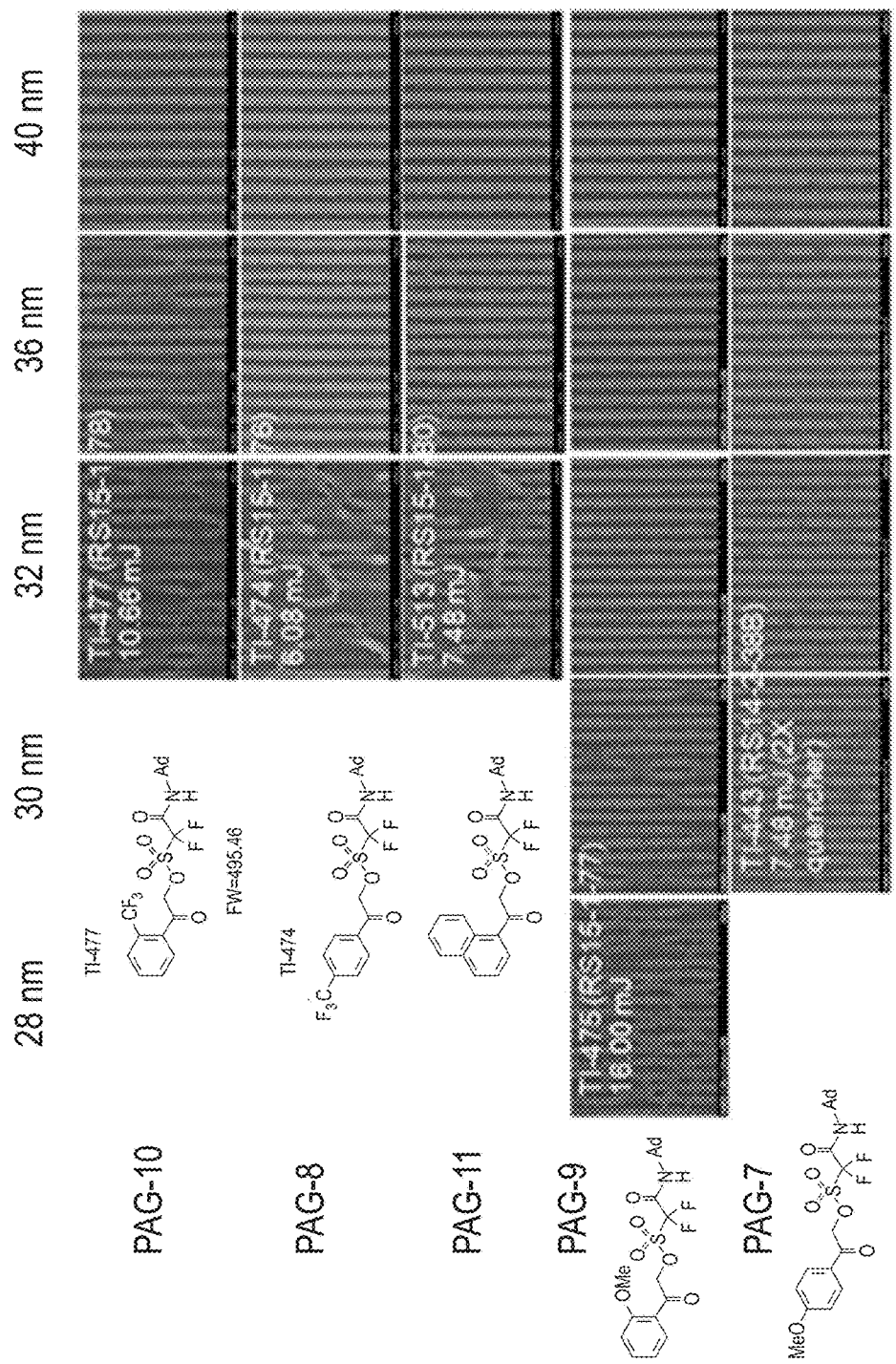
FIG. 19 is a set of SEMs comparing the performance of adamantyl substituted PAG-7, PAG-9, PAG-11, PAG-8 and PAG-10 having different substituents in the phenacyl group. Imaging was at 13.5 nm (EUV-MET, rotated dipole illumination, 0.3 numerical aperture).

FIG. 19 is a set of SEMs comparing the performance of adamantyl substituted PAG-7, PAG-9, PAG-11, PAG-8 and PAG-10 having different substituents in the phenacyl group. Imaging was at 13.5 nm using the EUV-MET tool (rotated dipole illumination, 0.3 numerical aperture). All of the formulations were stable during the evaluation period (about 1 week) at room temperature. The resist layers (~40 nm FT) contained 0.33 parts quencher 1 (0.66 parts quencher 1 for PAG-5). The half pitch varied from 28 nm to 40 nm. However, the performance appears to be better with MeO (bulky and electron donating) substituted PAGs than the CF3 (bulky and electron withdrawing) substituted PAGs.

FIGS. 20A-20D are SEMs of line patterns having HP 30 nm, 32 nm, 36 nm, and 406 nm, respectively, obtained with DPAG-2 imaged at 13.5 nm using the EUV-MET. The dose was 45.8 mJ. The resist layers (~40 nm FT) contained 0.99 parts quencher 1. Each line pattern showed scum and lifting.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A compound of formula (3):

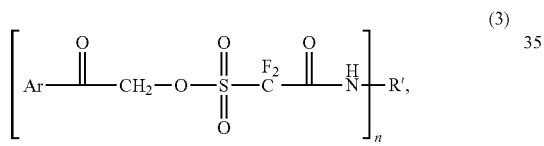

(3)

wherein
n is 1,
Ar is a monovalent aryl radical selected from the group consisting of

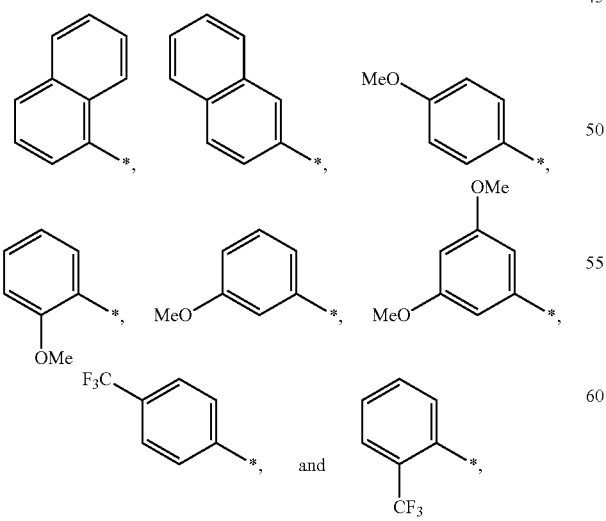

and
R' is 1-adamantyl.

2. The compound of claim 1, wherein Ar is

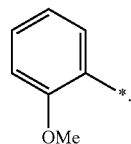

3. The compound of claim 1, wherein Ar is

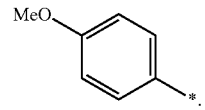

4. The compound of claim 3, wherein Ar is

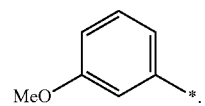

5. The compound of claim 4, wherein Ar is

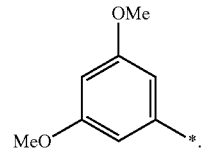

6. The compound of claim 3, wherein Ar is

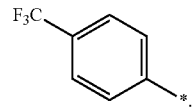

7. The compound of claim 3, wherein Ar is

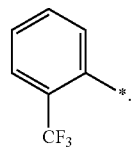

8. The compound of claim 7, wherein Ar is

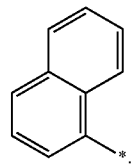

9. The compound of claim 1, wherein Ar is

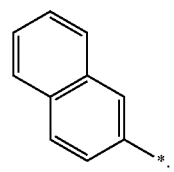

10. A compound of formula (3):

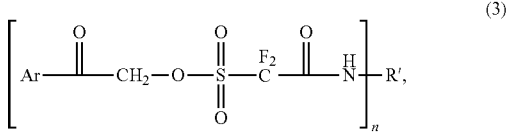

wherein
n is 2,
Ar is a monovalent aryl radical selected from the group consisting of

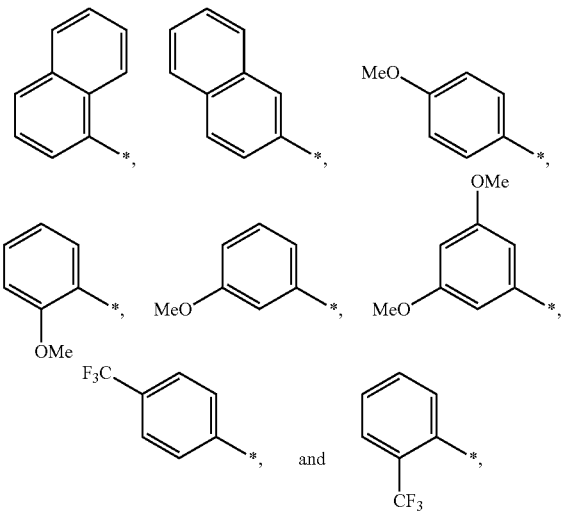

R' is 1,6-hexylene (*—CH$_2$(CH$_2$)$_4$CH$_2$—*).

11. The compound of claim 10, wherein Ar is

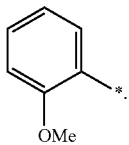

12. The compound of claim 11, wherein Ar is

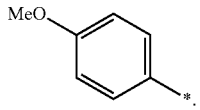

13. A resist formulation, comprising:
a solvent;
a resin capable of chemical amplification;
a base quencher; and
the PAG compound of claim 1;
wherein
the resin, the base quencher, and the PAG compound are in contact with the solvent, and
the resist formulation is suitable for use in a lithographic process.

14. The resist formulation of claim 13, wherein the resist formulation is positive-tone.

15. The resist formulation of claim 13, wherein the resist formulation is negative-tone.

16. The resist formulation of claim 13, wherein the PAG compound is capable of forming an acid when exposed to radiation.

17. The resist formulation of claim 15, wherein the radiation is selected from the group consisting of electron beam, deep ultraviolet light, and extreme ultraviolet light.

18. The resist formulation of claim 13, wherein the PAG compound is capable of forming an acid when heated to a temperature of about 150° C. or higher.

19. A method, comprising:
casting a resist formulation comprising a solvent, a resin capable of chemical amplification, a base, and the PAG compound of claim 1 on a surface of a substrate and removing the solvent, thereby forming a layered structure, the layered structure comprising a resist layer disposed on the surface of the substrate, the resist layer comprising the resin, the base quencher, and the PAG compound;
optionally baking the resist layer;
exposing the resist layer pattern-wise to radiation, thereby forming an exposed resist layer comprising exposed regions and non-exposed regions of the exposed resist layer, the exposed regions of resist layer comprising an acid formed by exposing the PAG compound to the radiation;
heating the exposed resist layer, thereby forming a heated exposed resist layer comprising heated exposed regions of the exposed resist layer and heated non-exposed regions of the exposed resist layer, wherein the heated exposed regions have greater solubility in a given alkaline developer compared to the heated non-exposed regions; and
selectively removing the heated exposed regions using the given alkaline developer, thereby forming a patterned resist layer disposed on the surface of the substrate, the patterned resist layer comprising the heated non-exposed regions of the heated exposed resist layer.

20. The method of claim 19, comprising transferring the patterned resist layer to the substrate.

21. The method of claim 19, comprising heating the patterned resist layer at a temperature effective in forming an acid by a thermal reaction of the PAG compound, thereby forming a patterned resist layer that is soluble in the given alkaline developer.

22. A method, comprising:
casting a resist formulation comprising a solvent, a resin capable of chemical amplification, a base, and the PAG compound of claim 1 on a surface of a substrate and removing the solvent, thereby forming a layered structure comprising a resist layer disposed on the surface of the substrate, the resist layer comprising the resin, the base quencher, and the PAG compound;
optionally baking the resist layer;
exposing the resist layer pattern-wise to radiation, thereby forming an exposed resist layer comprising exposed regions and non-exposed regions of the exposed resist layer, the exposed regions of exposed resist layer comprising an acid formed by exposing the PAG compound to the radiation;
heating the exposed resist layer, thereby forming a heated exposed resist layer comprising heated exposed regions and heated non-exposed regions of the heated exposed resist layer, wherein the heated exposed regions have lower solubility in a given developer compared to the heated non-exposed regions; and selectively removing the heated non-exposed regions using the given developer, thereby forming a patterned resist layer disposed on the surface of the substrate, the patterned resist layer comprising the heated exposed regions of the heated exposed resist layer.

* * * * *